(12) United States Patent
Uddin et al.

(10) Patent No.: US 10,695,446 B2
(45) Date of Patent: Jun. 30, 2020

(54) COMPOSITION AND METHOD FOR DETECTING HYPOXIA

(71) Applicant: Vanderbilt University, Nashville, TN (US)

(72) Inventors: Imam Uddin, Nashville, TN (US); Ashwath Jayagopal, Nashville, TN (US); Jashim Uddin, Nashville, TN (US); John S. Penn, Brentwood, TN (US); Lawrence J. Marnett, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/567,355

(22) PCT Filed: May 2, 2016

(86) PCT No.: PCT/US2016/030474
§ 371 (c)(1),
(2) Date: Oct. 17, 2017

(87) PCT Pub. No.: WO2016/179117
PCT Pub. Date: Nov. 10, 2016

(65) Prior Publication Data
US 2018/0085475 A1    Mar. 29, 2018

Related U.S. Application Data

(60) Provisional application No. 62/156,055, filed on May 1, 2015, provisional application No. 62/294,210, filed on Feb. 11, 2016.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *A61K 31/4545* | (2006.01) |
| *A61K 31/05* | (2006.01) |
| *A61K 31/19* | (2006.01) |
| *A61K 31/4178* | (2006.01) |
| *C07D 493/16* | (2006.01) |
| *C07D 403/14* | (2006.01) |
| *A61K 31/4375* | (2006.01) |
| *A61K 31/045* | (2006.01) |
| *C07D 405/14* | (2006.01) |
| *G01N 33/50* | (2006.01) |
| *C07D 487/22* | (2006.01) |
| *A61K 45/06* | (2006.01) |
| *C12Q 1/26* | (2006.01) |
| *G01N 33/52* | (2006.01) |

(Continued)

(52) U.S. Cl.
CPC ........ *A61K 49/0052* (2013.01); *A61K 31/045* (2013.01); *A61K 31/05* (2013.01); *A61K 31/19* (2013.01); *A61K 31/4178* (2013.01); *A61K 31/4375* (2013.01); *A61K 31/454* (2013.01); *A61K 31/4545* (2013.01); *A61K 31/517* (2013.01); *A61K 31/58* (2013.01); *A61K 45/06* (2013.01); *A61K 49/0021* (2013.01); *A61K 49/0023* (2013.01); *A61K 49/0032* (2013.01); *A61K 49/0041* (2013.01); *A61P 27/02* (2018.01); *A61P 43/00* (2018.01); *C07D 403/14* (2013.01); *C07D 405/14* (2013.01); *C07D 487/22* (2013.01); *C07D 493/16* (2013.01); *C09B 62/3435* (2013.01); *C09B 62/78* (2013.01); *C09K 11/06* (2013.01); *C12Q 1/26* (2013.01); *G01N 33/50* (2013.01); *G01N 33/52* (2013.01); *A61K 49/0017* (2013.01); *C09K 2211/1018* (2013.01); *G01N 2800/7038* (2013.01)

(58) Field of Classification Search
None
See application file for complete search history.

(56) References Cited

U.S. PATENT DOCUMENTS

| | | | |
|---|---|---|---|
| 2002/0115649 A1* | 8/2002 | Woodburn | ........... A61K 31/407 514/185 |
| 2008/0085237 A1 | 4/2008 | Raleigh et al. | |

(Continued)

OTHER PUBLICATIONS

Okuda, K et al., 2-Nitroimidazole-Tricarbocyanine Conjugate as a Near-infrared Fluorescent Probe for in Vivo Imaging of Tumor Hypoxia. Bioconjugate Chemistry. Feb. 16, 2012, vol. 23, No. 3; pp. 324-329.

(Continued)

*Primary Examiner* — Michael G. Hartley
*Assistant Examiner* — Melissa J Perreira
(74) *Attorney, Agent, or Firm* — Stites & Harbison PLLC; Mandy Wilson Decker

(57) ABSTRACT

A compound and method for detecting hypoxic cells and tissue are provided. The compound includes a probe selected from the group consisting of a hypoxia sensitive 2-nitroimidazole containing fluorescence imaging probe, a hypoxia sensitive reversible ON-OFF fluorescence imaging probe, a hypoxia sensitive azo-based fluorescence imaging probe, and combinations thereof. The method includes contacting the cells or tissue with the probe of any one of claims 1-13 and detecting fluorescent intensity of the cell or tissue, wherein increased fluorescent intensity indicates that the cells or tissue is hypoxic. Also provided are a method of synthesizing the compound and a method for synthesizing a therapeutic agent including the compound.

17 Claims, 37 Drawing Sheets

(51) Int. Cl.
  *A61P 27/02* (2006.01)
  *A61P 43/00* (2006.01)
  *A61K 31/454* (2006.01)
  *A61K 31/517* (2006.01)
  *A61K 31/58* (2006.01)
  *C09B 62/343* (2006.01)
  *C09B 62/78* (2006.01)
  *C09K 11/06* (2006.01)

(56) References Cited

U.S. PATENT DOCUMENTS

| 2008/0102026 | A1* | 5/2008 | Lee | A61K 51/00 424/1.11 |
| 2011/0002850 | A1 | 1/2011 | Collier et al. | |
| 2013/0096123 | A1* | 4/2013 | Eutick | A61K 31/4164 514/235.8 |
| 2014/0141084 | A1* | 5/2014 | Park | A61K 31/704 424/489 |

OTHER PUBLICATIONS

Zha, Z et al., Synthesis and Evaluation of Two Novel 2-nitroimidazole Derivatives as Potential PET Radioligands for Tumor Imaging. Nuclear Medicine and Biology. May 2011, vol. 38, No. 4; pp. 501-508.

Takahashi, et al., Reversible Off-On Fluorescence Probe for Hypoxia and Imaging of Hypoxia—Normoxia Cycles in Live Cells, J. Am. Chem. Soc. 2012, 134, 19588-19591.

Piao, et al., Development of Azo-Based Fluorescent Probes to Detect Different Levels of Hypoxia, Angew. Chem. Int. Ed. 2013, 52, 13028-13032.

Bergeron, et al., Detection of Hypoxic Cells With the 2-Nitroimidazole, EF5, Correlates With Early Redox Changes in Rat Brain After Perinatal Hypoxia—Ischemia, 1999, Neuroscience vol. 89, No. 4, pp. 1357-1366.

Evans, SM et al., Molecular Probes for Imaging of Hypoxia in the Retina. Bioconjugate Chemistry. Sep. 24, 2014, vol. 25, No. 11; pp. 2030-2037.

Uddin, I et al., Applications of Azo-Based Probes for Imaging Retinal Hypoxia. ACS Medicinal Chemistry Letters. Feb. 12, 2015, vol. 6, No. 4; pp. 445-449.

Uddin, I et al., In Vivo Imaging of Retinal Hypoxia using HYPOX-4-dependent Fluorescence in a Mouse Model of Laser-induced Retinal Vein Occlusion (RVO). Invest. Ophthalmol. Vis. Sci. In Press, 2017, 58(9), 3818-3824.

Uddin, I et al., In Vivo Imaging of Retinal Hypoxia in a Model of Oxygen-Induced Retinopathy. Scientific Reports 2016, 6, 31011.

* cited by examiner

Hypoxic

Normoxic

OIR, P13

RA, P13

COMPOSITION AND METHOD FOR DETECTING HYPOXIA

RELATED APPLICATIONS

This application claims priority from U.S. Provisional Application Ser. No. 62/156,055, filed May 1, 2015, and U.S. Provisional Application Ser. No. 62/294,210, filed Feb. 11, 2016, the entire disclosures of which are incorporated herein by this reference.

GOVERNMENT INTEREST

This invention was made with government support under grants EY023397, EY007533, EY023639, DK076169 and EY029693 awarded by the National Institutes of Health. The government has certain rights in the invention.

TECHNICAL FIELD

The presently-disclosed subject matter relates to compounds for detecting hypoxia and methods thereof. More particularly, the presently-disclosed subject matter relates to hypoxia targeted fluorescence imaging agents and methods in detection and treatment of retinal hypoxia.

BACKGROUND

Hypoxia of the retina has been associated with the initiation and progression of blinding retinal vascular diseases. For example, age-related macular degeneration (AMD), retinopathy of prematurity (ROP),[1,2] proliferative diabetic retinopathy (PDR),[3] and retinal vein occlusion (RVO)[4] are blinding conditions with neovascular components that develop from ischemia-induced retinal hypoxia. Typically, retinal hypoxia activates the transcription of hypoxia-regulated pro-angiogenic growth factors/cytokines such as vascular endothelial cell growth factor (VEGF)[9] and angiopoietin-like protein-4 (ANGPTL4).[10] These factors elicit a neovascular response that manifests in the formation of pre-retinal neovascular structures that enhance morbidity, often leading to blindness in individuals afflicted with ROP, PDR, and RVO.

More specifically, in ROP, ischemia arises from attenuated physiologic blood vessel development in preterm infants receiving supplemental oxygen to compensate for under-developed lung function.[5,6] When the oxygen therapy is discontinued and the infant is placed in normoxia, the peripheral retina is avascular (ischemia), and becomes hypoxic[7]. Hyperglycemia and hyperlipidemia are causally linked to capillary dropout and vasoregression in the diabetic retina, leading to focal avascularity (ischemia) and incipient retinal hypoxia that triggers the onset of PDR. Similarly, in branch RVO, injury or atherosclerosis results in the formation of an occlusive thrombus, reducing blood flow (ischemia) initiating the development of retinal hypoxia.[8]

In view thereof, several analytical platforms have been applied to measuring retinal oxygen pressure ($PO_2$) levels including, but not limited to, the use of oxygen sensitive electrodes,[11] nuclear magnetic resonance (NMR),[12] retinal oximetry,[13] oxygen-dependent molecular phosphorescence quenching,[14] doppler optical coherence tomography (D-OCT).[15] Oxygen electrodes permit the acquisition of reliable data but are invasive and cannot be used for rodents due to their small globes. NMR is minimally invasive, however it is not a direct measure of oxygen tension and the resolution is appreciably less than optical methods.[18-20] Retinal oximetry and doppler OCT are methods that hinge on the differences in the spectral characteristics of oxyhemoglobin and hemoglobin in the intravascular compartment, and their relative abundance in arteries compared to veins. These measurements may be performed in living systems, however, they are indirect and mathematical modeling is required to estimate the perivascular oxygen pressure. Phosphorescent quenching relies on intravascular oxygen levels providing only limited assessment of the oxygen pressure in the retinal tissue.

Other methods that have been applied to measuring $PO_2$ include visible-light optical coherence tomography (vis-OCT)[16] and immunohistochemical analysis.[17] For example, immunohistochemical analysis may include pimonidazole-mediated immunohistochemistry. While pimonidazole-mediated immunohistochemistry is a common method to study retinal hypoxia, the technique is limited by its exclusively ex vivo method of examination.[21,22] With regard to vis-OCT, although a number of methods have been reported in the literature to visualize tumor hypoxia using positron emission tomography, none of these methods have been applied to the detection of retinal hypoxia. Additionally, these vis-OCT methods carry the risks associated with use of short-lived isotopes. For these and other reasons, the techniques discussed above are not currently available or not suitable for measuring retinal hypoxia in living animals in real time.

In an attempt to address these issues, the instant inventors previously described the development of HYPDX-1, HYPDX-2, and HYPDX-3 as sensitive fluorophore-labeled imaging probes to detect hypoxia.[23,24] These fluorescent probes are reduced by nitroreductases or azoreductases, facilitating their retention within hypoxic cells of the retina, allowing ex vivo hypoxia detection.[25] However, their application to in vivo imaging is limited due to poor pharmacokinetic parameters.

Accordingly, the currently available methods fail to provide noninvasive imaging techniques capable of detecting and monitoring retinal hypoxia in living systems. Thus, there is a need for improved compositions and methods that would provide in vivo hypoxia imaging. The presently disclosed embodiments fulfill such a need, and offer other related advantages.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes imaging agents/probes and methods for hypoxia imaging. In some embodiments, the method includes in vivo retinal imaging in a subject. In vivo retinal imaging of hypoxia may be useful for early detection and timely treatment of retinal diseases.

Further provided, in some embodiments of the presently disclosed subject matter, is a method of detecting hypoxia in a subject by administering an effective amount of compound to the subject in need thereof. In some embodiments, detecting hypoxia includes detection of hypoxia in age-related macular degeneration (AMD), retinopathy of prematurity (ROP), diabetic retinopathy (DR), and branch retinal vein occlusion (BRVO).

Still further, in some embodiments of the presently disclosed subject matter, is a method of treating hypoxia in a subject by administering an effective amount of the compound to the subject in need thereof. In some embodiments, the hypoxia is retinal hypoxia.

BRIEF DESCRIPTION OF THE DRAWINGS

A better understanding of the features and advantages of the presently-disclosed subject matter will be obtained by reference to the following detailed description that sets forth illustrative embodiments as well as the Figures described below.

FIG. 22A illustrates R28 cells treated with HYPDX-4 (100 μM) and variable oxygen concentrations. HYPDX-4-dependent fluorescence increased with decreasing oxygen concentration.

FIG. 22B illustrates R28 cells treated with concentrations of HYPDX-4 ranging from 10 to 100 μM and 0.1% oxygen concentration.

FIG. 22C illustrates ARPE19 cells treated with concentrations of HYPDX-4 ranging from 10 to 100 μM and 0.1% oxygen concentration.

FIG. 22D illustrates MIO-M1 cells treated with concentrations of HYPDX-4 ranging from 10 to 100 μM and 0.1% oxygen concentration.

FIG. 23A shows DAPI fluorescence activity in R28 cells treated with HYPDX-4 (100 μM) and 0.1% oxygen for 4 hours.

FIG. 23B shows HYPDX-4 fluorescence activity in R28 cells treated with HYPDX-4 (100 μM) and 0.1% oxygen for 4 hours.

FIG. 23C shows DAPI fluorescence activity in R28 cells under normoxic conditions.

FIG. 23D shows HYPDX-4 fluorescence activity in R28 cells under normoxic conditions.

FIG. 24A shows DAPI fluorescence activity in MIO-M1 cells under hypoxia.

FIG. 24B shows pimonidazole fluorescence activity in MIO-M1 cells under hypoxia.

FIG. 24C shows the results of FIGS. 24A and B merged into a single image.

FIG. 24D shows DAPI fluorescence activity in MIO-M1 cells under normoxia.

FIG. 24E shows pimonidazole fluorescence activity in MIO-M1 cells under normoxia.

FIG. 24F shows the results of FIGS. 24D and E merged into a single image.

FIG. 25A shows bright field image of OIR (P13) retina.

FIG. 25B shows an in vivo image of the retina in FIG. 25A, hypoxia was clearly detected by HYPDX-4-dependent fluorescence within the central avascular retina (green).

FIG. 25C shows bright field image of age-matched RA pup (P13) to that of FIG. 25A.

FIG. 25D shows that HYPDX-4-dependent fluorescence was undetectable in aged-matched RA pups;

FIG. 26A shows ex vivo HYPDX-4-dependent fluorescence in the central avascular retina (green) of OIR mouse retina.

FIG. 26B shows the retina of FIG. 26A counterstained with IB4, highlighting the peripheral vascular retina.

FIG. 26C shows FIGS. 26A and B merged.

FIG. 26D shows IB4 staining of the retinal vasculature (red) from an RA pup, illustrating that RA pups showed minimal ex vivo HYPDX-4-dependent fluorescence.

FIG. 28A illustrates alternating regions of hypoxia observed in the inner retina with hypoxic regions overlapping with retinal avascularity (green); hypoxia was visualized in the inner plexiform and inner nuclear layers.

FIG. 28B confirms hypoxia in the inner retina by pimonidazole-adduct immunostaining (red).

FIG. 29A illustrates immunofluorescence staining of human Müller cells with GS.

FIG. 29B illustrates immunofluorescence staining of human Müller cells with HYPDX-4.

FIG. 29C illustrates immunofluorescence staining of human Müller cells with DAPI, which represents nuclear staining.

FIG. 29D is an image merging the immunofluorescence staining of FIGS. 29A-C. Colocalization of Müller cells staining (FIG. 29A) with HYPDX-4 (FIG. 29B) was minimally overlapped in OIR retinal cross section.

FIG. 30A illustrates bright field fundus photograph of the RVO mouse.

FIG. 30B illustrates HYPDX-4-dependent fluorescence activity detected proximal to and downstream from the site of photocoagulation, indicating retinal hypoxia.

FIG. 30C illustrates fluorescence angiography of the same eye shown in FIGS. 30A-B using TRITC-Dextran. The fluorescence angiography shows a lack of perfusion downstream from the photocoagulated site.

FIG. 30D shows an image merging FIGS. 30B and C.

FIG. 31A illustrates ex vivo HYPDX-4 dependent fluorescence activity detected in retina.

FIG. 31B illustrates confirmation of hypoxia in RVO mice retina by pimonidazole-adduct immunostaining.

FIG. 31C illustrates IB4 staining of the retinal vasculature with an arrow indicating the photocoagulation site.

FIG. 31D shows an image merging FIGS. 31B and C.

FIG. 33A illustrates electroretinography (ERG) measurements of mean a-wave amplitudes at various flash intensities of dark-adapted mice 7 days post systemic administration of HYPDX-4. The measurements revealed no significant changes in mean a-wave amplitudes as compared to vehicle (PBS) and sodium fluorescein (control) groups.

FIG. 33B illustrates electroretinography (ERG) measurements of mean b-wave amplitudes at various flash intensities of dark-adapted mice 7 days post systemic administration of HYPDX-4. The measurements revealed no significant changes in mean b-wave amplitudes as compared to vehicle (PBS) and sodium fluorescein (control) groups.

FIG. 34A illustrates DAPI staining of nuclei.

FIG. 34B illustrates DNase 1 treated retinal cross section serving as a positive control; fragmented DNA was clearly visible.

FIG. 34C shows an image merging FIGS. 34A and B.

FIG. 34D illustrates DAPI staining of nuclei.

FIG. 34E illustrates HYPDX-4 treated retinal cross-section showed no cellular apoptosis.

FIG. 34F shows an image merging FIGS. 34D and E.

FIG. 35A illustrates in vitro cellular viability assessed by BrdU incorporation in R28 cells.

FIG. 35B illustrates in vitro cellular viability assessed by BrdU incorporation in MIO-M1 cells.

As illustrated in FIG. 38, HYPDX-4 possesses high photostability in solution for at least 24 hours.

DESCRIPTION OF EXEMPLARY EMBODIMENTS

Figure 1:
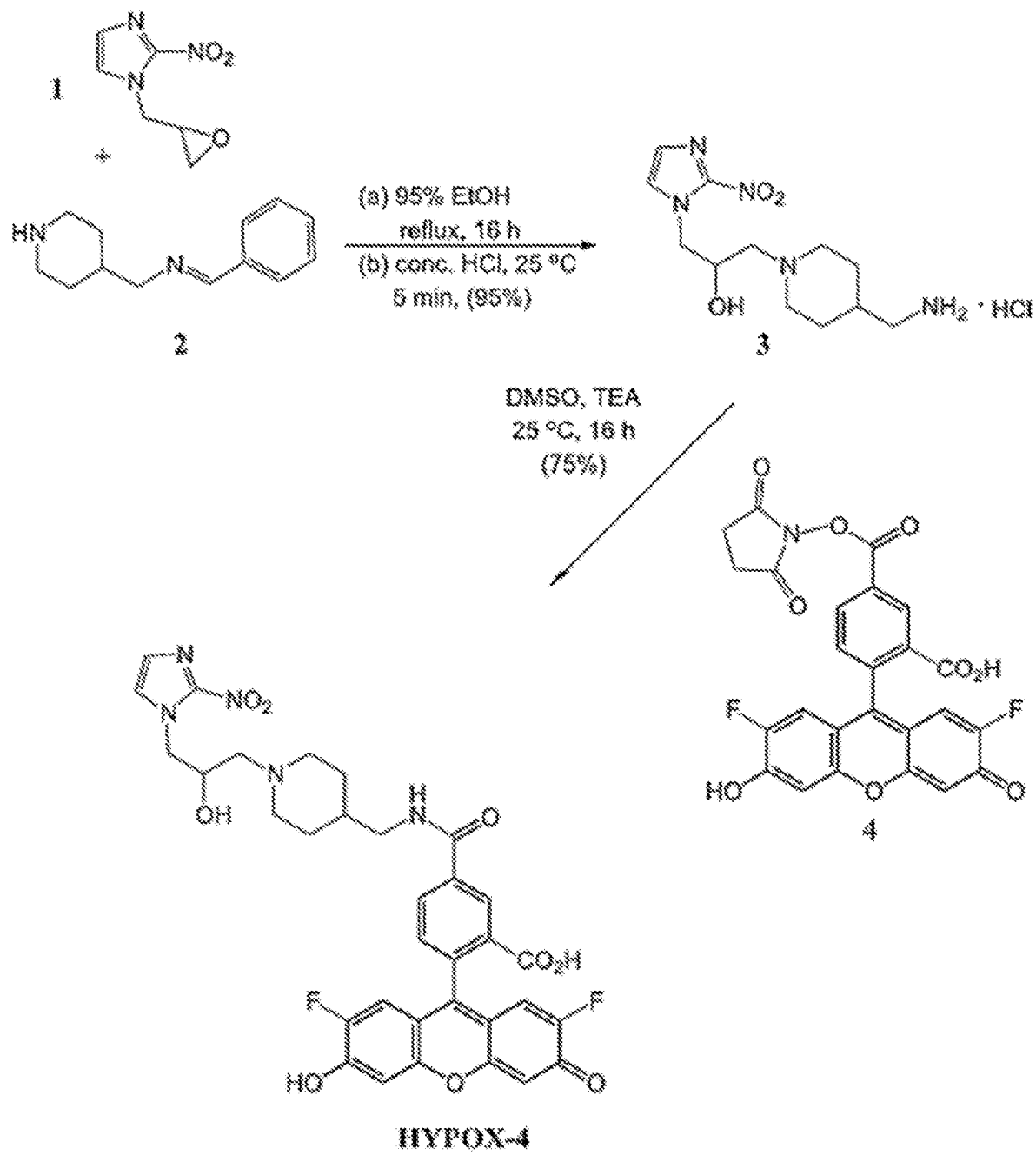
FIG. 1 is a schematic view showing the synthesis of HYPDX-4.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "administering" refers to any method of providing an isolated peptide, composition thereof, and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, intracameral (into anterior chamber) administration, subretinal administration, sub-Tenon's administration, peribulbar administration, administration via topical eye drops, and the like. Administration can be continuous or intermittent. In various aspects, a preparation can be administered therapeutically; that is, administered to treat an existing disease or condition (e.g., hypoxia). In further various aspects, a preparation can be administered prophylactically; that is, administered for prevention of a disease or condition.

As used herein, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

As used herein, the terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylactic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The presently-disclosed subject matter generally relates to compounds for detecting hypoxia, and more particularly relates to certain novel retina hypoxia detecting imaging compounds. Additionally, the presently-disclosed subject matter relates to methods and pharmaceutical compositions for detecting and treating retina hypoxia.

In some embodiments of the presently disclosed subject matter, a compound is provided for detecting and treating hypoxia. In some embodiments, the compound is an imaging probe. In some embodiments, the imaging probe is hypoxia sensitive 2-nitroimidazole containing fluorescence imaging probe. Non-limiting examples of these imaging probes include:

Type A Hypoxia sensitive 2-nitroimidazole containing fluorescence imaging probes:

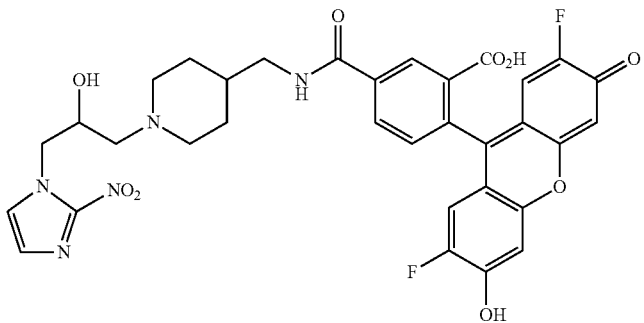

JU-1020

(HYPOX-4)
MI-53
677.61

-continued
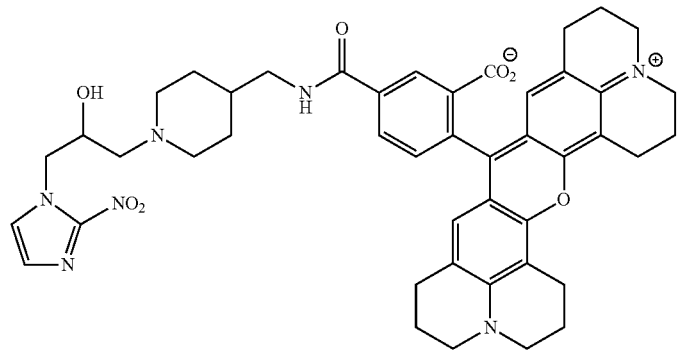
MI-26
799.91
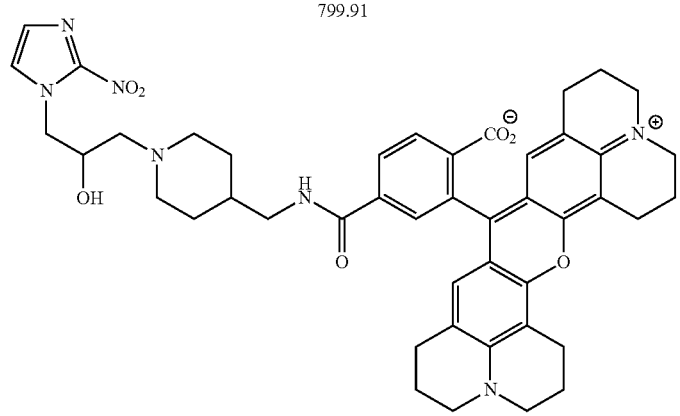
MI-7
790.91
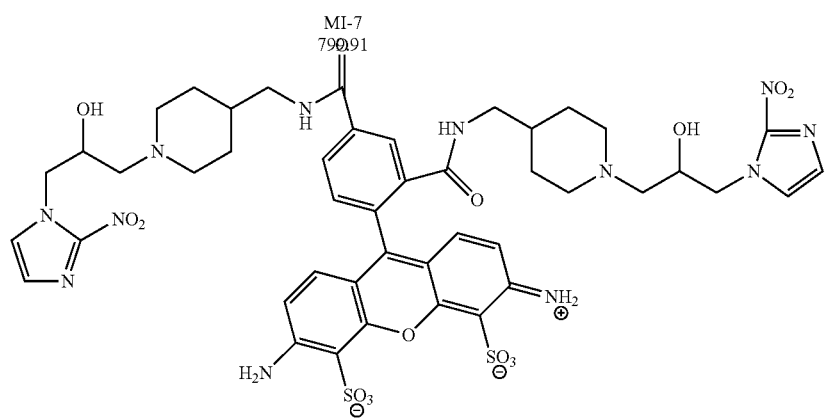
MI-42
1064.09
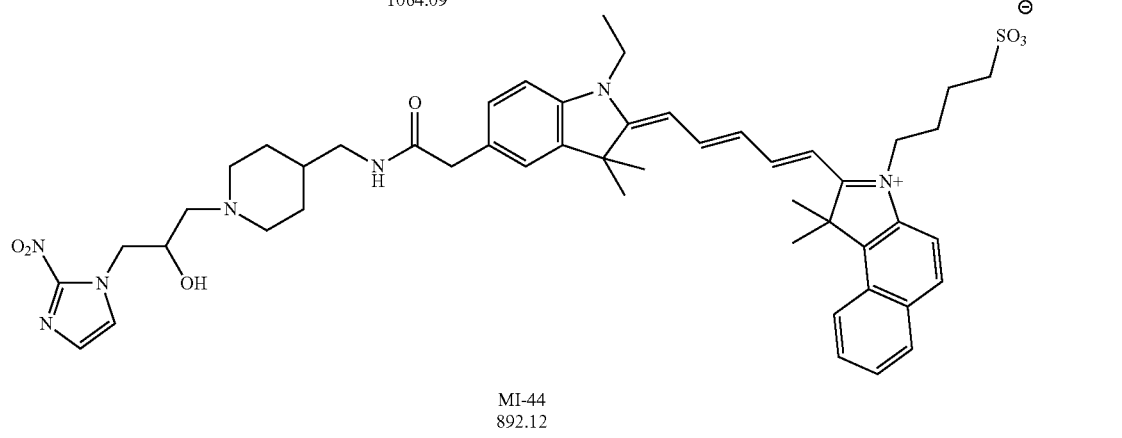
MI-44
892.12

In some embodiment, the hypoxia sensitive 2-nitroimidazole containing fluorescence imaging probe is synthesized from a fluorescence imaging probe moiety and a hypoxia sensitive 2-nitroimidazole moiety. For example, in one embodiment, synthesis of the imaging agent includes first generating a free amine by adding triethylamine to a stirred solution of pimonidazole amine hydrochloride in dimethylsulfoxide. After adding the triethylamine and stirring for any suitable amount of time to generate the free amine (e.g., about 5 minutes), an N-succinimidyl ester compound is added and the resulting solution is stirred for any suitable amount of time for the reaction to proceed. Next, the solvent is removed by any suitable process, such as, but not limited to, lyophyllization, to form a crude product. The crude product is then purified, for example, by silica gel column chromatography, to obtain pure HYPDX-4 as the imaging agent. The structure of HYPDX-4 was confirmed by $^1$H-NMR, $^{19}$F-NMR, and high-resolution mass spectroscopic analysis.

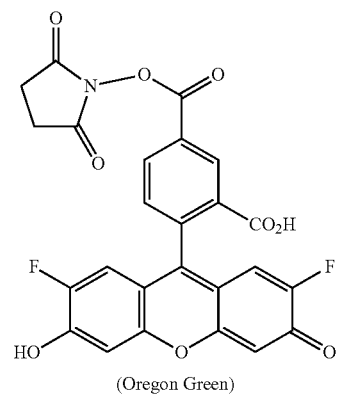

(Oregon Green)
Fluorescence imaging probe moiety

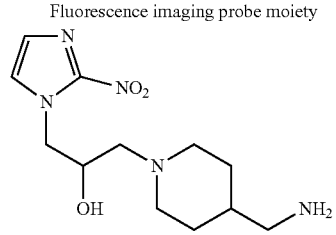

Figure 2:
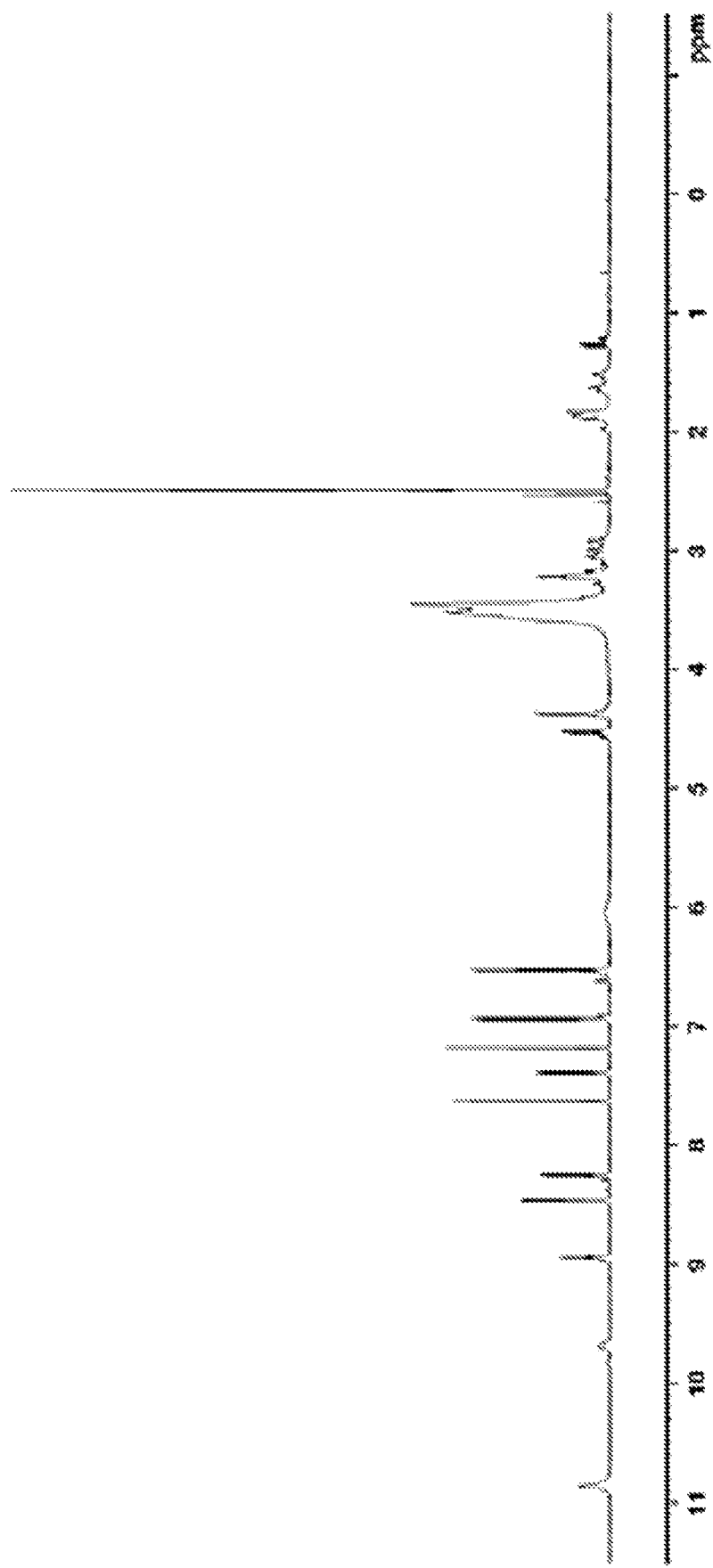
FIG. 2 shows $^1$H-NMR spectra for HYPDX-4.
Figure 3:
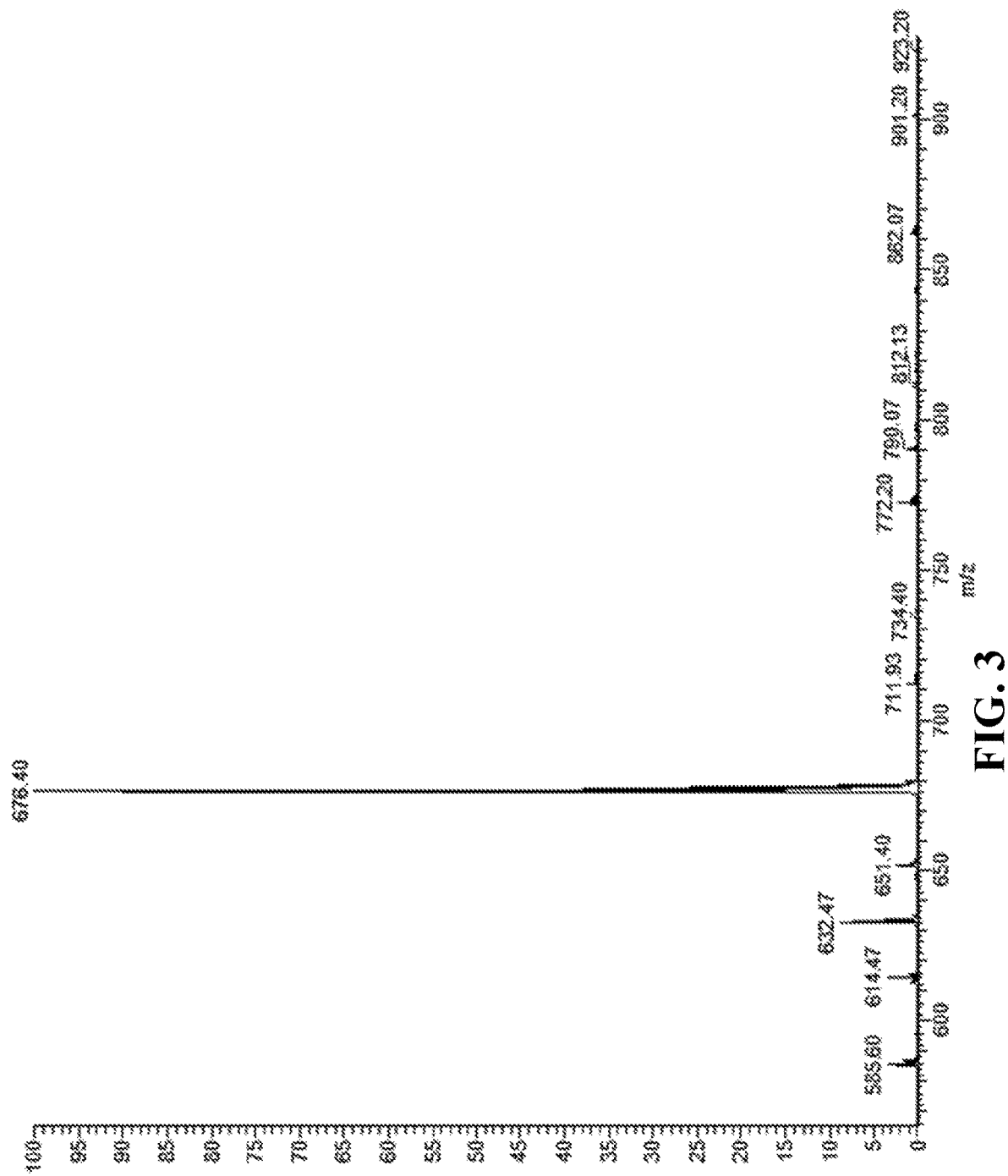
FIG. 3 shows LRMS data for HYPDX-4.
Figure 4:
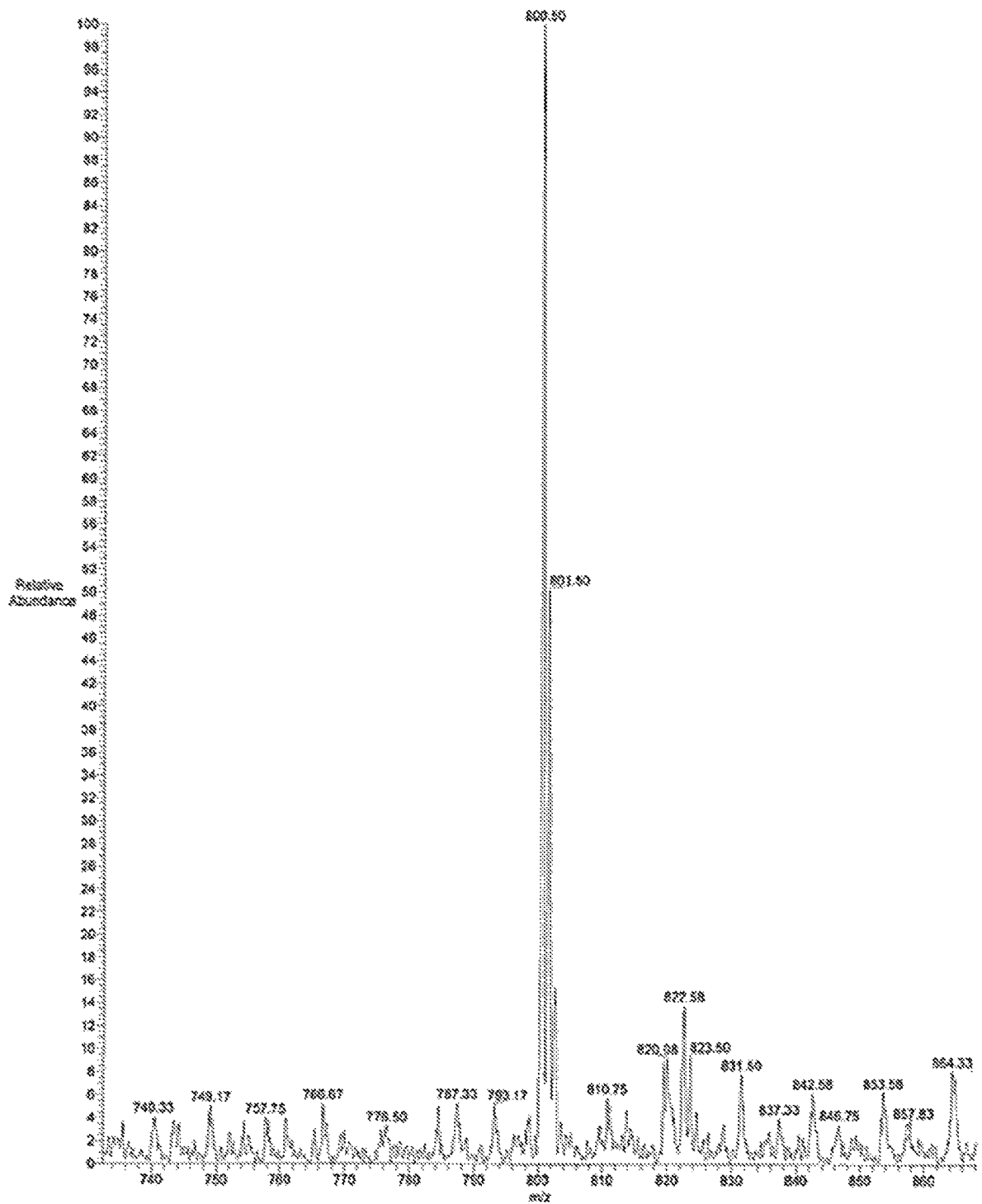
FIG. 4 shows LRMS data for MI-26.
Figure 5:
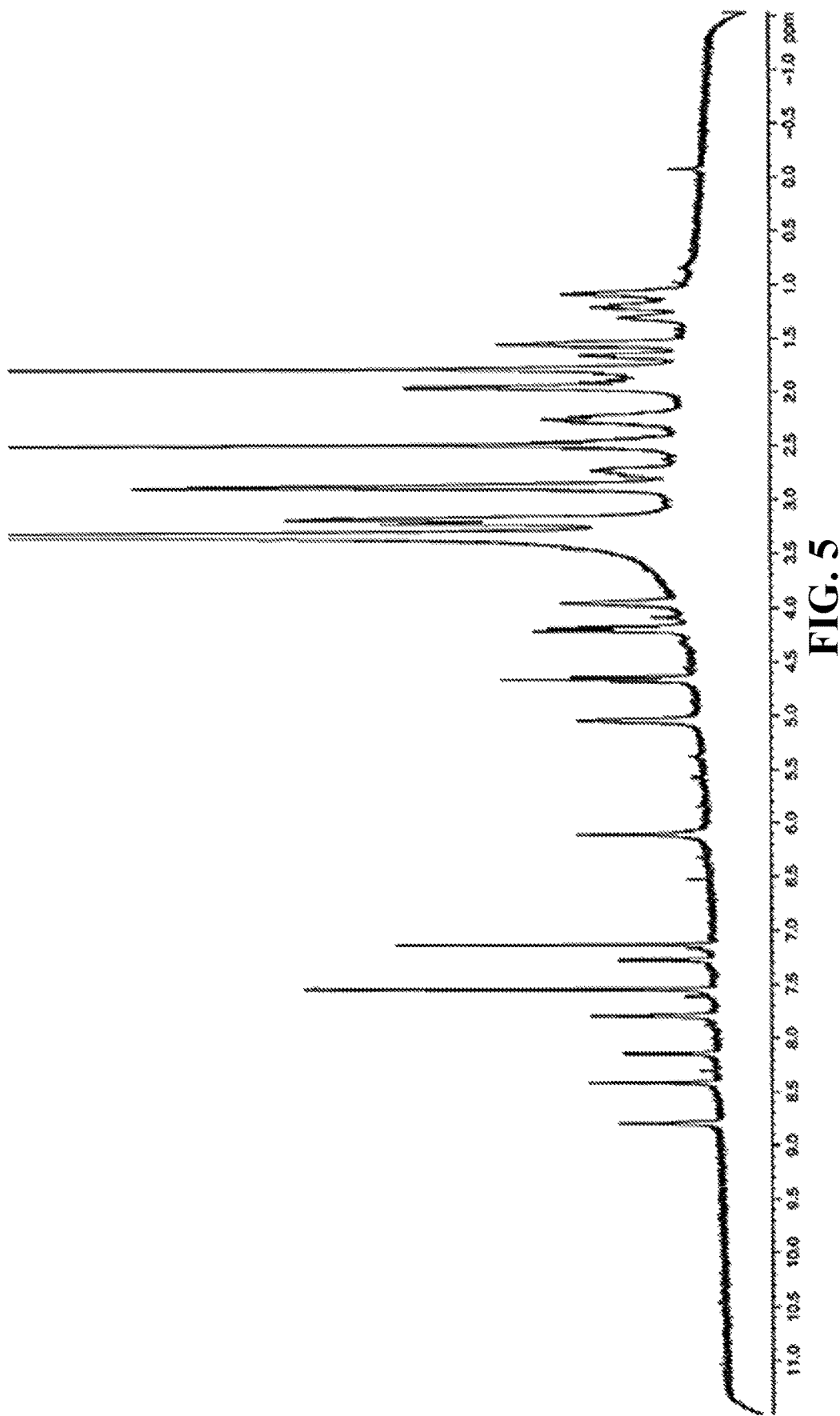
FIG. 5 shows $^1$H-NMR spectra for MI-26.
Figure 6:
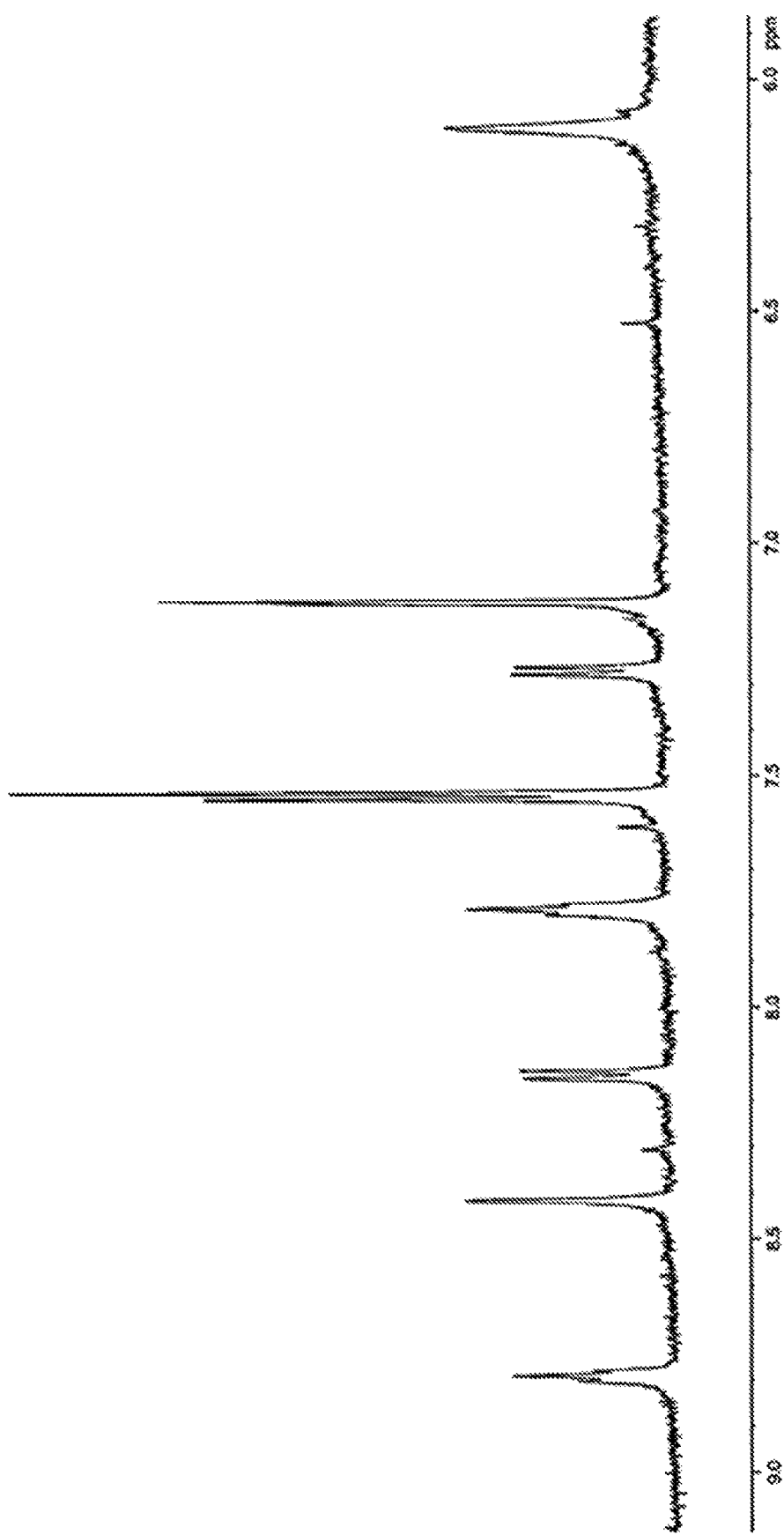
FIG. 6 shows $^1$H-NMR spectra for MI-26.
Figure 7:
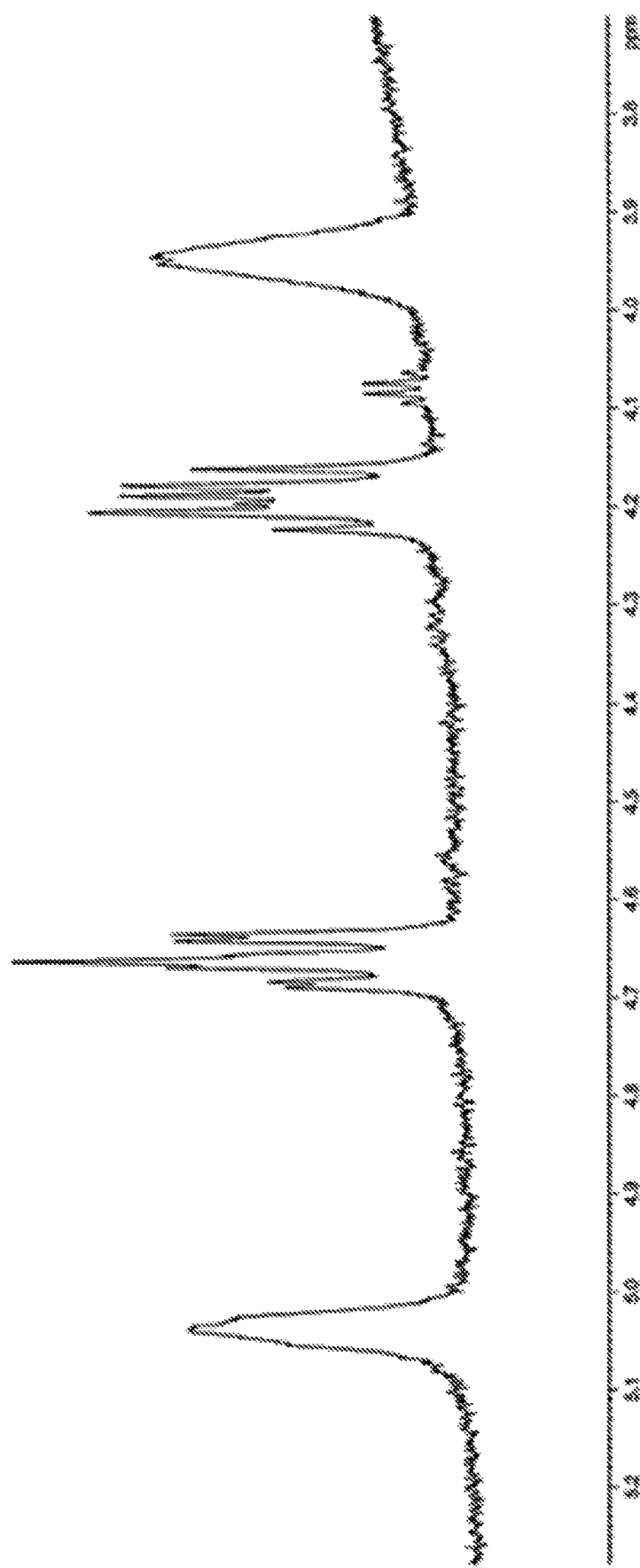
FIG. 7 shows $^1$H-NMR spectra for MI-26.
Figure 8:
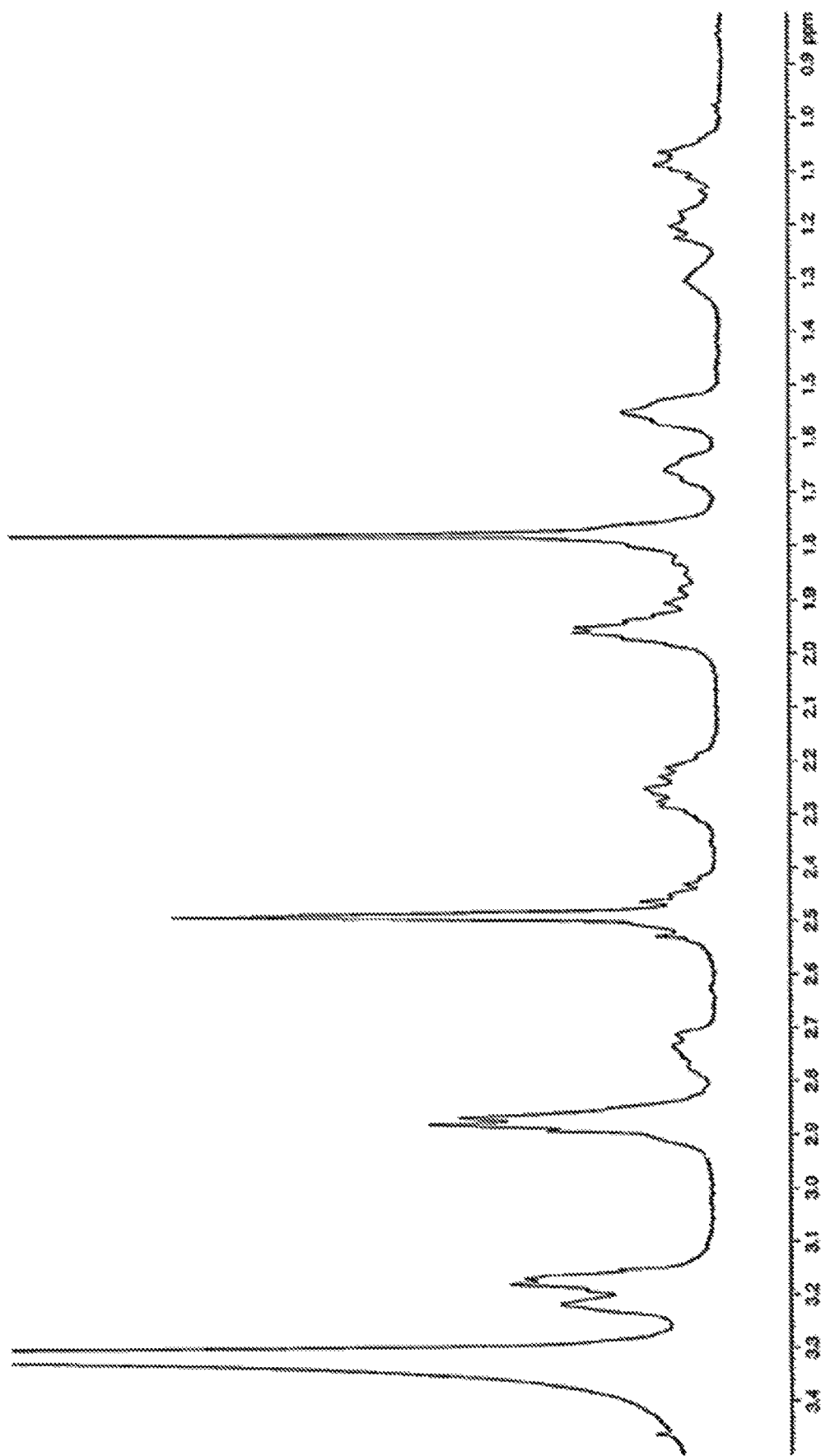
FIG. 8 shows $^1$H-NMR spectra for MI-26.
Figure 9:
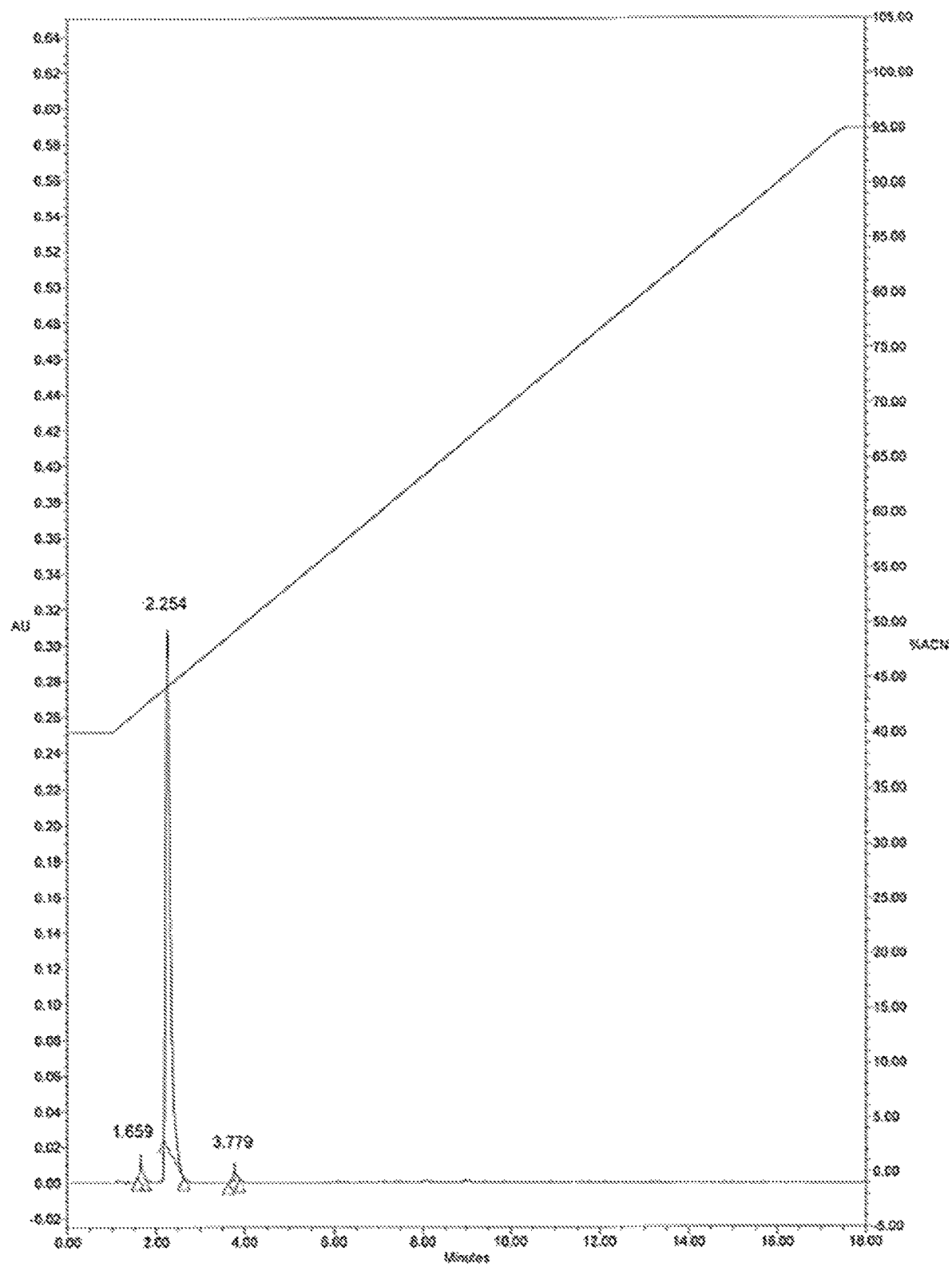
FIG. 9 shows HPLC data for MI-26.

(1-(4-(aminomethyl)piperidin-1-yl)-3-(2-nitro-1H-imidazole-1-yl)propan-2-ol)
Hypoxia sensitive 2-nitroimidazole moiety In another example, as illustrated in FIG. 1, the HYPDX-4 compound shown above is synthesized from an Oregon Green moiety and a 1-(4-(aminomethyl)piperidin-1-yl)-3-(2-nitro-1H-imidazole-1-yl)propan-2-ol moiety. $^1$H-NMR spectra and LRMS data from a synthesized HYPDX-4 compound is shown in FIGS. 2-3, respectively. Structural examples of the moieties used to form HYPDX-4 are shown below.

Figure 10:
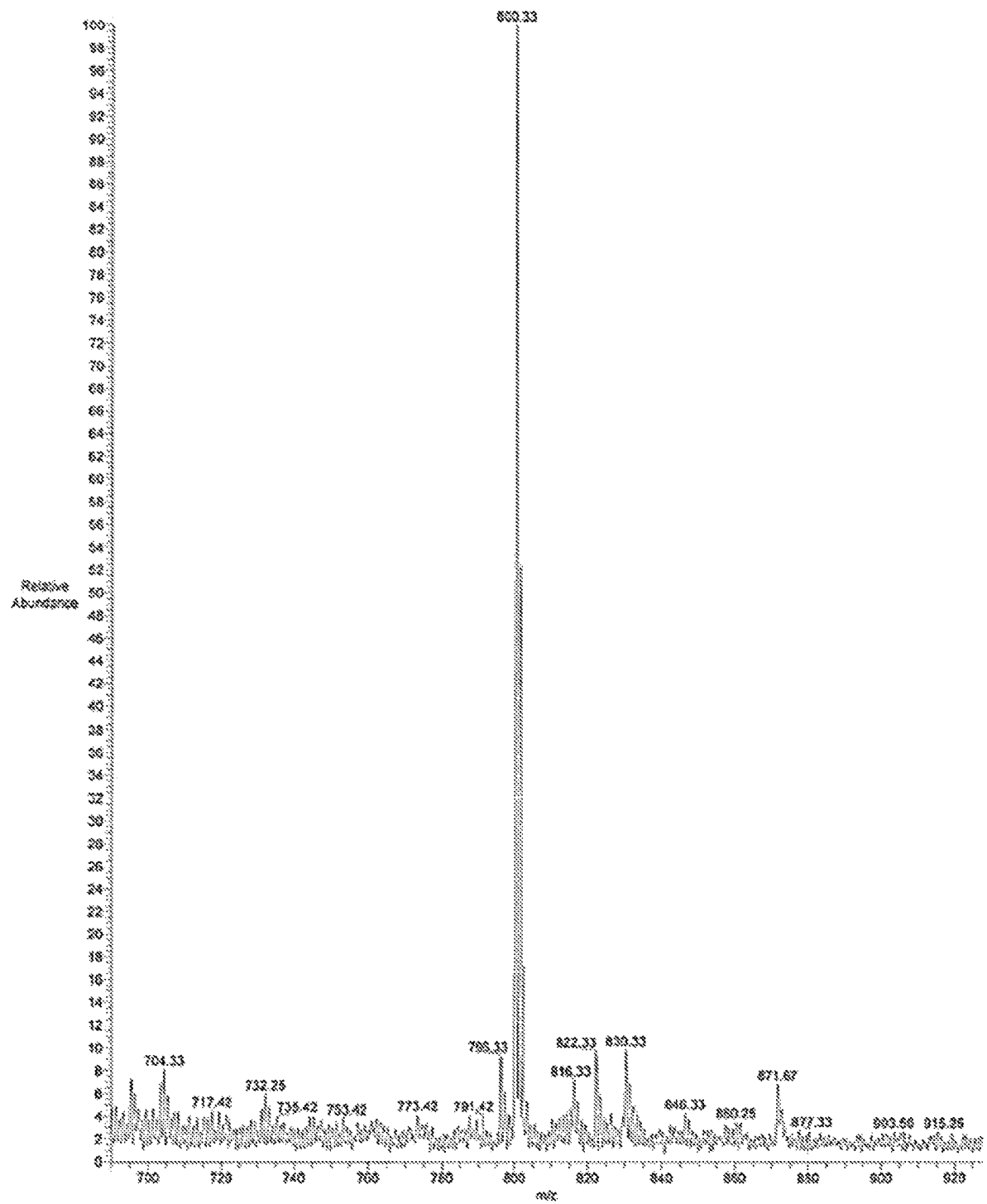
FIG. 10 shows LRMS data for MI-7.
Figure 11:
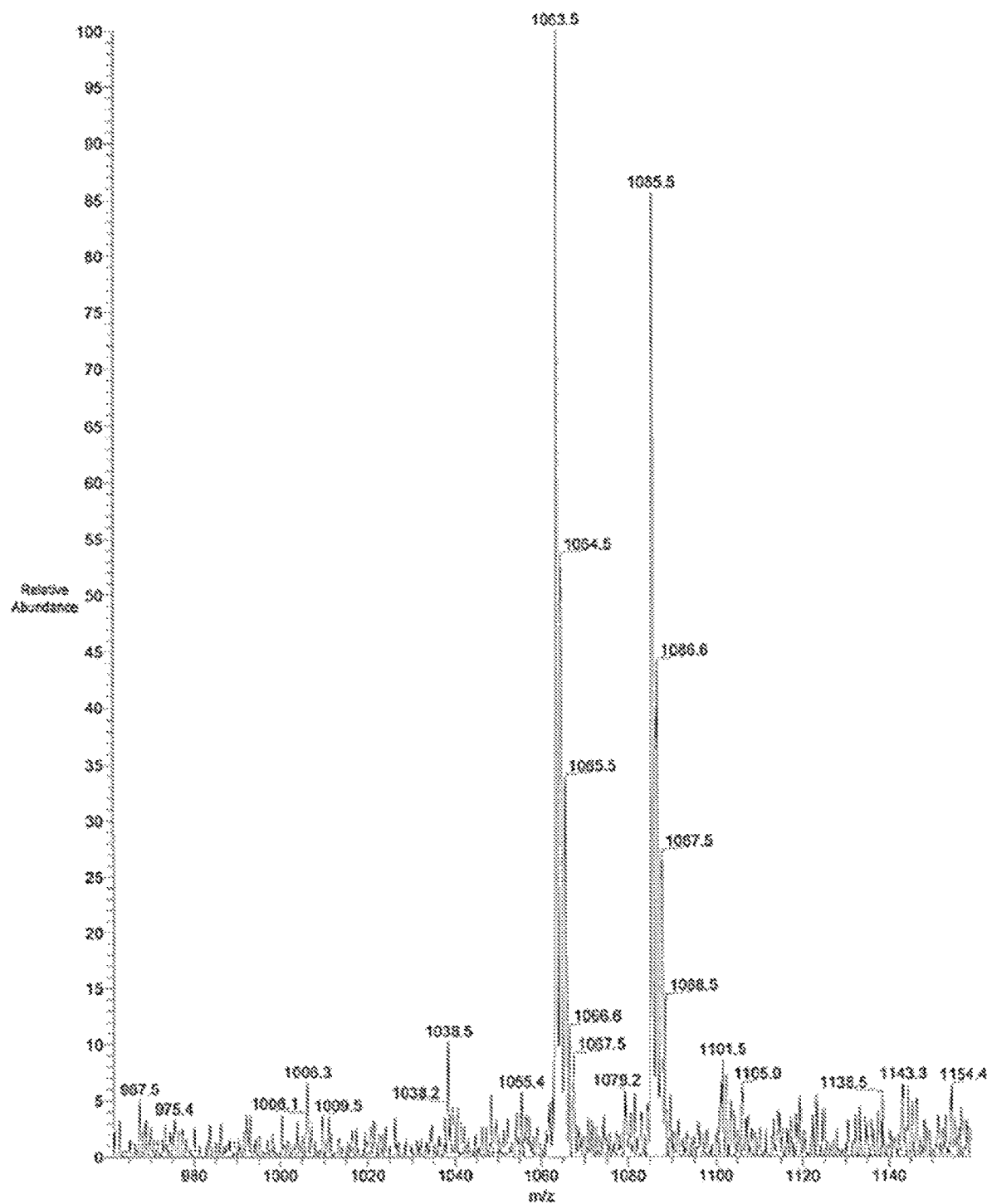
FIG. 11 shows LRMS data for MI-42.
Figure 12:
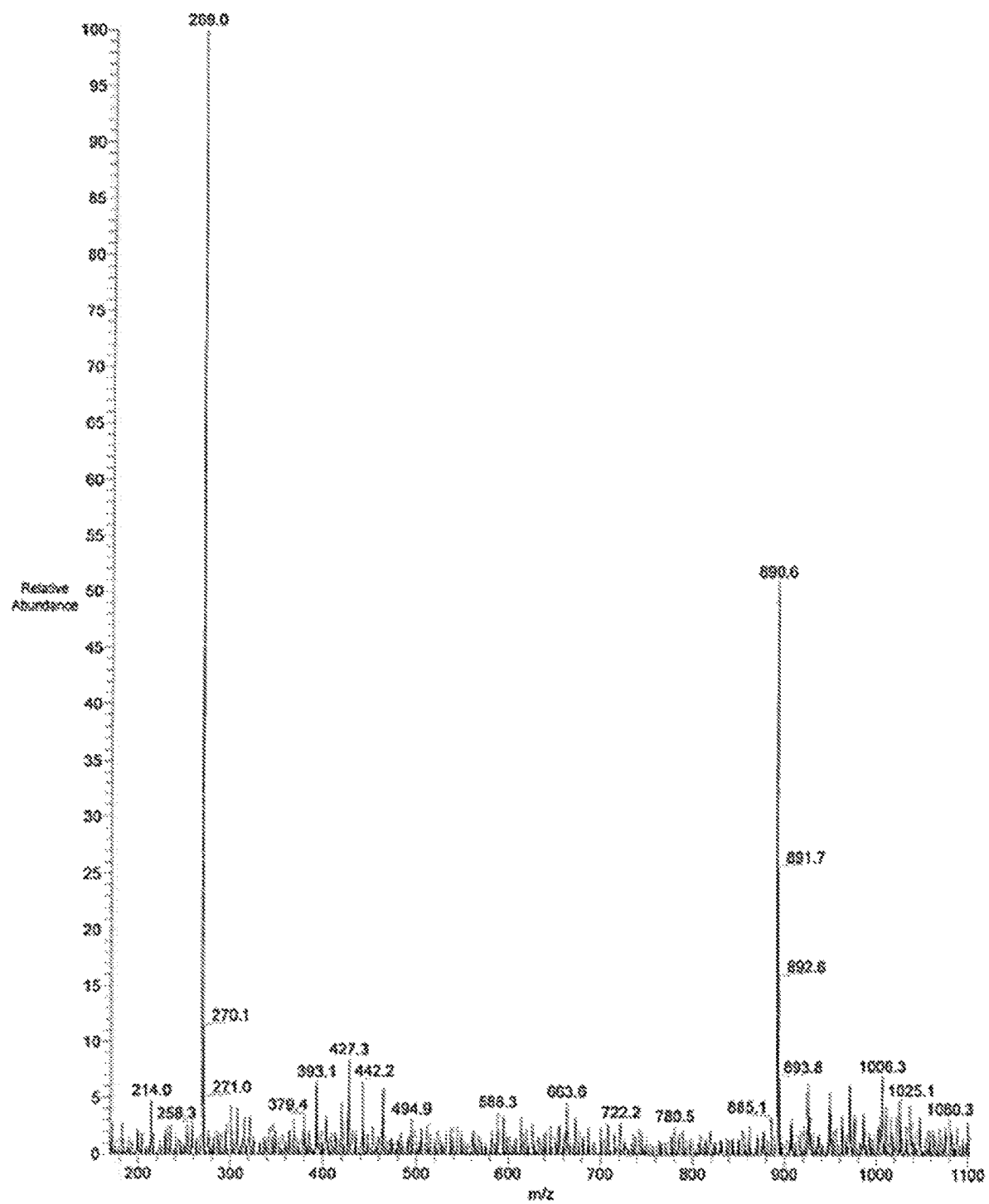
FIG. 12 shows LRMS data for MI-44.

Photophysical characterization from synthesis of the other hypoxia sensitive 2-nitroimidazole containing fluorescence imaging probes recited above is shown in FIGS. 4-12. More specifically, FIGS. 4-9 illustrate $^1$H-NMR spectra, LRMS, and HPLC data for MI-26, FIG. 10 illustrates LRMS data for MI-7, FIG. 11 illustrates LRMS data for MI-42, and FIG. 12 illustrates LRMS data for MI-44.

In some embodiments, the imaging probe is a hypoxia sensitive reversible ON-OFF fluorescence imaging probe. Non-limiting examples of these imaging probes are below.

Type B Hypoxia sensitive reversible ON-OFF fluorescence imaging probes:

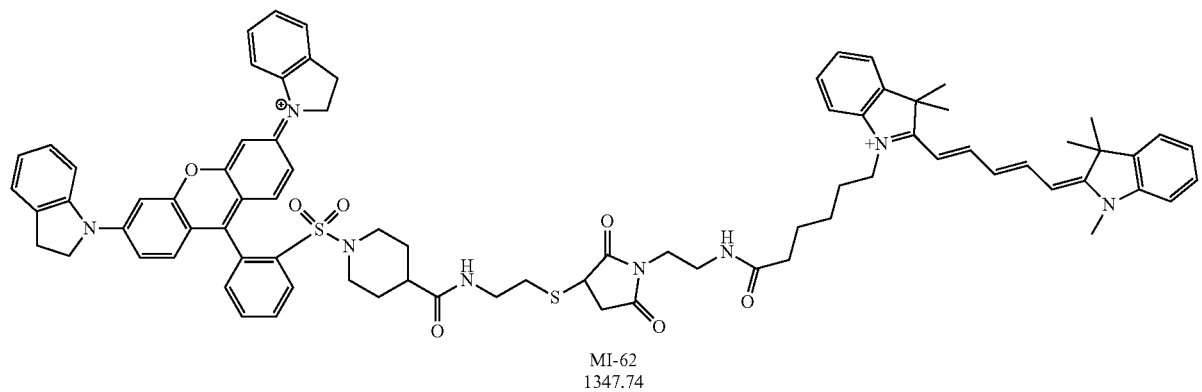

MI-62
1347.74

Figure 13:
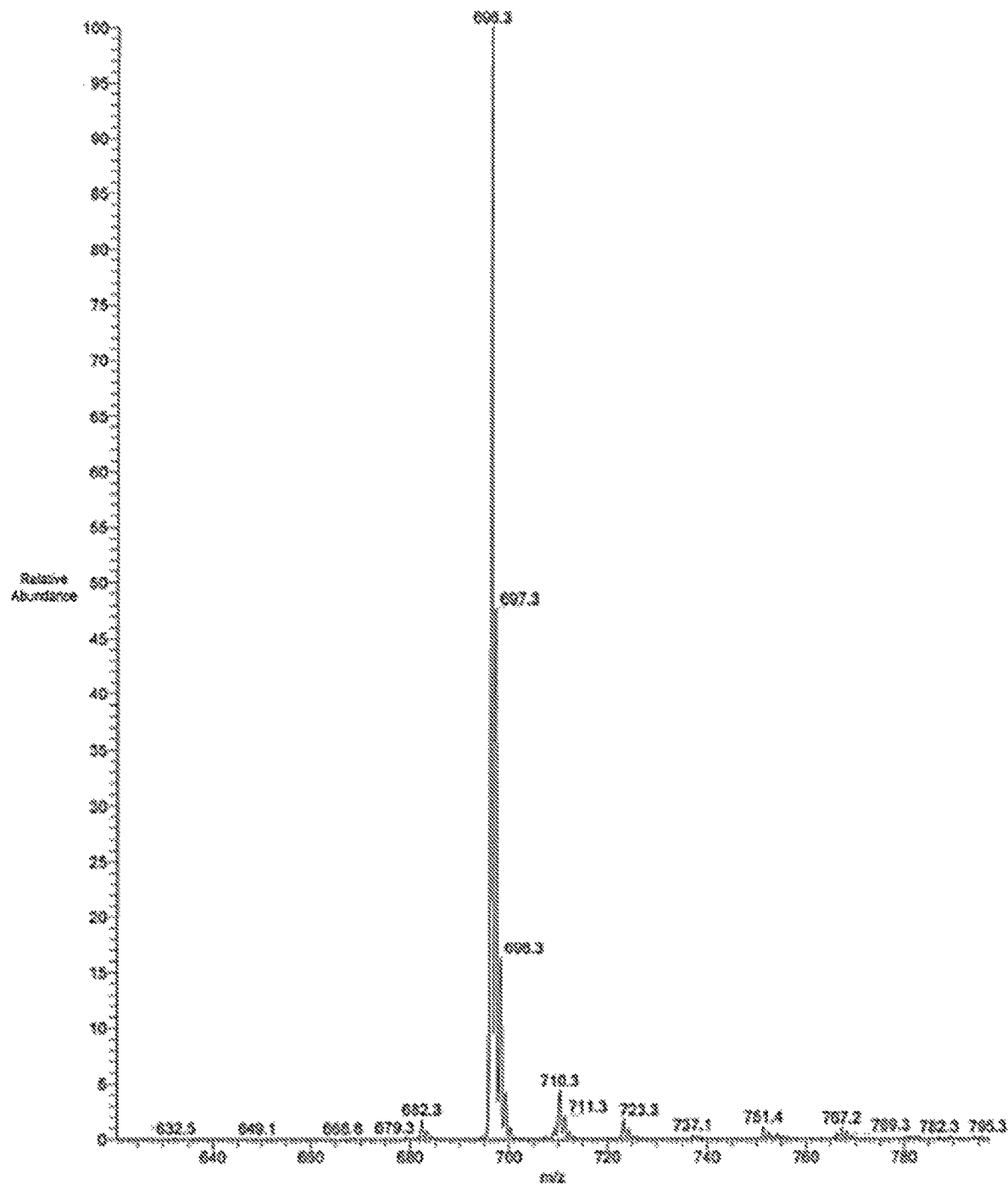
FIG. 13 shows LRMS data for MI-62.

Photophysical characterization from synthesis of the hypoxia sensitive reversible ON-OFF fluorescence imaging probe recited above is shown in FIG. 13. More specifically, FIG. 13 illustrates LRMS data for MI-62.

In some embodiments, the imaging probe is a hypoxia sensitive azo-based fluorescence imaging probes. In some embodiments, these probes features a cleavable azo-bond. Non-limiting examples of these imaging probes are below.

Type C Hypoxia-sensitive azo-based fluorescence imaging probes, which features a cleavable azo-bond:

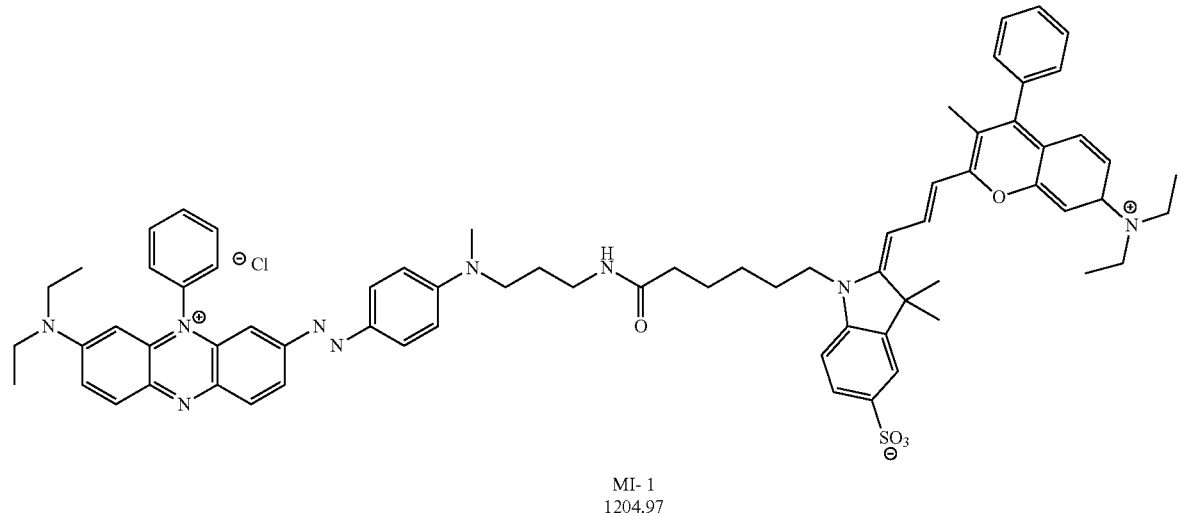

JU-1017

MI-1
1204.97

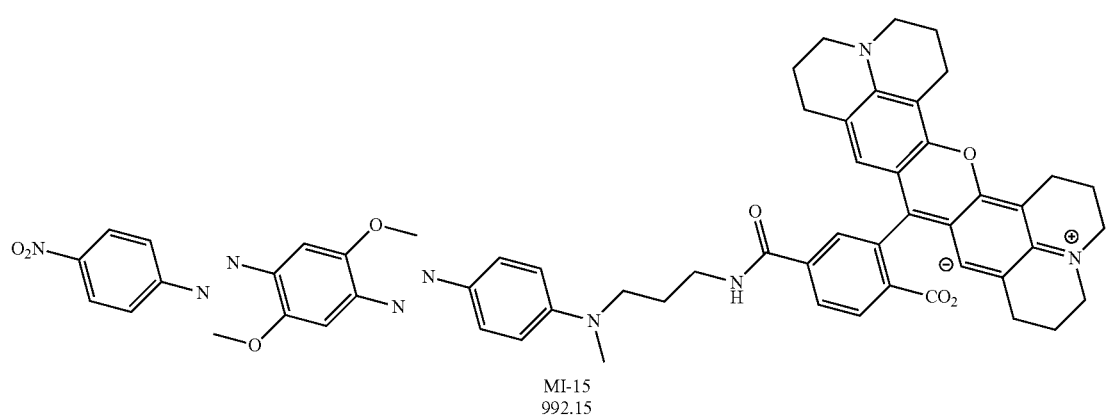

JU-1018

MI-15
992.15

Figure 14:
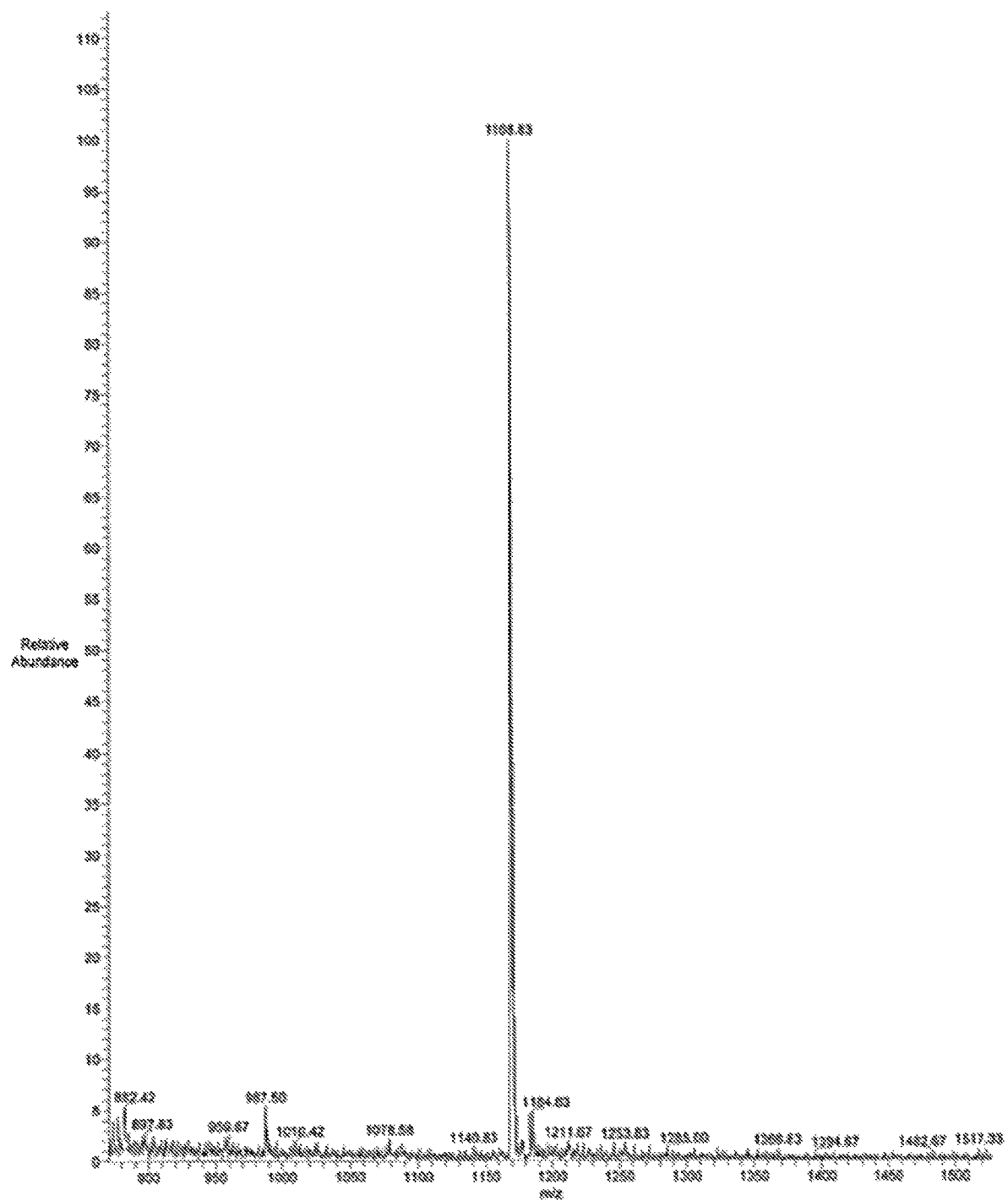
FIG. 14 shows LRMS data for MI-1.
Figure 15:
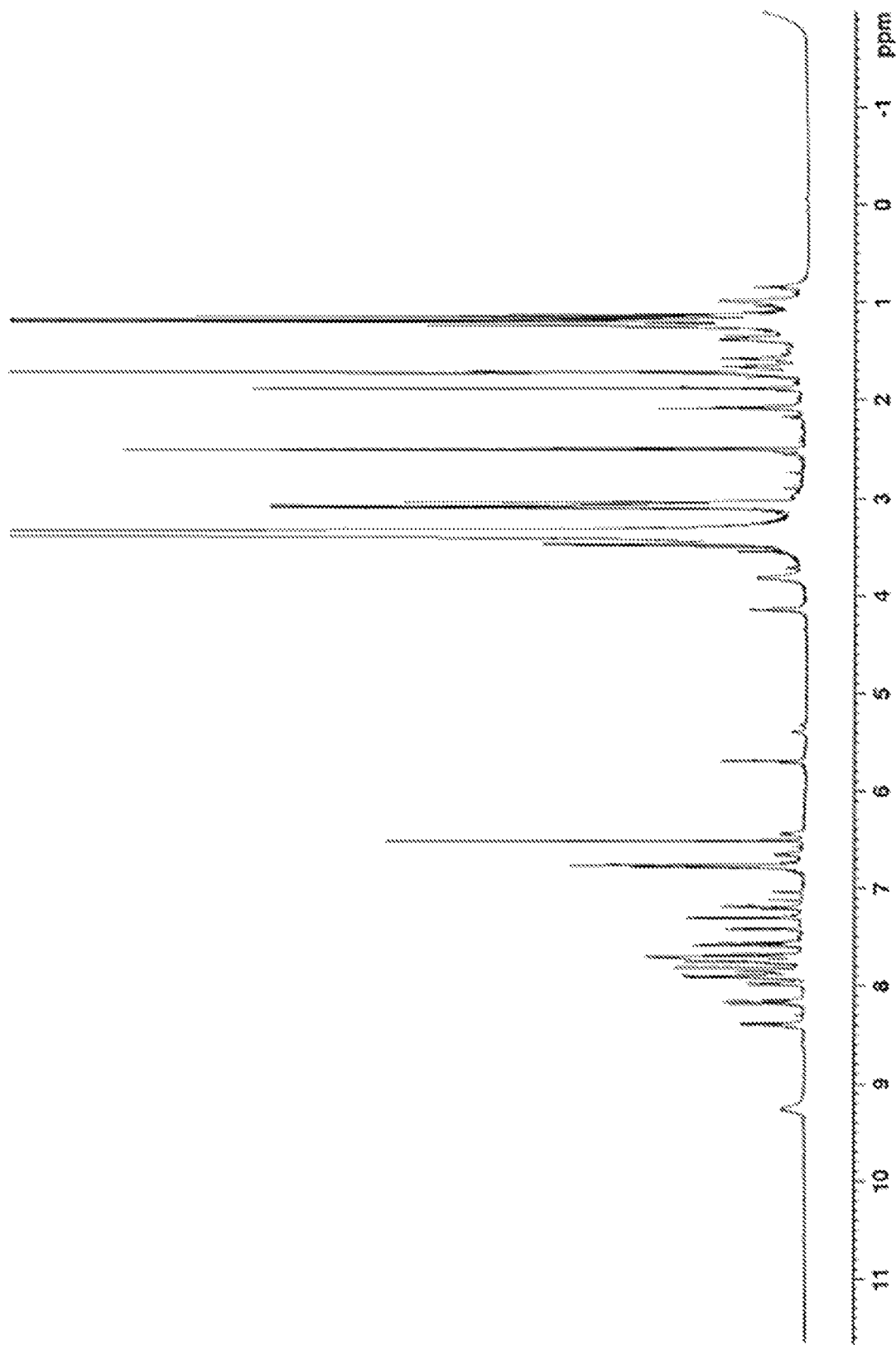
FIG. 15 shows $^1$H-NMR spectra for MI-1.
Figure 16:
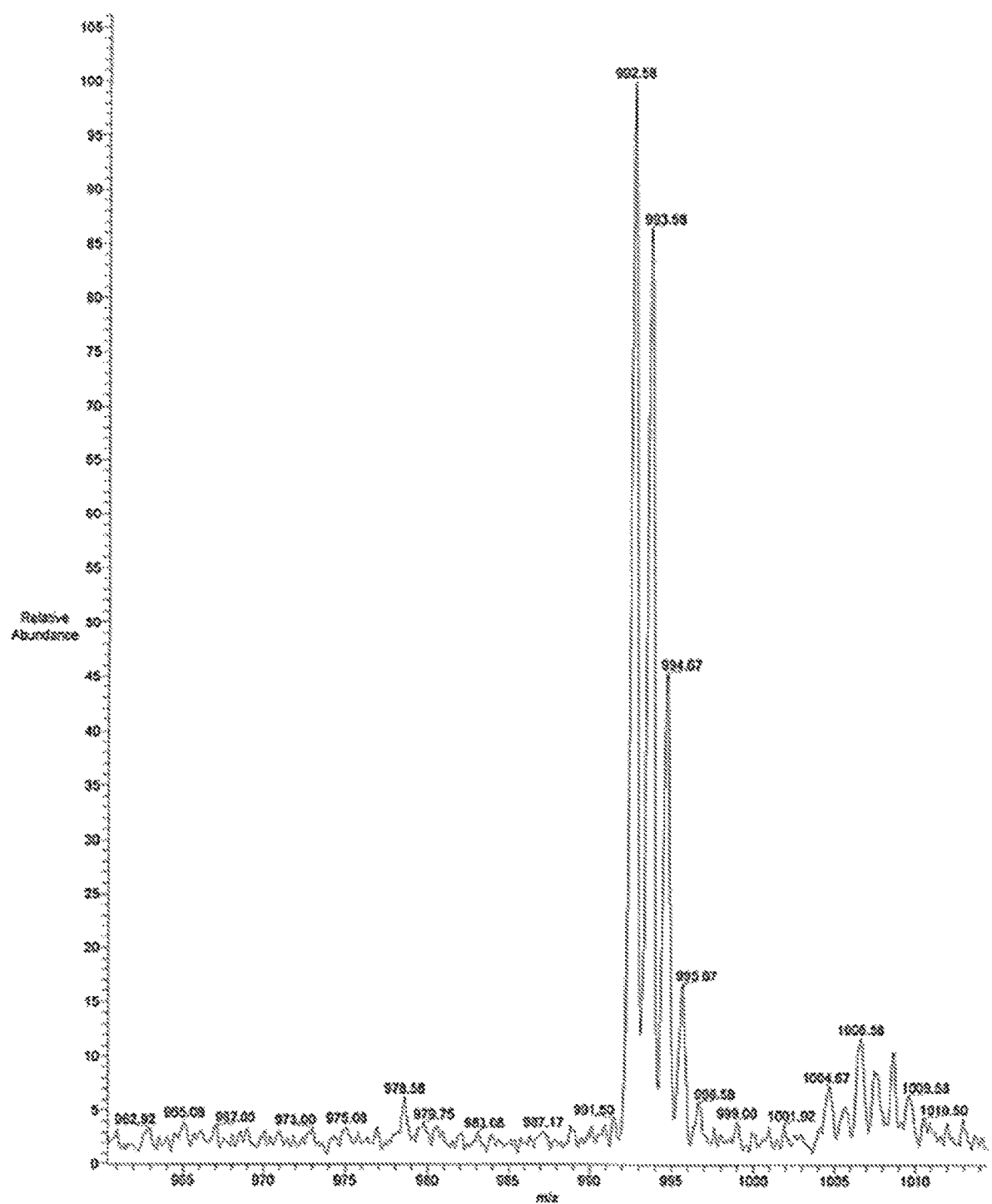
FIG. 16 shows LRMS data for MI-15.
Figure 17:
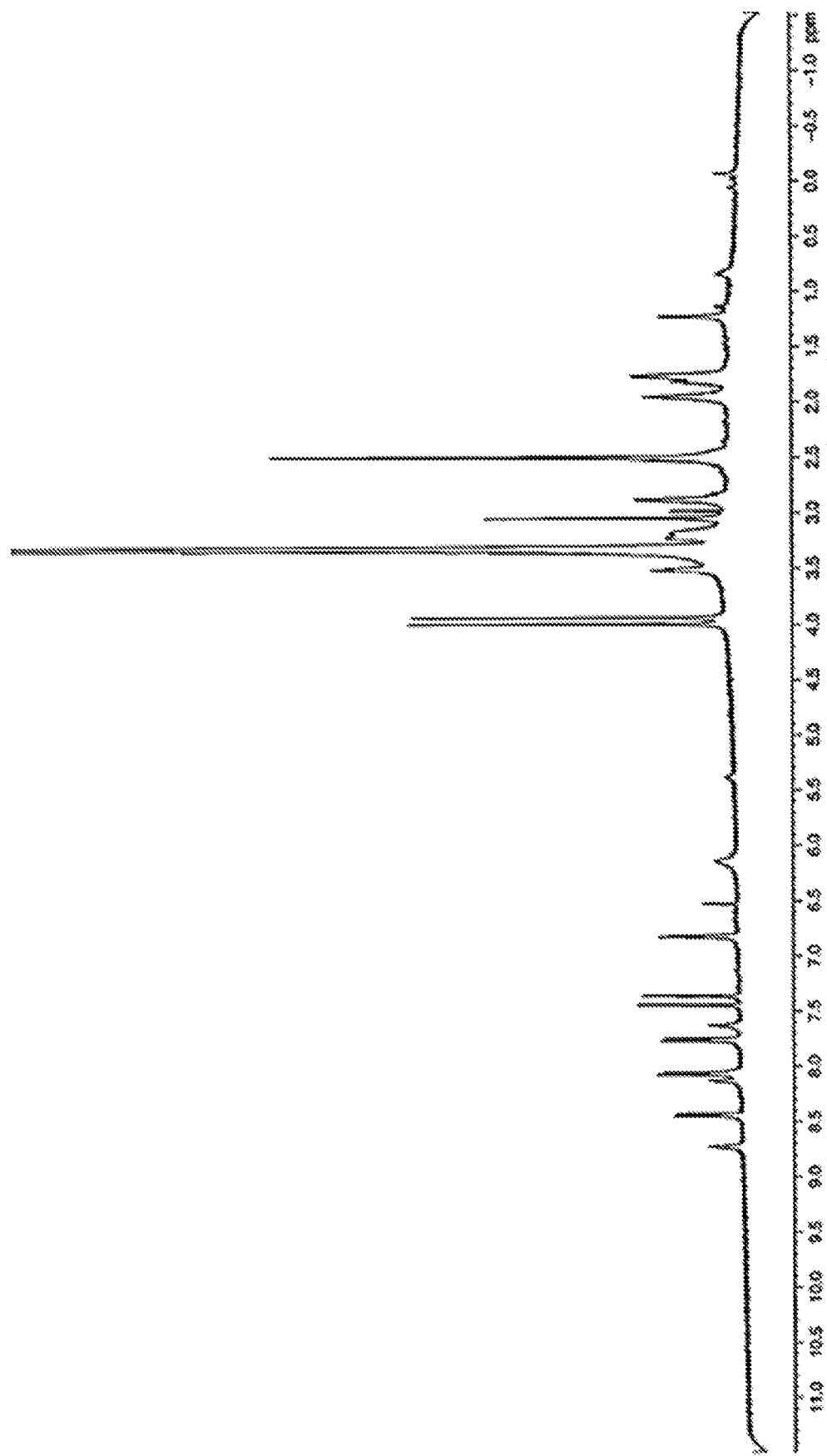
FIG. 17 shows $^1$H-NMR spectra for MI-15.
Figure 18:
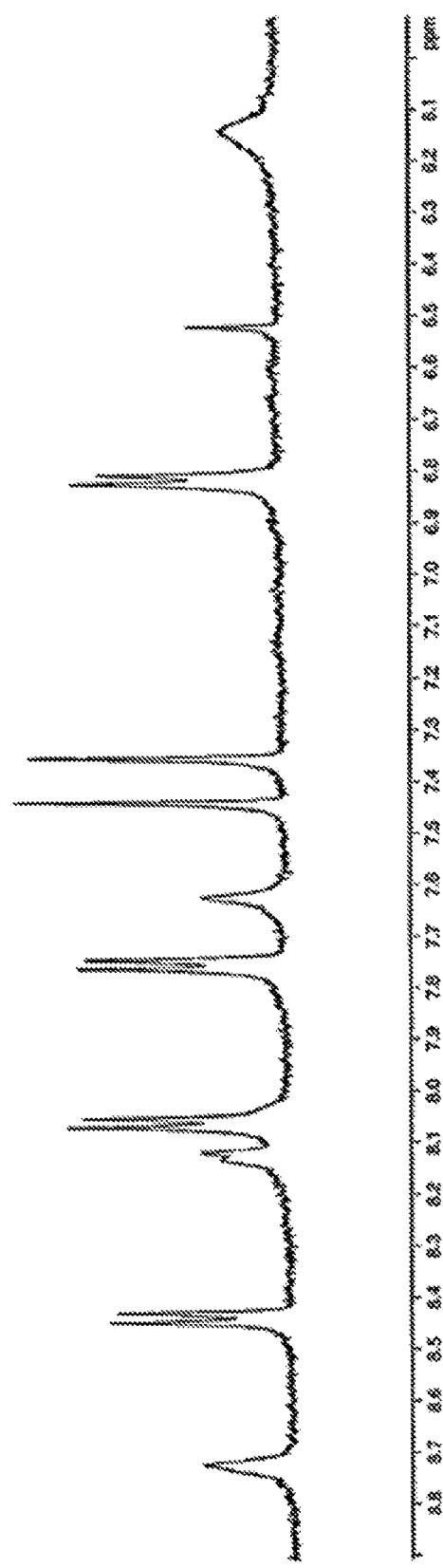
FIG. 18 shows $^1$H-NMR spectra for MI-15.
Figure 19:
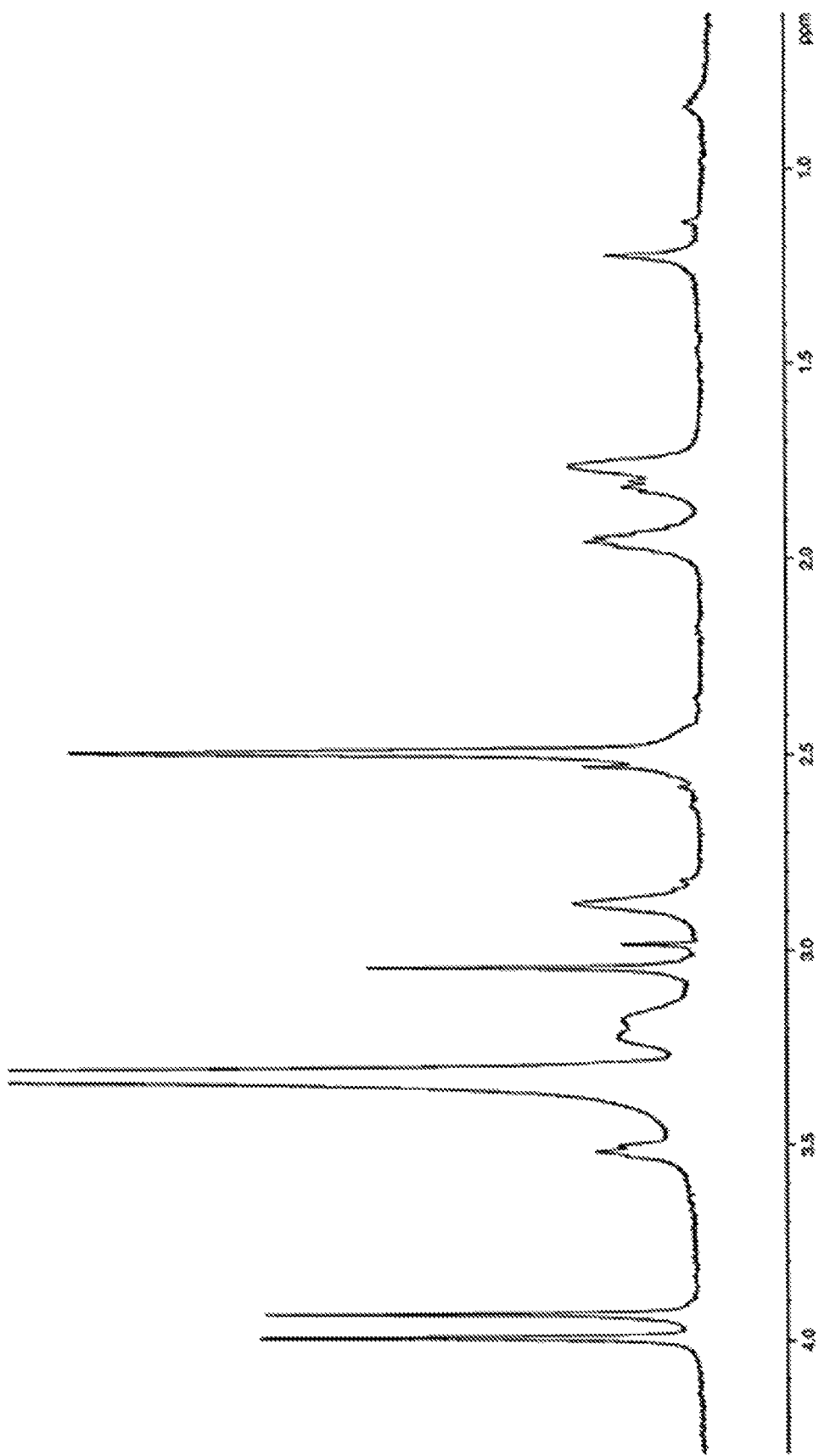
FIG. 19 shows $^1$H-NMR spectra for MI-15.
Figure 20:
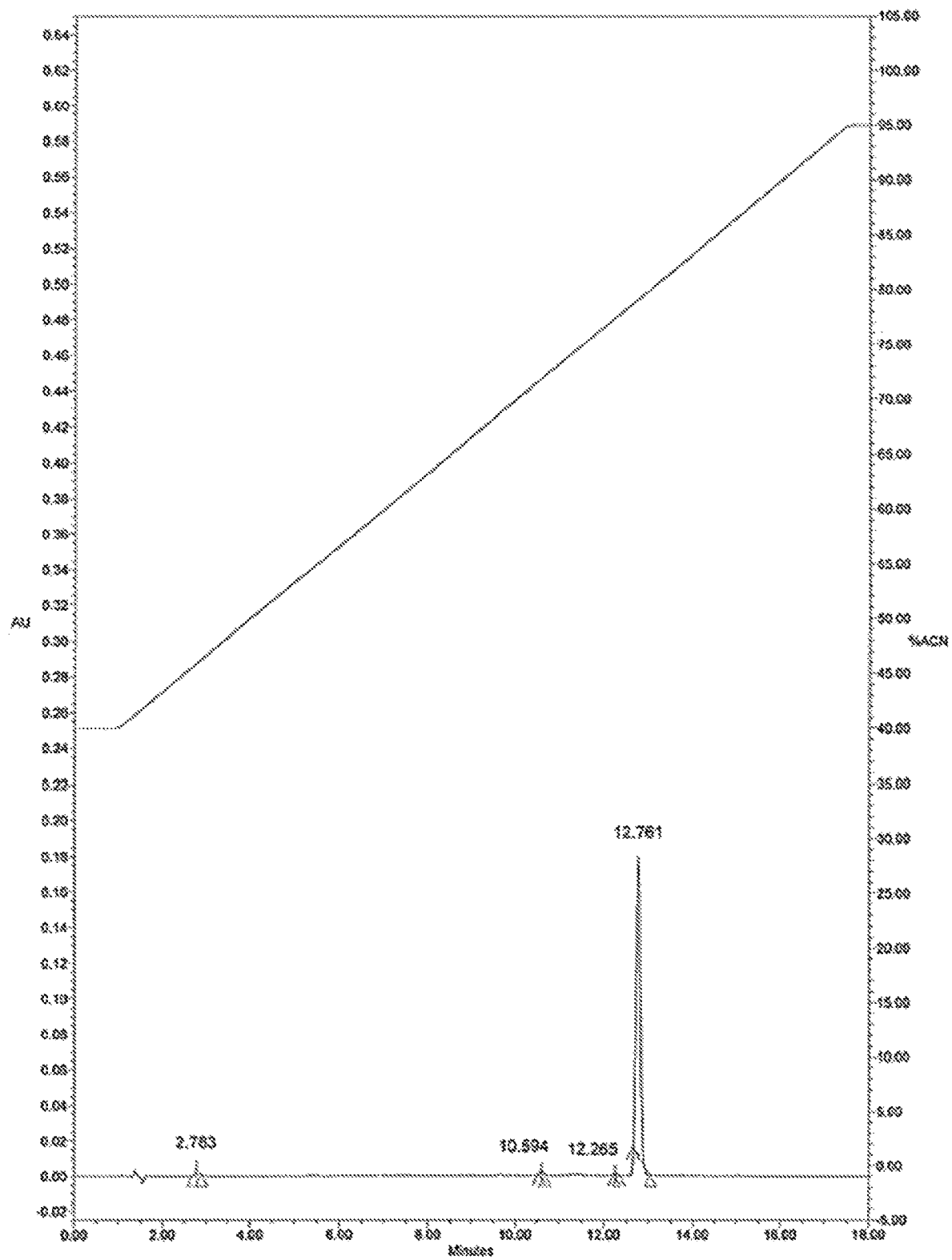
FIG. 20 shows HPLC data for MI-15.

Photophysical characterization from synthesis of the hypoxia sensitive azo-based fluorescence imaging probes recited above is shown in FIGS. 14-20. More specifically, FIGS. 14-15 illustrate ¹H-NMR spectra and LRMS data for MI-1, and FIGS. 16-20 illustrate ¹H-NMR spectra, LRMS, and HPLC data for MI-15.

In some embodiments, the compound is a hypoxia targeted therapeutic agent. Non-limiting examples of the therapeutic agent are below.

Hypoxia Targeted Therapeutic Agents

JU-1023

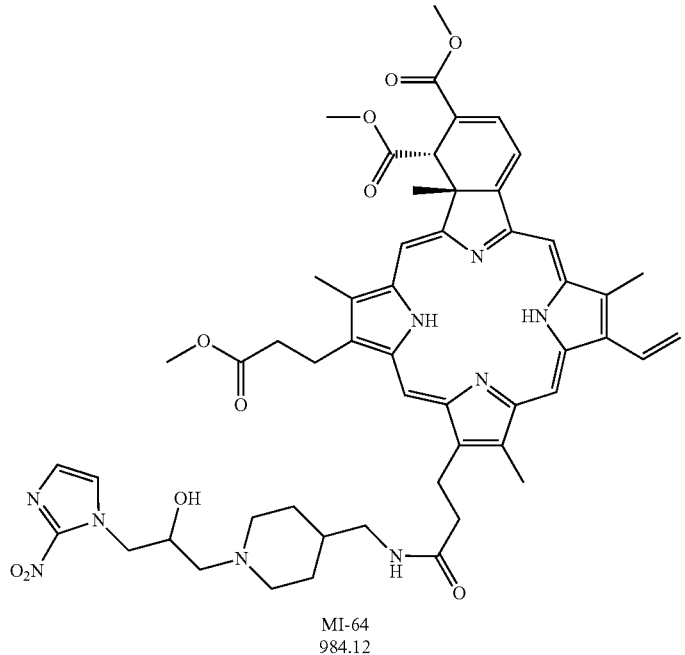

MI-64
984.12

JU-1025

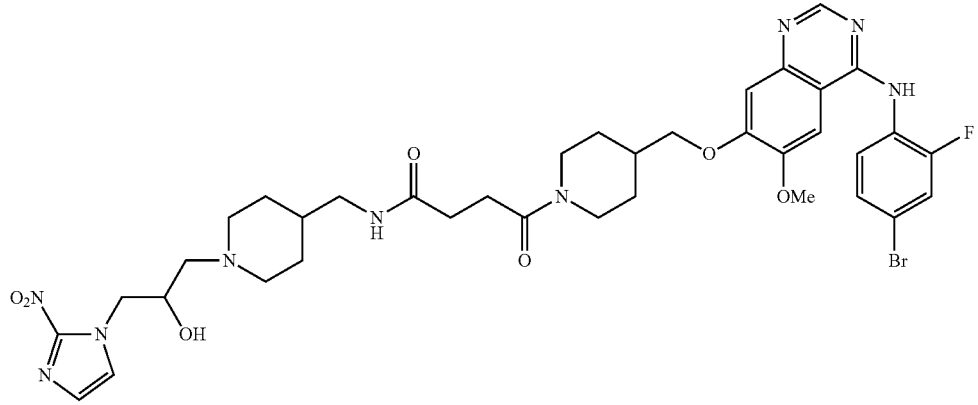

J-946
826.72

JU-1026

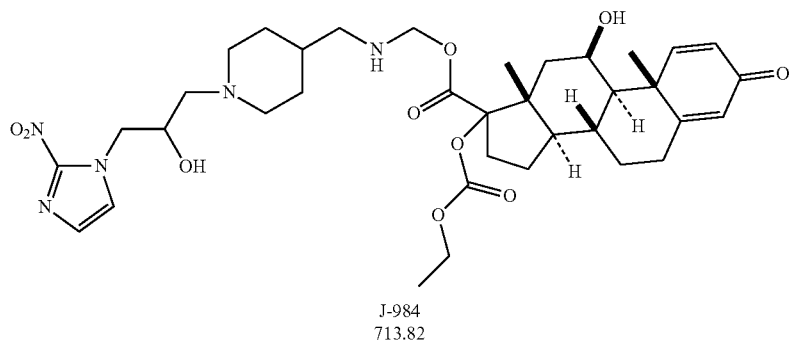

J-984
713.82

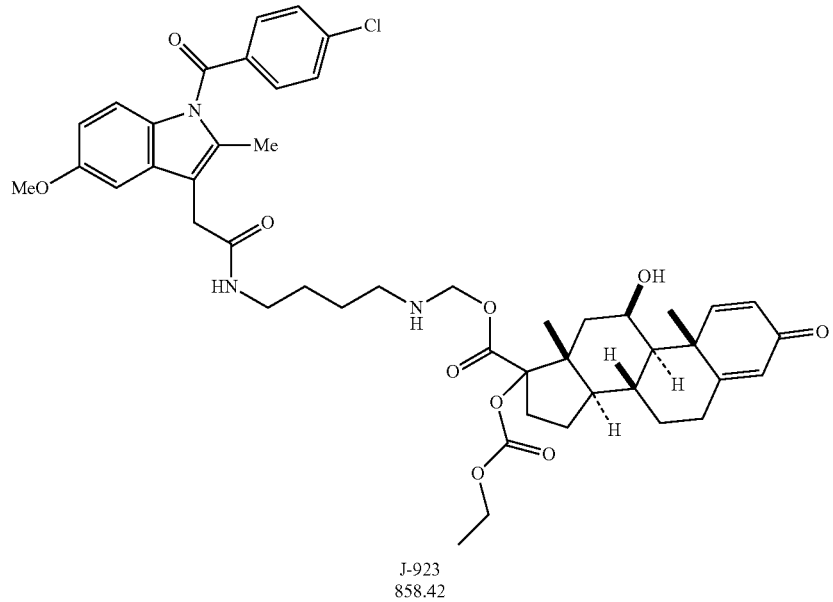

JU-1024

J-923
858.42

Figure 21:
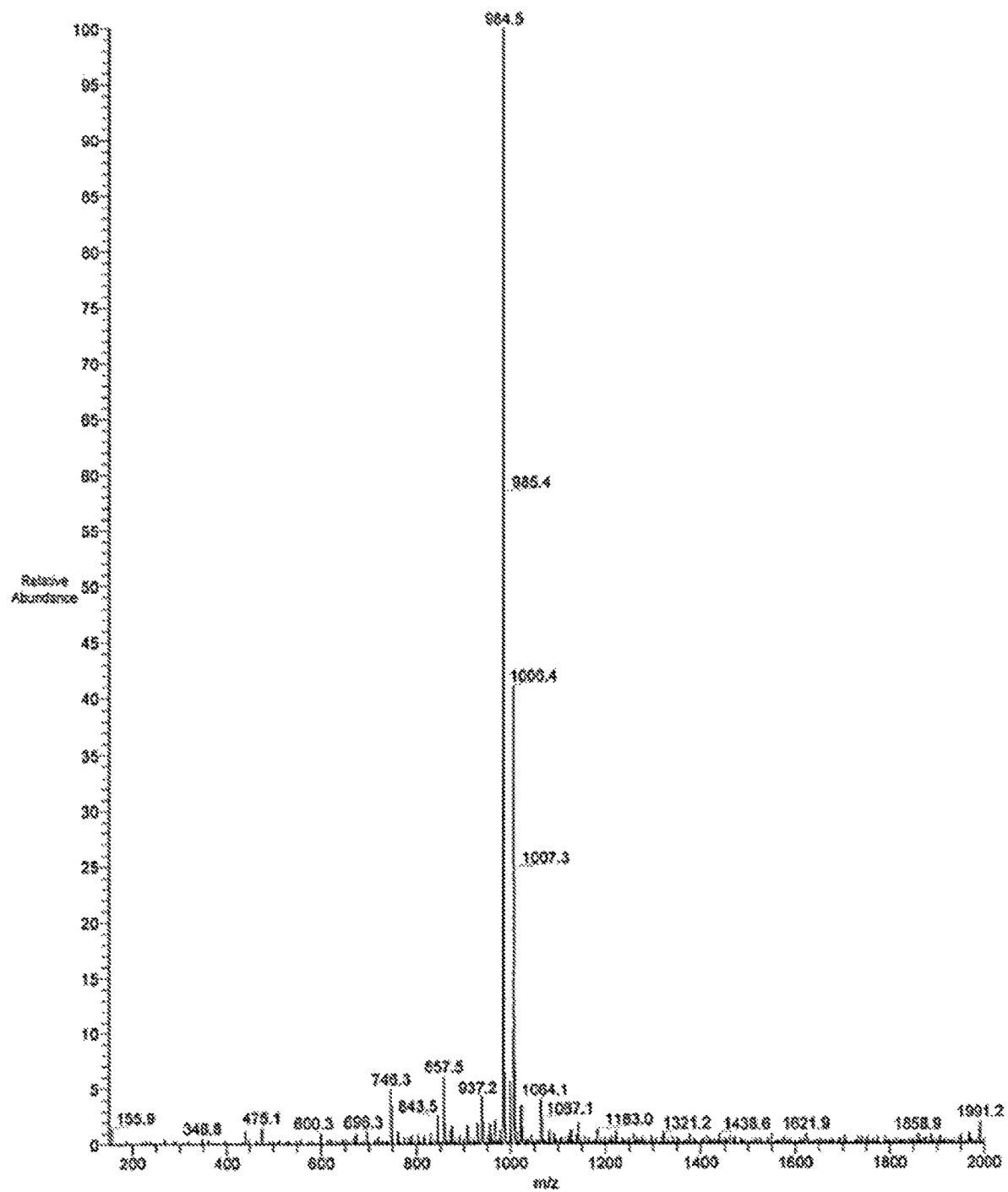
FIG. 21 shows LRMS data for MI-64.

Photophysical characterization from synthesis of one of the hypoxia targeted therapeutic agents recited above is shown in FIG. 21. More specifically, FIG. 21 illustrates LRMS data for MI-64.

In some embodiments, the presently disclosed subject matter provides the design and synthesis of a series of molecular probes that have potential applications to detect hypoxia in mouse models of retinal vascular diseases and treat diseases related to neovascularization. In some embodiments, synthesized hypoxia targeted fluorescence imaging agents are provided.

As described above, in some embodiments, the imaging agents include, but are not limited to, (i) the azo-based fluorescence imaging probes, which features a hypoxia-sensitive cleavable azo-bond, (ii) the 2-nitroimidazole containing fluorescence imaging probes, and/or (iii) the hypoxia sensitive reversible ON-OFF fluorescence imaging probes. In some embodiments, the imaging probes are selectively retained in hypoxia-conditioned retinal cells. In some embodiments, the imaging probes provide dose-dependent fluorescence enhancement relative to normoxic controls. Additionally, in some embodiments, the fluorescence in hypoxic cells and tissues is undetectable under normoxia.

In some embodiments, the imaging agents include activatable probes which are cleaved in hypoxic retinal cell culture and animal models, enabling detection of hypoxia with high signal to noise ratios. For example, in some embodiments, the 2-nitroimidazole containing fluorescence probes are reduced under hypoxia. The reduced probes may then be visualized using fluorescence imaging angiographic equipment, including, but not limited to, in vivo imaging with conventional equipment routinely used for fluorescein angiography. In another example, the reversible on-off probes are highly sensitive to hypoxic tissues and provide detection of hypoxia with high signal to noise ratios.

In contrast to existing imaging probes, such as HYPDX-1, HYPDX-2, and/or HYPDX-3, one or more of the imaging probes described herein include pharmacokinetic properties that facilitate enhanced and/or increased diffusion into capillary free tissue, such as, but not limited to, capillary free retinal tissue. In some embodiments, the enhanced and/or increased diffusion of the imaging probes provides increased bioavailability. The increased diffusions and/or bioavailability increases the quality and/or quantity of the imaging and, in some embodiments, provides imaging of additional tissue as compared to existing probes.

The imaging agents according to one or more of the embodiments disclosed herein are non-toxic, non-invasive, and/or capable of detecting and monitoring retinal hypoxia in living systems. For example, in one embodiment, HYPDX-4 provides non-toxic, non-invasive imaging of retinal hypoxia in preclinical disease models and patients. In some embodiments, the detection and monitoring of retinal hypoxia in living systems facilitates characterization of the role of hypoxia in experimental and human retinal neovascular pathogenesis. For example, in one embodiment, the non-invasive imaging provides information regarding the evolution of hypoxia over time, which is then correlated with biochemical markers and/or morphometric characteristics of retinal neovascular pathogenesis.

Additionally or alternatively, in some embodiments, the non-invasive imaging provides early detection of hypoxia before the onset of any overt neural or vascular anomalies. This early detection of hypoxia may facilitate physician assessment of whether prophylactic therapy is indicated. The hypoxia imaging and quantification may also facilitate gauging the efficacy of therapy on established disease. Although described herein primarily with regard to various retinopathies, as will be appreciated by those skilled in the art, the imaging agents/probes are not so limited and may provide information to elucidate the role of hypoxia in other disease affected tissues.

Furthermore, embodiments of the presently-disclosed subject matter include pharmaceutical compositions comprising the above compound and a pharmaceutically acceptable carrier. The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants and excipients. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like.

Further provided, in some embodiments of the presently disclosed subject matter, is a method of detecting hypoxia in a subject by administering an effective amount of compound to the subject in need thereof. In some embodiments, detecting hypoxia includes detection of hypoxia in age-related macular degeneration (AMD), retinopathy of prematurity (ROP), diabetic retinopathy (DR), and branch retinal vein occlusion (BRVO).

Still further, in some embodiments of the presently disclosed subject matter, is a method of treating hypoxia in a subject by administering an effective amount of the compound to the subject in need thereof. In some embodiments, the hypoxia is retinal hypoxia.

EXAMPLES

The presently-disclosed subject matter is further illustrated by the following specific but non-limiting examples set forth below. The examples may include compilations of data that are representative of data gathered at various times during the course of development and experimentation related to the presently-disclosed subject matter.

Example 1

Purpose: Hypoxia has been associated with initiation and progression of many retinal diseases. Technologies for imaging retinal hypoxia are needed to improve clinical management of these diseases by enabling early detection, monitoring of disease progression, and response to therapy. This example describes the development and characterization of a hypoxia-selective fluorescein based optical imaging probe for detection of retinal hypoxia in several cell culture and animal models using in vivo retinal fluorescence imaging.

Methods: Sensitivity, specificity, and safety of fluorescein-based hypoxia sensitive imaging probes were characterized in R28 rat retinal neuronal cell lines, human Müller cells, and human RPE cells, as well as mouse models of laser-induced choroidal neovascularization (LCNV), retinal vein occlusion (RVO), and oxygen-induced retinopathy (OIR). Cell culture studies included analysis of uptake and toxicity, confocal microscopy uptake studies, and gel electrophoresis/blotting to identify hypoxia probe retention in hypoxic vs. normoxic cell lysates. Animal models were imaged using in vivo retinal fluorescence imaging system and tissues were dissected and stained to confirm probe uptake ex vivo, colocalbation with hypoxic or avascular retinal tissue regions, as well as toxicity (TUNEL, caspase-3 staining).

Results: FIGS. 22A-38 show the result of this study, as described in further detail below. Cells conditioned under hypoxia exhibited dose-dependent fluorescence enhancement due to selective cellular retention of imaging probes. Colocalization with Hypoxyprobe immunostaining and Western blot analysis of imaging probes in lysates further confirmed hypoxia selectivity. In LCNV and OIR animal models, hypoxia imaging probes colocalized with hypoxic regions of tissue identified by immunofluorescence staining. Signal to noise ratios of these imaging probes exceeded 10:1 in several disease models. Imaging probes were well tolerated as indicated by BrdU, TUNEL and Caspase-3 assays.

Conclusion: this example describes a promising in vivo imaging probe for detection of hypoxic retina using noninvasive fluorescence imaging equipment. These probes are biocompatible and sensitive, and complement existing technologies for measuring retinal vascular P02 and blood flow. Furthermore, hypoxia imaging probes described here are readily useful for elucidating the role of hypoxia in retinal disease in preclinical studies.

Example 2

This example describes the synthesis of HYPDX-4 and testing of its ability to discriminate between normoxia and hypoxia in vivo, by hypoxia-induced fluorescence enhancement. As described in detail below, HYPDX-4 was selectively retained in hypoxia-conditioned retinal cell cultures, demonstrating dose-dependent fluorescence enhancement relative to normoxic controls. HYPDX-4-dependent in vivo and ex vivo imaging of hypoxia was tested in mouse models of oxygen-induced retinopathy (OIR) and retinal vein occlusion (RVO); both of which are preclinical models of ischemia-induced retinopathy, with each having retinal hypoxia as a critical pathologic component. Predicted patterns of retinal hypoxia were imaged by HYPDX-4-dependent fluorescence activity in these animal models.

In retinal cells and mice, pimonidazole-adduct immunostaining confirmed the hypoxia selectivity of HYPDX-4. Toxicity testing of HYPDX-4 showed that it had no effect on retinal cell apoptosis and retinal physiology as measured by electroretinography (ERG). Therefore, HYPDX-4 is believed to be capable of serving as the basis for in vivo fluorescence-based hypoxia-imaging techniques, providing a tool for investigators to understand the pathogenesis of ischemic retinopathies and for physicians to address unmet clinical needs.

Materials and Methods

Reagents, Equipment and Cells

Low glucose DMEM, DMEM/F12, Fetal Bovine Serum, GlutaMax, Gentamicin/Amphotericin B and Penicillin-Streptomycin were obtained from GIBCO; Grand Island, N.Y. The human retinal pigment epithelial cell line, ARPE-19 was purchased from ATCC; Manassas, Va. Human Müller cells (MIO-M1) were kindly provided by Dr. G. A. Limb (Moorfields Institute of Ophthalmology, London, UK).[30] The rat retinal neuronal cell line R28 was purchased from KeraFast; Boston, Mass. A humidified cell culture chamber with a ProOx 110 oxygen control device was obtained from BioSpherix Inc.; Parish, N.Y. A Hypoxyprobe immunodetection kit (anti-pimonidazole-adduct antibody) was purchased from Hypoxyprobe Inc.; Burlington, Mass. The secondary anti-rabbit IgG conjugated to Alexa Fluor 647 (AF647) and prolong gold mounting media with DAPI and Alexa Fluor 488 or 647 conjugated isolectin B4 were purchased from Life Technologies, Grand Island, N.Y.

Mice

C57BL/6J female mice 4-6 weeks of age were purchased from Charles River Laboratories; Chicago, Ill. All animal procedures used in this study were approved by the Vanderbilt University Institutional Animal Care and Use Committee and were performed in accordance with the ARVO Statement for the Use of Animals in Ophthalmic and Vision Research.

Imaging of Retinal Hypoxia in the Mouse OIR

Mouse pups and their dams were placed in 75% oxygen from P7 to P12 according to the OIR oxygen treatment protocol.[27] On P12, litters were removed to room air and after 2 hours, HYPDX-4 (60 mg/kg in PBS) was administered by intraperitoneal injection. Twenty-four hours post-injection, in vivo HYPDX-4-dependent fluorescence imaging was performed. Briefly, mice were anesthetized with ketamine/xylazine, eyes were dilated with 1% tropicamide and placed on a warm platform, and fluorescent and bright field fundus images were acquired using the Micron IV retinal-imaging system (Phoenix Research Laboratories; Pleasanton, Calif.). Then, ex vivo imaging of HYPDX-4 dependent fluorescence was performed. The mice were sacrificed, enucleated, and the globes were fixed in 10% neutral buffered formalin (NBF). Retinas were dissected and stained directly with Alexa Fluor 647-conjugated isolectin B4 then flat-mounted on a microscope slide with Prolong Gold mounting medium (Life Technologies, Grand Island, N.Y.). Images were captured using an epifluorescence 'Nikon Eclipse Ti-E' inverted microscope (Melville, N.Y.).

Some mice received intraperitoneal injections of pimonidazole hydrochloride at a concentration of 60 mg/kg body weight two hours after removal to the room air; they were sacrificed and enucleated one hour later. The globes were fixed in 10% NBF for 2 hours; retinas were dissected and washed with tris-buffered saline (TBS), then they were blocked/permeabilized in 10% donkey serum with 1% Triton X-100/0.05% Tween 20 in TBS for 6 hours, and stained with an antibody against pimonidazole-adducts followed by the secondary anti-rabbit IgG conjugated to Alexa Fluor 647- and Alexa Fluor 488-conjugated isolectin B4. The retinas were mounted on microscope slides with Prolong Gold mounting medium. Ex vivo images were captured using an epifluorescence 'Nikon Eclipse Ti-E' inverted microscope.

Imaging of Retinal Hypoxia in RVO Animal Model

Laser-induced retinal vein occlusion was performed as previously described.[31] Briefly, C57BL/6 female mice were anesthetized by intraperitoneal injection of ketamine/xylazine and the eyes were dilated using 1% tropicamide. A phosphate buffered solution of 39.31 mM rose bengal (4,5,6,7-tetrachloro-2',4',5',7'-tetraiodo-fluorescein disodium salt, certified purity, 95%; Sigma, St. Louis, Mo.) was sterilized by passage through a 0.22-μm filter, and tail vein injected at a dose of 40 mg/kg. An argon laser photocoagulator (green light) mounted on a slit-lamp (Space Coast Laser Inc. Palm Bay, Fla.) was used to create retinal vein-occlusion (50-μm spot size, 1-second duration, 50 mW). Three laser applications were required to completely stop the blood flow as determined by observing the fundus image with a slit-lamp microscope. In each fundus, only one or two veins was/were photocoagulated to create retinal ischemia. Two hours post-RVO, mice were divided into two groups and received intraperitoneal injection of the HYPDX-4 (60 mg/kg body weight) or pimonidazole hydrochloride (60 mg/kg body weight). Twenty-two hours post-injection of HYPDX-4, in vivo HYPDX-4 dependent fluorescence imaging was performed. The mice were anesthetized with ketamine/xylazine, dilated with 1% tropicamide, and placed on a warm platform; TRITC-Dextran 500 (Sigma, St. Louis, Mo.) was injected systemically at a dose of 20 mg/kg; and fluorescent and bright field fundus images were acquired using the Micron IV retinal-imaging system. Mice were sacrificed, enucleated and the globes were fixed in 10% NBF. HYPDX-4-dependent fluorescence was imaged ex vivo as previously described in the OIR section. For the pimonidazole hydrochloride-injected group, the animals were sacrificed one hour after injection, enucleated and the globes were fixed in 10% NBF. The retinas were processes and ex vivo images were captured as described above for mouse OIR.

Retinal Cell Culture

ARPE-19 cells were cultured in DMEM/F12 supplemented with 10% Fetal Bovine Serum, 1× GlutaMAX, and 1× Gentamicin/Amphotericin B. MIO-M1 and R28 cells were cultured in low glucose DMEM supplemented with 10% Fetal Bovine Serum, 1× GlutaMAX, and 1× Penicillin-Streptomycin. Cells were maintained in a humidified environment with 5% $CO_2$ at 37° C. unless otherwise noted. The cells were cultured in 96 microwell plates, with HYPDX-4 concentrations ranging from 10 to 100 μM in complete medium, or 100 μM pimonidazole hydrochloride in complete medium. To establish a hypoxic environment, the cells were placed into a humidified hypoxic chamber and flushed with a mixture of 95% $N_2$ and 5% $CO_2$, at a flow rate of 20 L/min for 5 min according to manufacturer instructions. The chamber was clamped and placed at 37° C. for the duration of the treatment. The oxygen level was monitored using the Traceable™ Dissolved Oxygen Meter Pen (Fisher Scientific; Pittsburg, Pa.). To confirm induction of hypoxia, cells were treated with 100 μM pimonidazole hydrochloride diluted in complete medium, subjected to hypoxia or normoxia for 4 hours and immunostained for pimonidazole-adducts according to manufacturer's protocol.

In Vitro Hypoxia-Induced, HYPDX-4-Dependent Fluorescence Assay

ARPE-19, MIO-M1 were seeded at 20,000 and R28 at 15,000 cells per well, respectively, in a 96-well black plate with a clear bottom. When cells were 80% confluent, they were treated with 100 μM HYPDX-4 unless otherwise specified, in complete medium and cultured in normoxia or hypoxia for 4 hours. The cells were washed with pre-warmed Hank's Buffered Salt Solution (HBSS). Fluorescence intensity was measured (Absorbance: 490 nm, Emission: 520 nm) using a microplate reader (Biotek; Winooski, Vt.).

In Vitro Imaging of R28 Cells Using HYPDX-4

R28 cells were seeded at a density of 45,000 cells per well in 3 wells of 4-well chamber slides. When cells were 90% confluent, 2 wells were treated with HYPDX-4 in complete medium, and one well was treated with pimonidazole hydrochloride diluted in complete medium. The cells were cultured in hypoxia or normoxia for 4 hours. Cells were washed 3 times with HBSS, fixed with 10% neutral buffered formalin (NBF) for 10 minutes at room temperature, washed 3 times with TBS and mounted with Prolong Gold with DAPI mounting media. Pimonidazole-adducts were immunostained according to manufacturer's protocol. HYPDX-4 dependent fluorescence images were taken using an epifluorescence microscope.

Electroretinography (ERG) Measurements

ERG measurements were performed according to previously published methods.[32,33] Briefly, ERG analysis was performed on mice injected with HYPDX-4 (100 mg/kg) at one week post-injection. Animals were dark adapted overnight, anesthetized with ketamine/xylazine, dilated with 1% tropicamide, and placed on a warm platform within the Ganzfeld dome of a Diagnosys LLC Espion Electrophysiology system (Lowell, Mass., USA). Mice were exposed to flashes of light ranging from −4 to 2 log cd·s/m$^2$ and the amplitudes of a-wave and b-wave were measured from baseline to peak. The amplitude of the a-wave and b-wave were plotted as a function of luminance.

TUNEL Assay

TUNEL assays were performed using Click-iT in situ apoptosis detection kit (Life Technology, USA). The mouse eyes were enucleated and fixed by immersing in 10% NBF for 25 minutes at 4° C. Then, they were fresh frozen in 30% sucrose and embedded in TissueTec OCT for cryosectioning (7 μm sections). The retinal cross-sections were then stained for fragmented DNA by incorporating alkyne-modified EdUTP nucleotide followed by detection with Alexafluor 647 azide in apoptotic cells. Retinal cross-sections were treated with DNase I as the positive control.

Cell Viability Assays

Retinal cell-lines were treated with HYPDX-4 (100 μM) and the viability was measured using the bromodeoxyUridine (BrdU) incorporation assay according to the manufacturers protocol. Briefly, retinal cells were seeded in a 96-well plate for twenty four hours and serum starved for 6 hours. Then, cells were treated with HYPDX-4 and vehicle controls diluted in complete media and allowed to incubate for 24 h. Four hours prior to the end of the incubation, BrdU was added at a concentration of 10 μM and incorporation of BrdU was quantified by ELISA with the BrdU cell viability ELISA kit (Exalpha Biologicals; Shirley, Mass.).

Statistics

Data are presented as mean±SD. Student's t tests were performed to compare 2 samples and, for comparison of more than 2 samples, one-way ANOVA was performed using Prism 6 (Graph-Pad, San Diego, Calif.). p≤0.05 was considered as statistically significant.

General Chemistry Techniques

All chemicals were purchased and used as received unless otherwise indicated. Oregon-Green was obtained from Life Tech (USA) and the nitroimidazole-analog was synthesized according to a modified literature procedure.[34,35] Moisture sensitive reactions were performed in oven-dried glassware under a positive pressure of nitrogen or argon. Air and moisture-sensitive compounds were introduced via syringe or cannula through a rubber septum. HPLC grade solvents were obtained from Fisher Scientific (Pittsburgh, Pa.). All reagents and deuterated solvents were purchased from the Aldrich Chemical Company (Milwaukee, Wis.) and used without further purification. The Oregon Green 488 carboxylic acid succinimidyl ester, 5-isomer was purchased from Life Technologies (grand Island, N.Y.) and used without further purification.

Chromatography

Silica gel column chromatography was performed using Sorbent silica gel standard grad, porosity 60 Å, particle size 32-63 (μm) (230×450 mesh), surface area 500-600 m$^2$/g, bulk density 0.4 g/mL, pH range 6.5-7.5, purchased from Sorbent Technologies (Atlanta, Ga.). The analytical HPLC of the fluorescence compounds were performed on a Waters 2996 HPLC system with a UV or fluorescence detector using C18 reverse-phase columns. HYPDX-4 compound used for biological assays was ≥95% purity based on analytical HPLC monitored at 490 nm.

Synthesis of HYPDX-4

To a stirred solution of Pimonidazole amine hydrochloride (28.2 μmol) in dimethylsulfoxide (2 mL) was added triethylamine (0.1 μmol) to generate the free amine. After stirring for 5 min, the N-succinimidyl ester compound (15.7 μmol) was added and stirred for overnight at 25° C. The solvent was removed by lyophyllization to give the crude product, which was purified by silica gel column chromatography. The synthetic scheme and related photophysical characterization for HYPDX-4 is illustrated in FIGS. 1-3 and 36-38.

Orange solid (75%). $^1$H-NMR (400 MHz, DMSO-d$_6$) δ 10.86 (bs, 1H), 9.68 (bs, 1H), 8.94 (t, J=5.8 Hz, 1H), 8.46 (s, 1H), 8.26 (m, 1H), 7.63 (m, 1H), 7.40 (d, J=8.0 Hz, 1H), 7.19 (m, 1H), 6.93 (m, 2H), 6.53 (m, 2H), 4.57 (dd, J=17.2, 7.4 Hz, 1H), 4.38 (m, 2H), 3.60-3.49 (m, 4H), 3.23-3.21 (m, 2H), 3.18-3.15 (m, 1H), 3.08-2.89 (m, 2H), 1.89-1.83 (m, 2H, 1.67-1.59 (m, 1H, 1.55-1.49 (m, 1H); $^{19}$F-NMR (282 MHz, DMSO-d$_6$) δ −139.9; Mass (ESI−) calculated for $C_{33}H_{28}F_2N_5O_9$ [M-H]: 676.6; found: 676.4.

Determination of Octanol-Water Coefficient of HYPDX-4

A mixture of Octanol (500 uL) and water (500 uL) was added to HYPDX-4 (173 μg), or Pimonidazole Free base (742 μg) or Pimonidazole HCl (1 mL, 50 mg/mL) in an eppendorf tube and gently mixed in a rotator for 2 days. The aqueous and octanol layers were separated and the Optical Density (OD) was measured in microplate spectrophotometer instrument. The amount of HYPDX-4, Pimonidazole Free base and Pimonidazole HCl was calculated from the standard curve.

TABLE 1

Solubility of HYPOX-4. The octanol-water coefficient of HYPOX-4, Pimonidazole HCl and Pimonidazole Free Base were compared.

| Compounds | LogP |
| --- | --- |
| Pimonidazole HCl | −2.06 |
| Pimonidazole free base | +0.74 |
| HYPOX-4 | −2.58 |

Results

In Vitro Hypoxia-Induced HYPDX-4 Fluorescence Activity

Figure 22A:
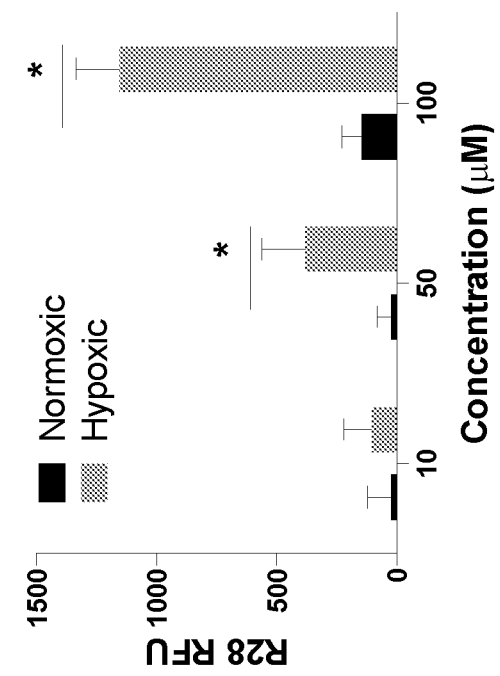
FIGS. 22A-D are graphs showing sensitivity and hypoxia-specificity of HYPDX-4 in retinal cells. Specifically
Figure 22B:
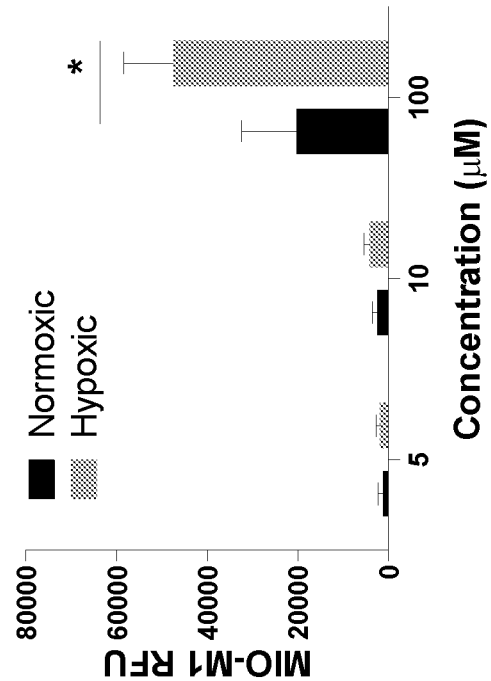
Figure 22C:
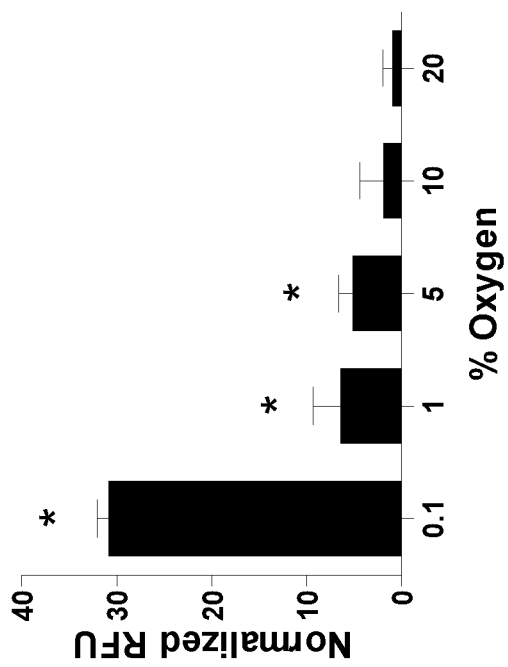
Figure 22D:
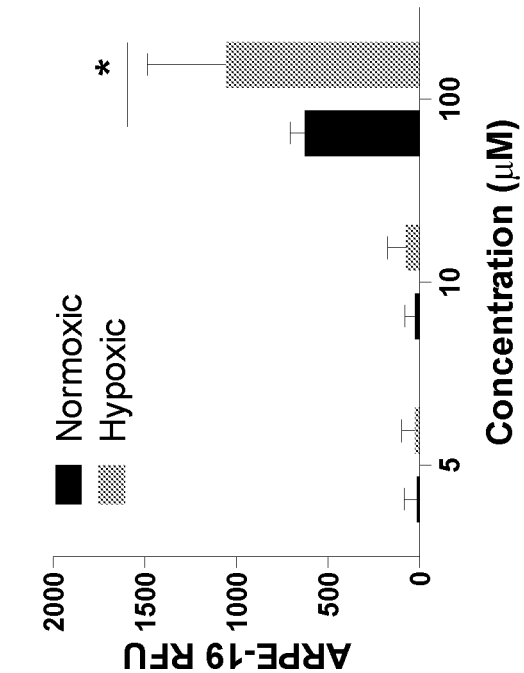
Figure 23B:
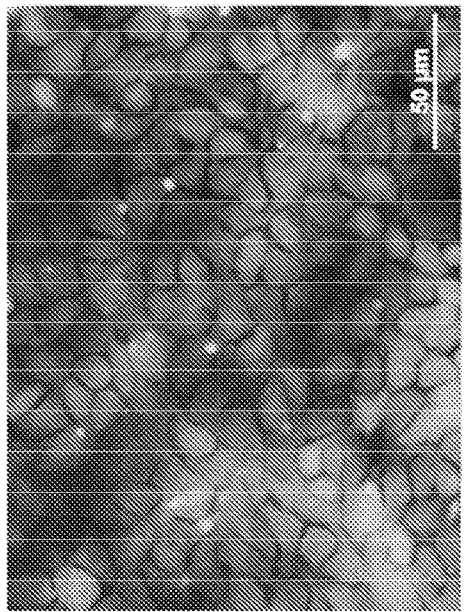
FIGS. 23A-D show dose-dependent fluorescence of HYPDX-4 in various cell types. Hypoxia-specific fluorescence cell imaging was achieved. Minimal fluorescence was observed in normoxic cells (n=8, *p<0.05). Specifically.
Figure 23D:
Figure 23A:
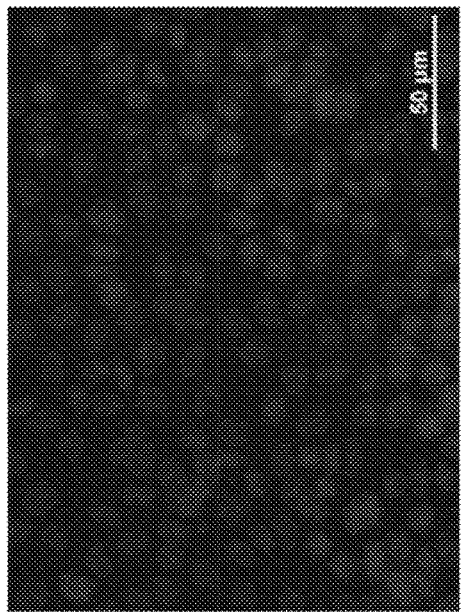
Figure 23C:
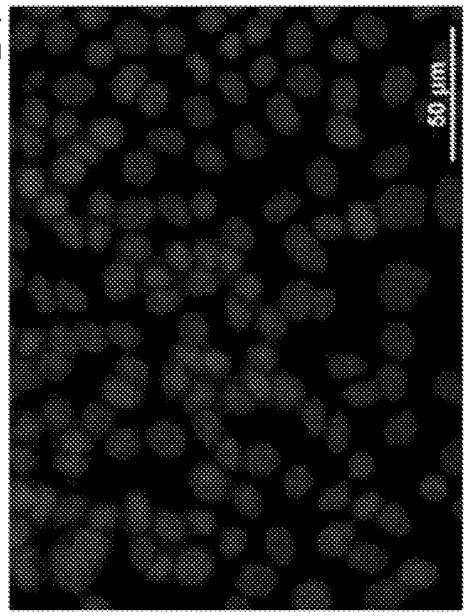
Figure 24A:
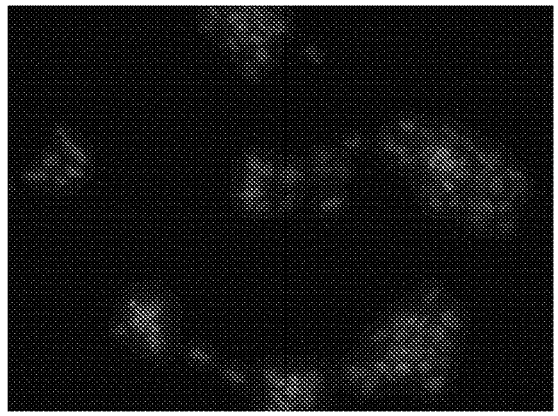
FIGS. 24A-F show pimonidazole-adduct immunodetection of hypoxia in human Müller cells (MIO-M1). Significant fluorescence enhancement was observed in the hypoxic cells incubated with Pimonidazole hydrochloride (100 μM) for 4 hours. Normoxic cells showed minimal fluorescence signal after same treatment. Specifically.
Figure 24B:
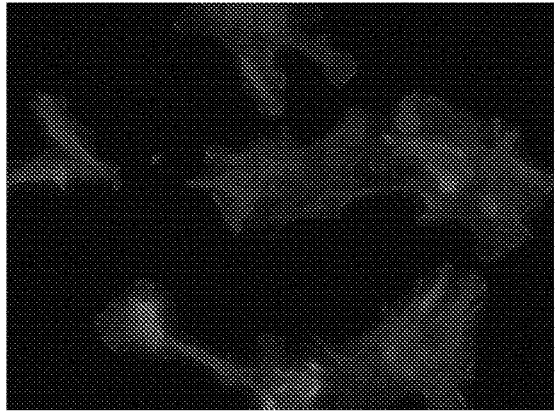
Figure 24C:
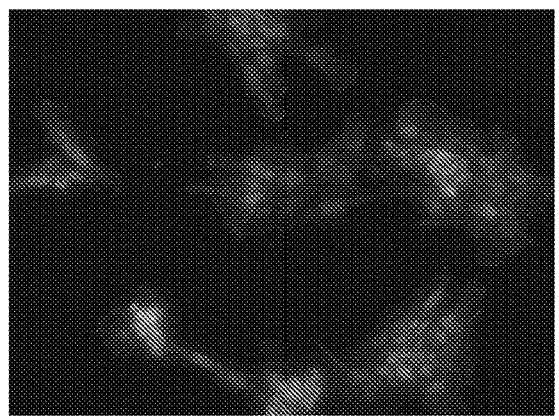
Figure 24D:
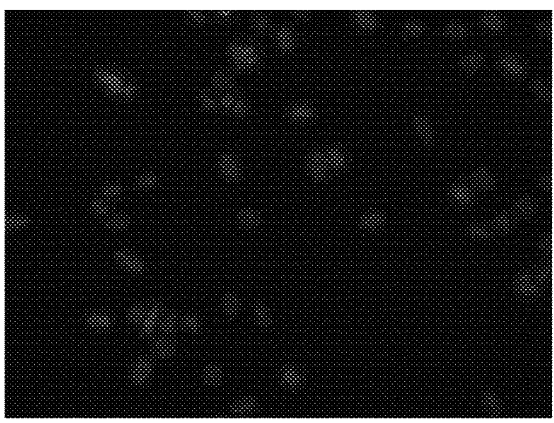
Figure 24E:
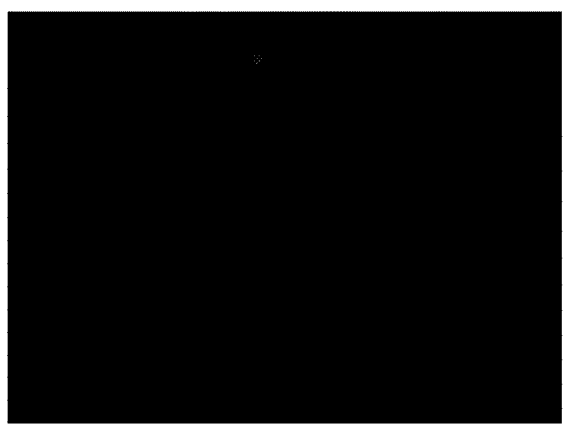
Figure 24F:
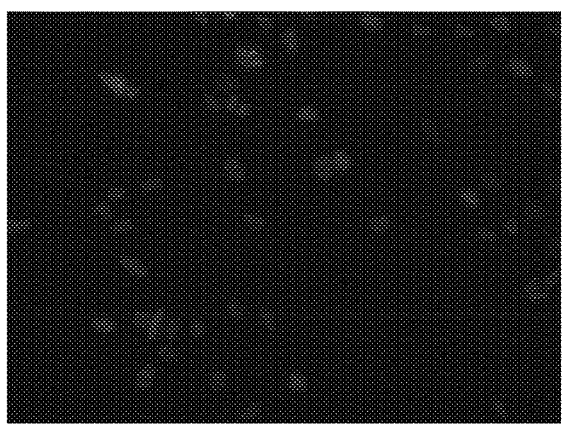
Figure 25A:
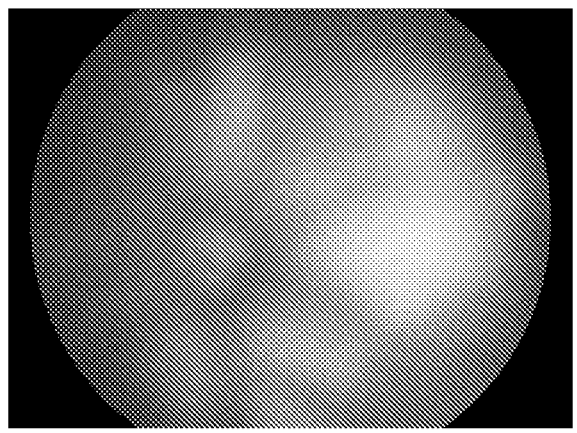
FIGS. 25A-D show In vivo imaging of retinal hypoxia in mouse OIR (P13) and age matched room air (RA) pups. HYPDX-4 was administered systemically to OIR mouse pups 2 hours after return to room air on P12, as well as to age-matched room air pups. In vivo imaging was performed 24 hours post-injection of HYPDX-4.
Figure 25B:
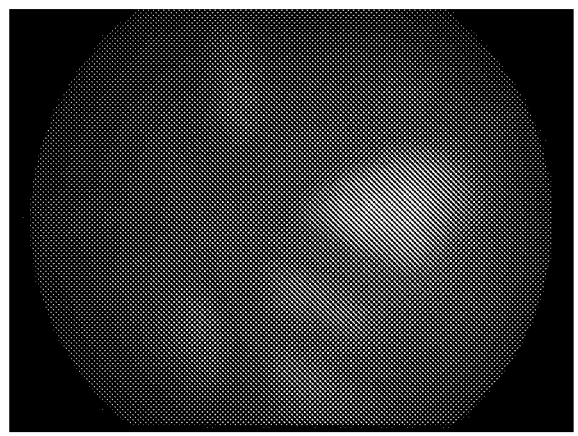
Figure 25C:
Figure 25D:
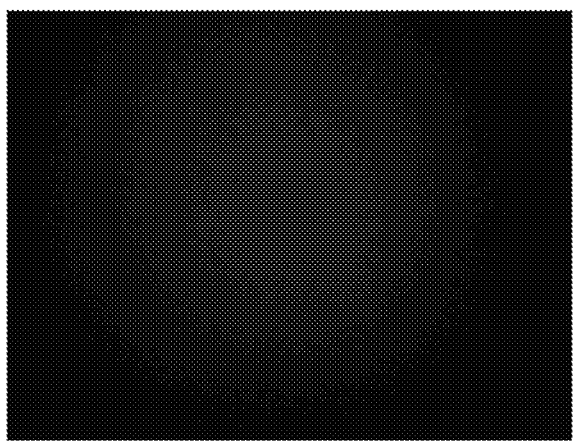
Figure 26A:
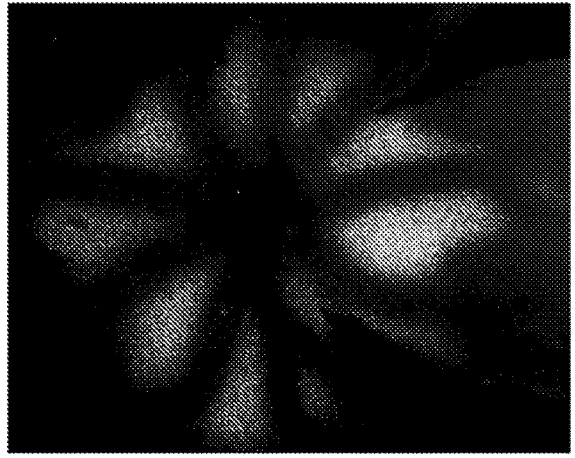
FIGS. 26A-D show ex vivo imaging of mouse retina. Specifically.
Figure 26B:
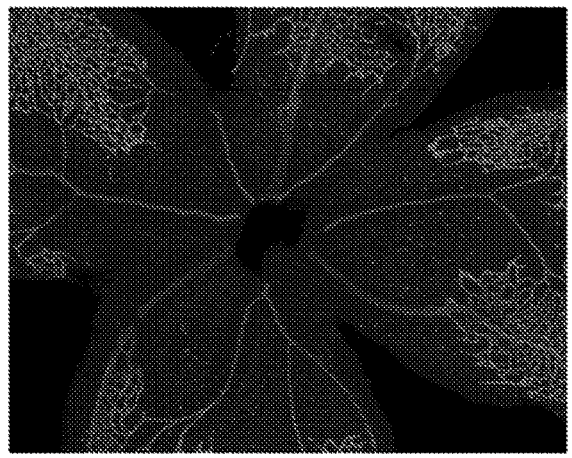
Figure 26C:
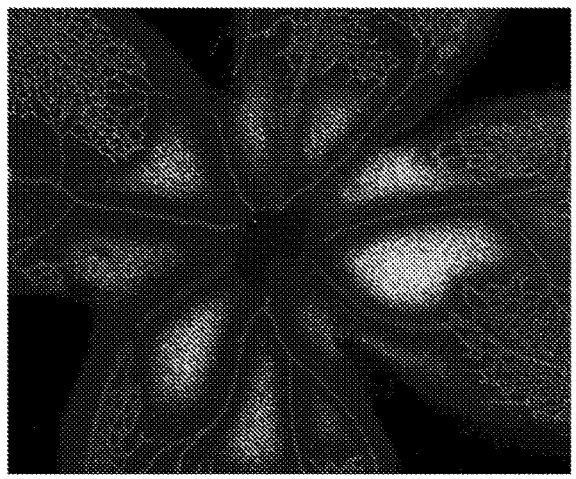
Figure 26D:
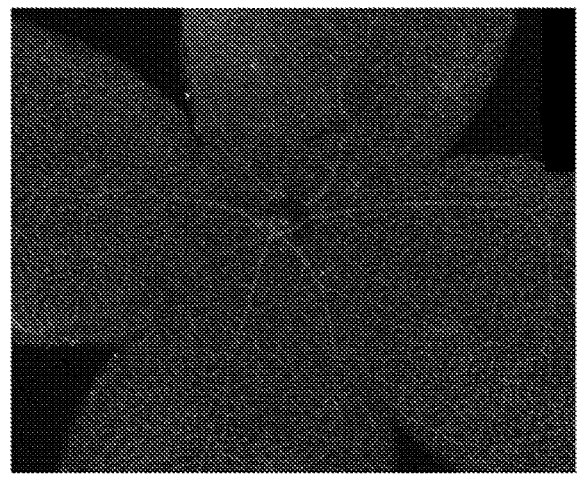

Cultures of rat retinal neuronal cells (R28) were treated with 100 μM HYPDX-4 and exposed to variable oxygen concentrations ranging from 0.1% to 20.9% for 4 hours. HYPDX-4-dependent fluorescence was maximal at 0.1% oxygen (FIG. 22A). Next, using R28 cells (FIG. 22B), retinal pigment epithelial cells (ARPE-19, FIG. 22C) and human Müller cells (MIO-M1, FIG. 22D), the oxygen concentration was maintained at 0.1% and the HYPDX-4 concentration was varied from 10 μM to 100 μM. HYPDX-4 dependent fluorescence was observed with an optimal signal to noise ratios at the 100 μM dose for all cell types. Finally, in vitro cellular imaging was performed using R28 cells. Hypoxia-specific, HYPDX-4-dependent fluorescence activity facilitated hypoxia imaging in this cell-line, as shown in FIGS. 23A-B. Minimal HYPDX-4-dependent fluorescence was observed in normoxic cells (FIGS. 23C-D). Hypoxia was confirmed in these cell lines by immunostaining pimonidazole-adducts (FIGS. 24-A-F).[24] All in vitro experiments were replicated a minimum of three times. Where appropriate, results were statistically evaluated by ANOVA.

In Vivo Imaging of Retinal Hypoxia in the Mouse Model of Oxygen Induced Retinopathy (OIR)

Figure 27:
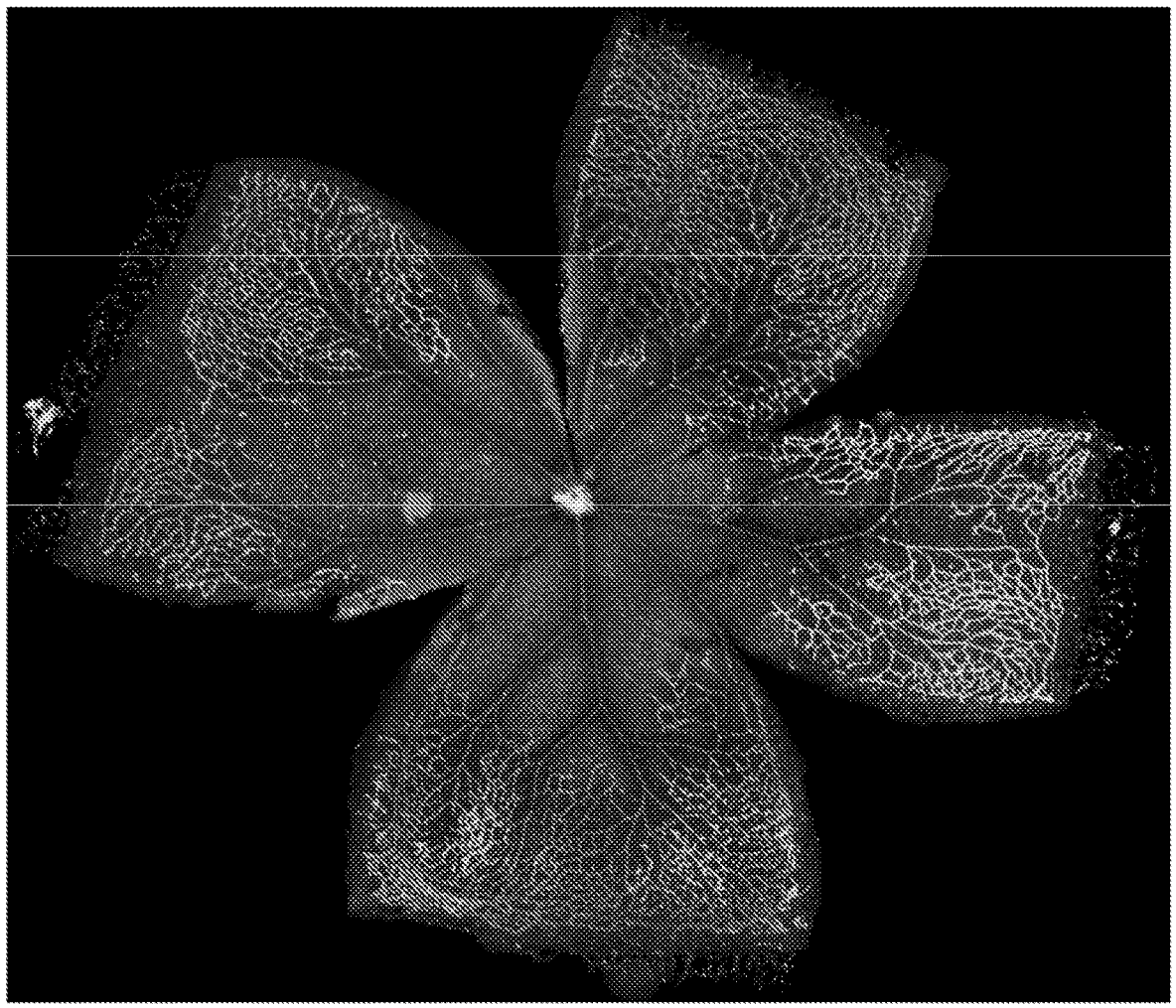
FIG. 27 shows confirmation of hypoxia in OIR (P12) pups by immunostaining of pimonidazole-adducts (red); blood vessels were counterstained with IB4 (green).

In vivo imaging of retinal hypoxia was performed in OIR mice.[21] HYPDX-4 was administered post-oxygen exposure by intraperitoneal injection 2 hours after mice were returned from exposure chambers to room air (P12); age-matched room air (RA) control pups were similarly treated. In vivo fluorescence imaging was performed 24 hours post HYPDX-4 injection. HYPDX-4-dependent fluorescence was detected in vivo as well as ex vivo, indicating that hypoxia was localized to the central avascular retina where capillaries are attenuated (FIGS. 25A-27). HYPDX-4 dependent fluorescence was undetectable in age matched RA (P13) control pups. Retinal hypoxia in OIR pups was confirmed by ex vivo pimonidazole immunostaining (FIG. 27).

Ex Vivo HYPDX-4 Fluorescence Imaging of Retinal Cross Sections

Figure 28A:
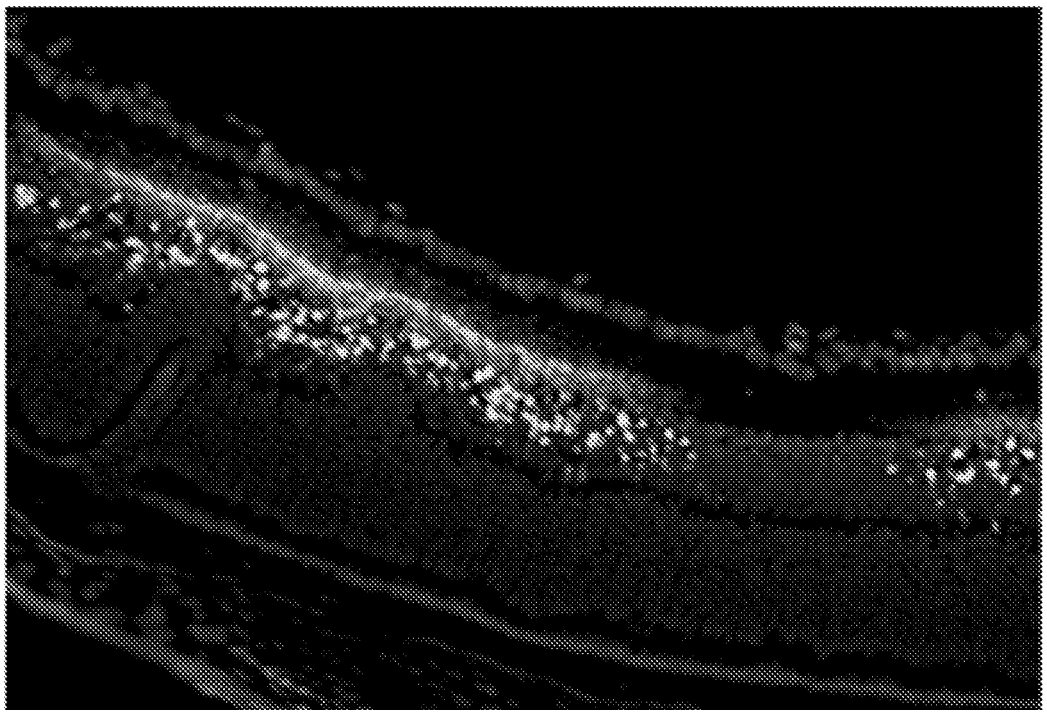
FIGS. 28A-B show spatial distribution of hypoxia was determined by HYPDX-4 dependent fluorescence activity in retinal cross sections. The images are of OIR mouse pups (P12) treated with HYPDX-4 or pimonidazole. Retinal nuclei were stained with DAPI (blue). Abbreviations: GCL=ganglion cell layer, IPL=inner plexiform layer, INL=inner nuclear layer, OPL=outer plexiform layer, ONL=outer nuclear layer. Specifically.
Figure 28B:
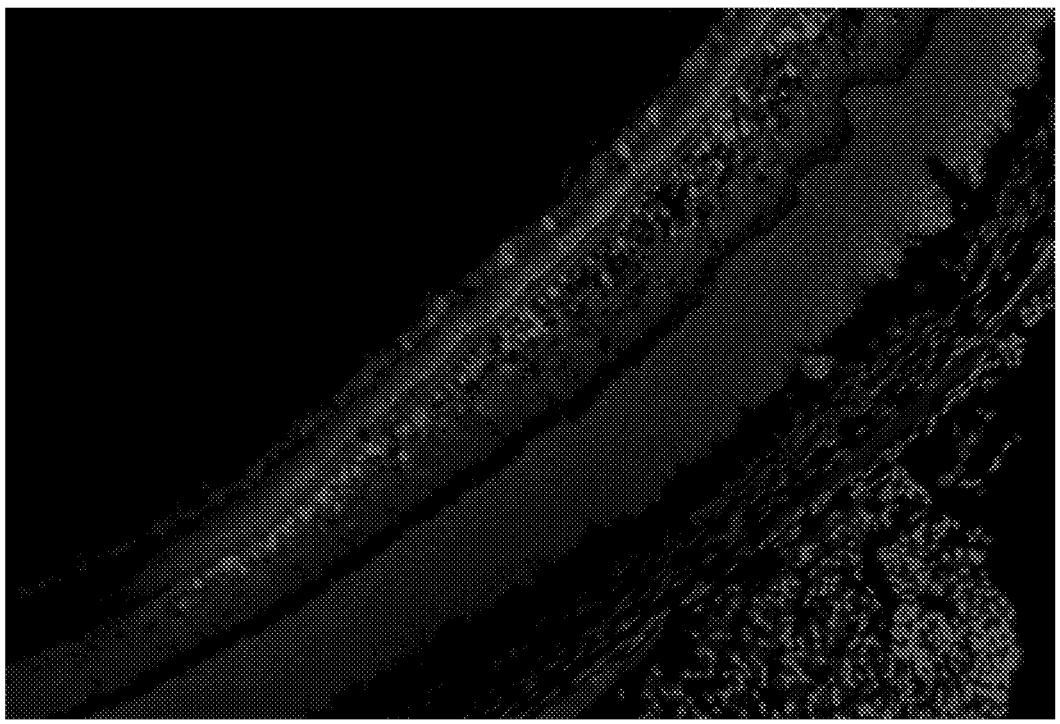
Figure 29A:
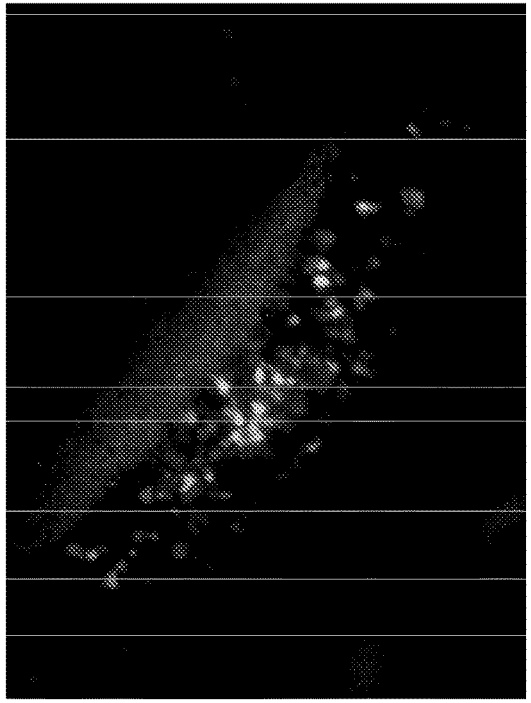
FIGS. 29A-D show immunofluorescence staining of human Müller cells with GS (red) and HYPDX-4 (green) localized in the inner retinal cross-sections from P13 OIR pups. Specifically.
Figure 29B:
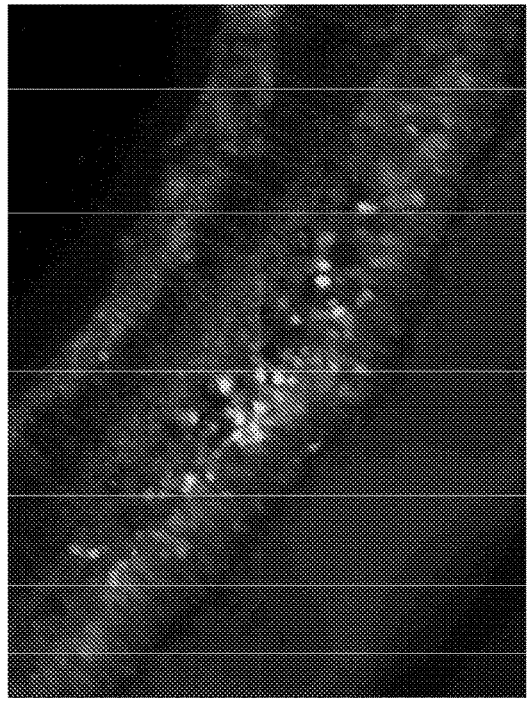
Figure 29C:
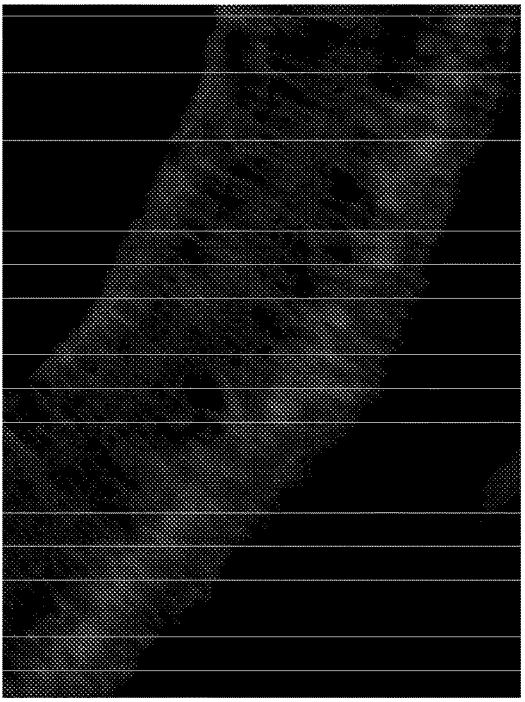
Figure 29D:
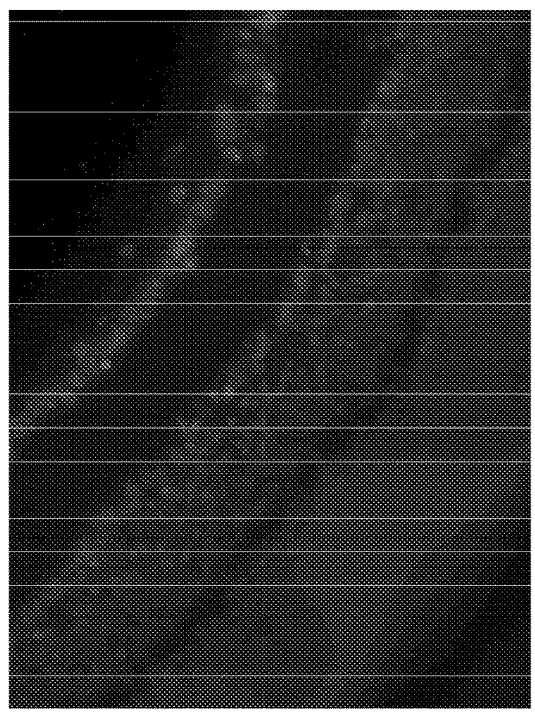
Figure 30A:
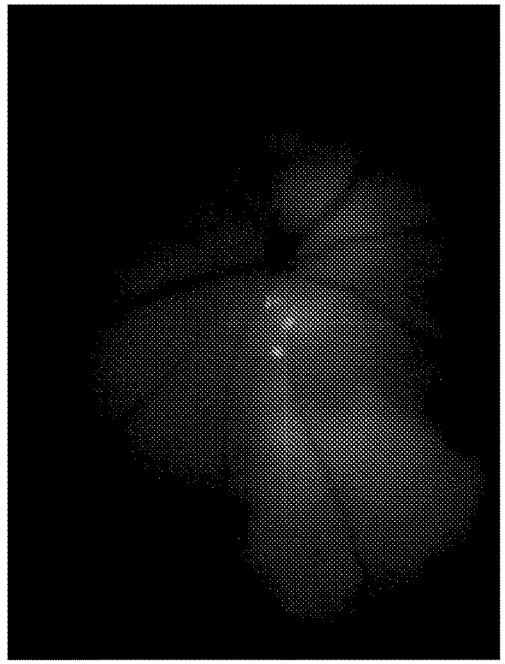
FIGS. 30A-D show HYPDX-4 dependent in vivo imaging of retinal hypoxia in a mouse model of retinal vein occlusion (RVO). HYPDX-4 or pimonidazole was administered by intraperitoneal injection 2 hours after laser-induced retinal vein occlusion. In vivo imaging was performed 22 hours post-injection. Specifically.
Figure 30B:
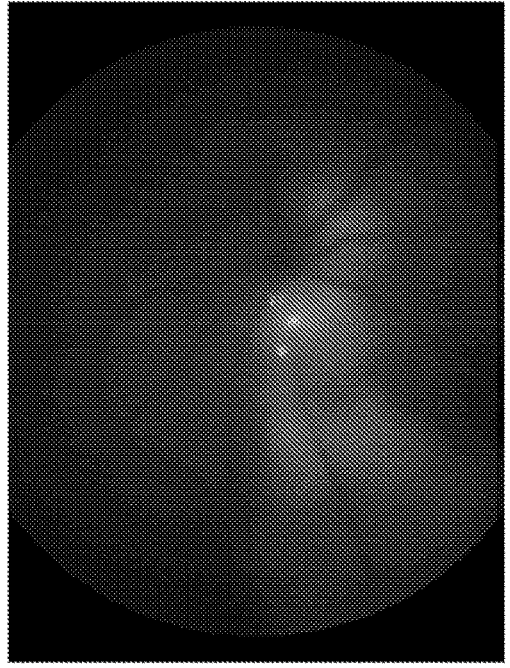
Figure 30C:
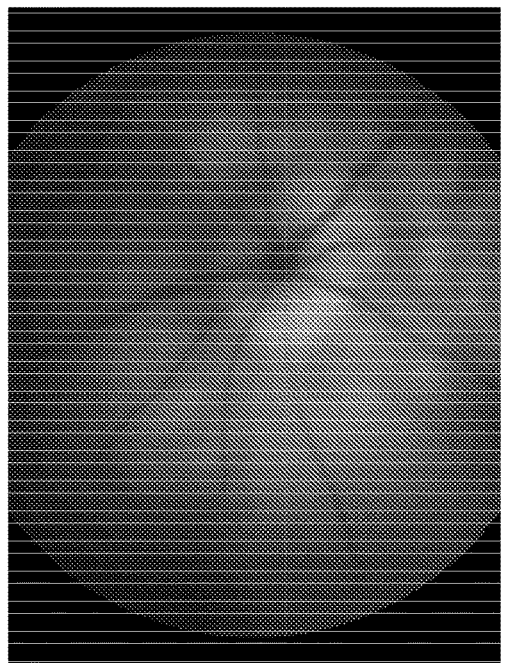
Figure 30D:
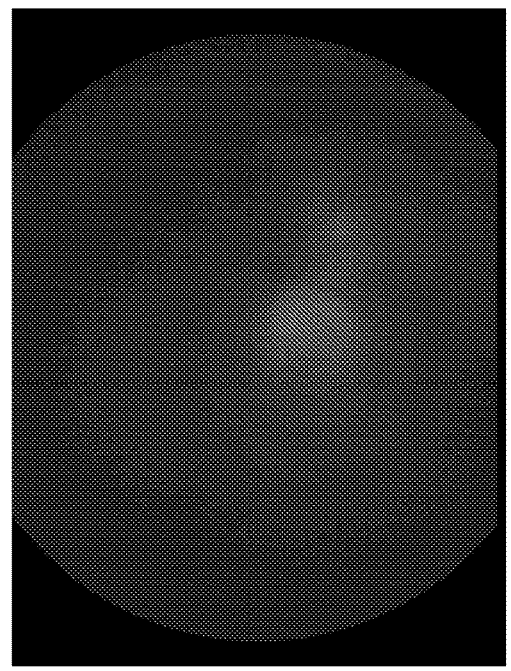

Fluorescence imaging of retinal transverse sections from OIR pups treated with HYPDX-4 was performed. HYPDX-4-dependent fluorescence indicated laterally alternating regions of hypoxia in the inner retina (FIG. 28A). Within a hypoxic region, proceeding from the inner limiting membrane (ILM) in a vertical sclerad direction, hypoxia was observed in the inner plexiform and inner nuclear layers. Hypoxia was not observed sclerad to the inner nuclear layer. The presence of hypoxia in the inner retina was confirmed using pimonidazole-adduct immunostaining in OIR retinal cross-sections (FIG. 28B). In general, ex vivo hypoxia imaging via pimonidazole-adduct immunostaining agreed with HYPDX-4 dependent ex vivo imaging, except the former technique indicated an extended region of hypoxia vitread into the inner plexiform layer.

In Vivo Imaging of Retinal Hypoxia in the Mouse Model of Retinal Vein Occlusion (RVO)

In vivo imaging of retinal hypoxia was performed in a mouse model of laser-induced retinal vein occlusion (RVO); an acute, early retinal hypoxia is observed in this model.[26] HYPDX-4 was administered by intraperitoneal injection two hours after the laser-induced retinal vein occlusion. HYPDX-4-dependent fluorescence was detected downstream and laterally from the occlusion (FIGS. 30A-32). Fluorescence angiography using TRITC-Dextran showed a lack of perfusion downstream form the laser-induced occlusion, while the adjacent retinal tissue was fully perfused. Ex vivo analysis of HYPDX-4-dependent fluorescence identified the same hypoxic areas in the retinas as the in vivo determination. The presence of tissue hypoxia in the RVO retina was confirmed by pimonidazole-adduct immunostaining (FIGS. 31B-32), although the pattern observed was different to some degree than that obtained by HYPDX-4-dependent imaging. HYPDX-4 produced a more confluent image of retinal hypoxia, whereas the pimonidazole-adduct staining pattern appeared patchy. Without wishing to be bound by theory, it is believed that this difference may be best explained by considering the increased tissue perfusion and bioavailability of HYPDX-4 relative to pimonidazole. Furthermore, the relative octanol-water partition coefficients support this explanation.

Toxicity of HYPDX-4

Figure 33A:
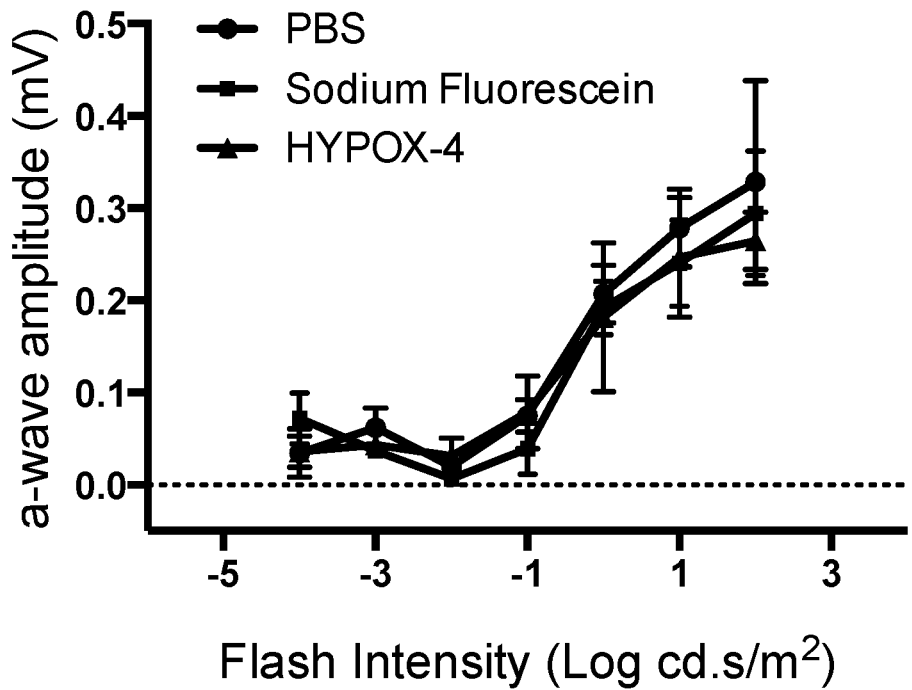
FIGS. 33A-B show retinal toxicity of HYPDX-4 assessed in RA raised mice and in cultured retinal cells. Specifically.
Figure 33B:
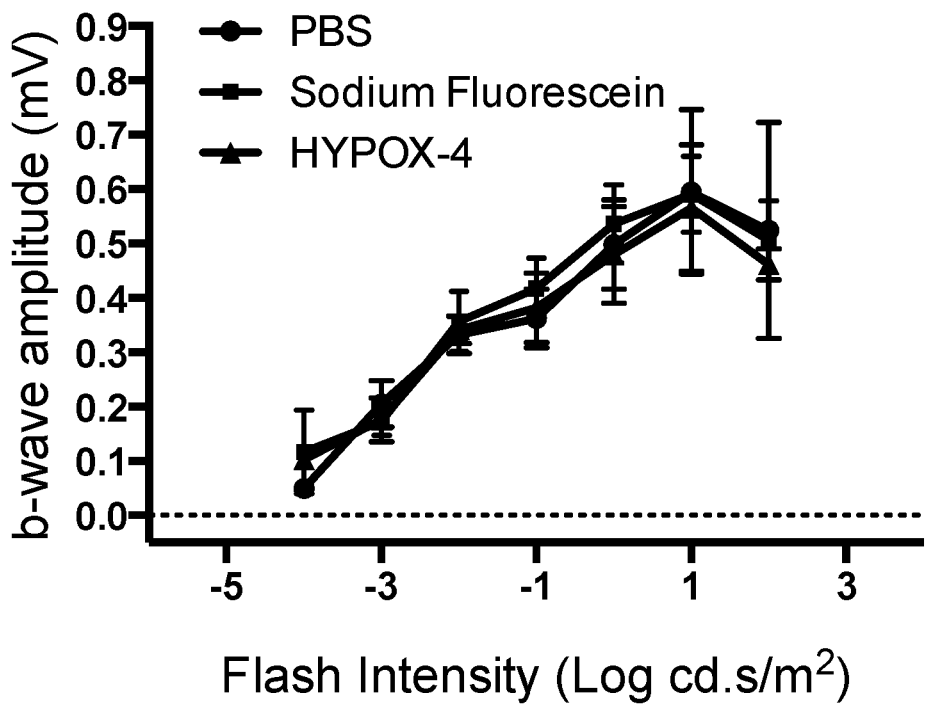
Figure 34A:
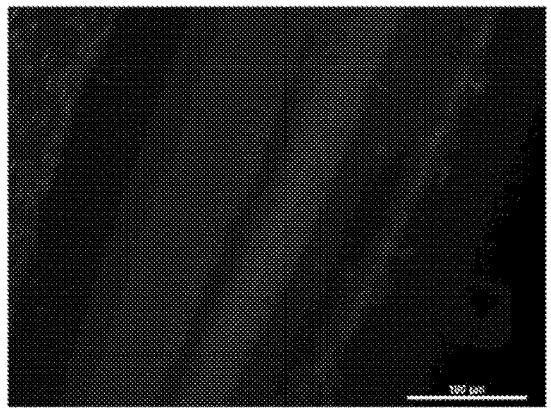
FIGS. 34A-F show a TUNEL assay performed in retinal cross sections from RA mice treated with 100 µM HYPDX-4 or DNase 1. Specifically.
Figure 34B:
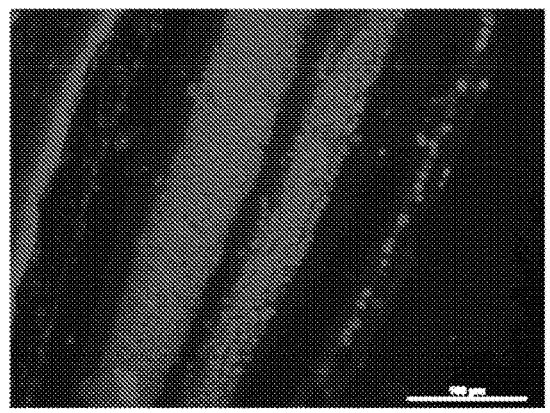
Figure 34C:
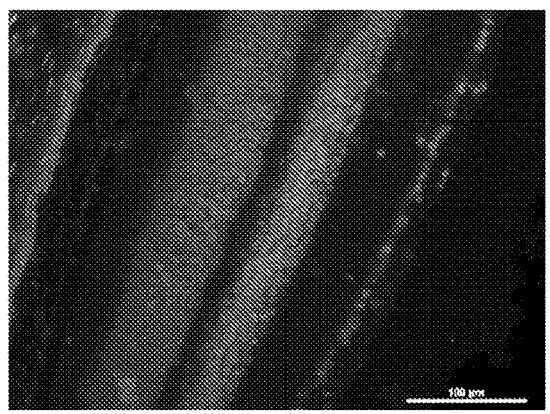
Figure 34D:
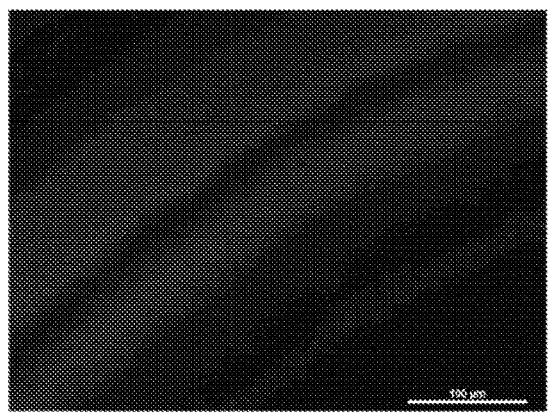
Figure 34E:
Figure 34F:
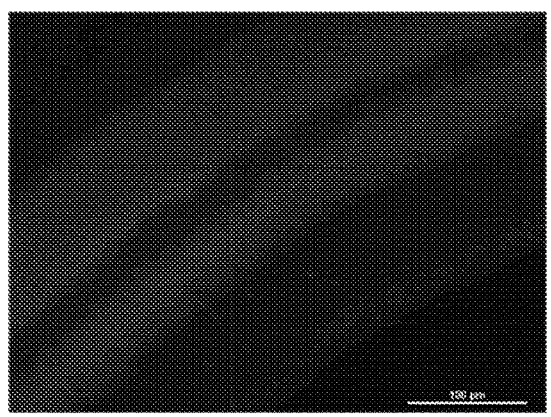
Figure 35A:
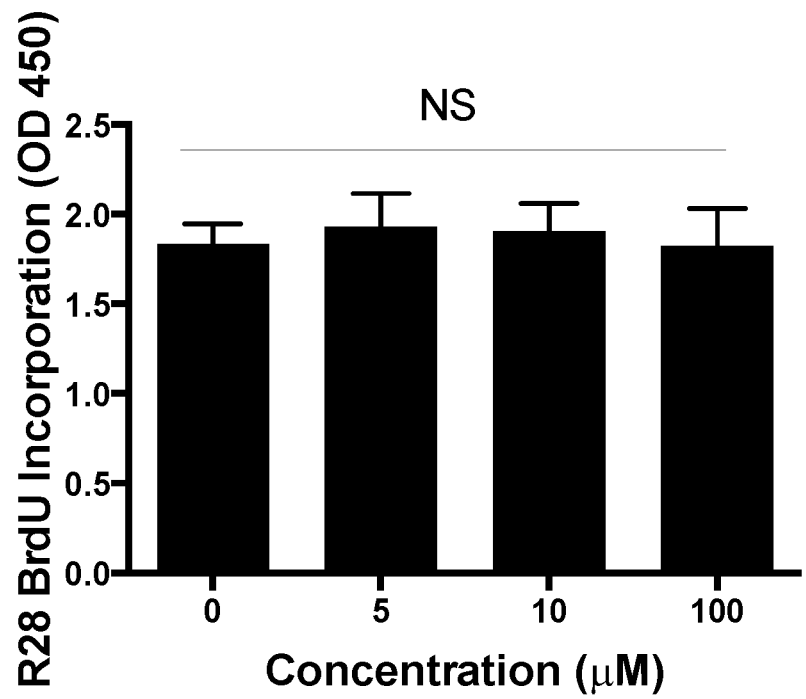
FIGS. 35A-B show in vitro cellular viability assessed by the BrdU assay using HYPDX-4 treated R28 and MIO-M1 cells. No effect on cellular viability was observed, indicating no acute cellular toxicity. Specifically.
Figure 35B:
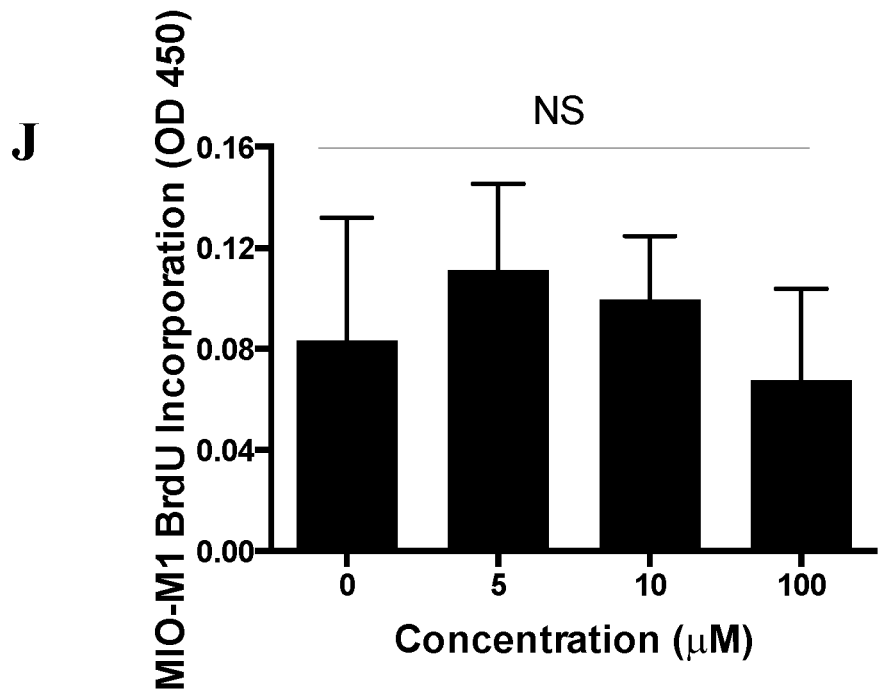

In vivo toxicity was assessed by electroretinography (ERG) measurements in retinas from RA mice. The HYPDX-4 probe (100 mg/kg) was injected systemically, and ERG measurements were recorded in dark-adapted mice seven days post-administration. No significant changes in mean a-wave and b-wave amplitudes at various flash intensities were observed as compared to vehicle treated mice (FIGS. 33A-B). Ex vivo analysis of retinal cross sections from mice treated with HYPDX-4 was performed to detect retinal cell apoptosis using the TUNEL assay. No apoptosis was observed, indicating no acute toxicity as compared to the positive control retinal tissues (FIGS. 34A-F). Cell viability assays were performed in R28 and MIO-M1 retinal cells treated with variable concentration of HYPDX-4 ranging from 0-100 μM; BrdU incorporation was analyzed. HYPDX-4 did not affect cell viability indicating that it is not acutely toxic to these retinal cells (FIGS. 35A-B). The ERG experiments were replicated three times. The results were statistically evaluated by ANOVA for mean a-wave and b-wave amplitudes at various flash intensities in different treatments groups. The cell viability assays were replicated three times, and were evaluated by Student's t-test for statistical significance.

Discussion

Figure 36:
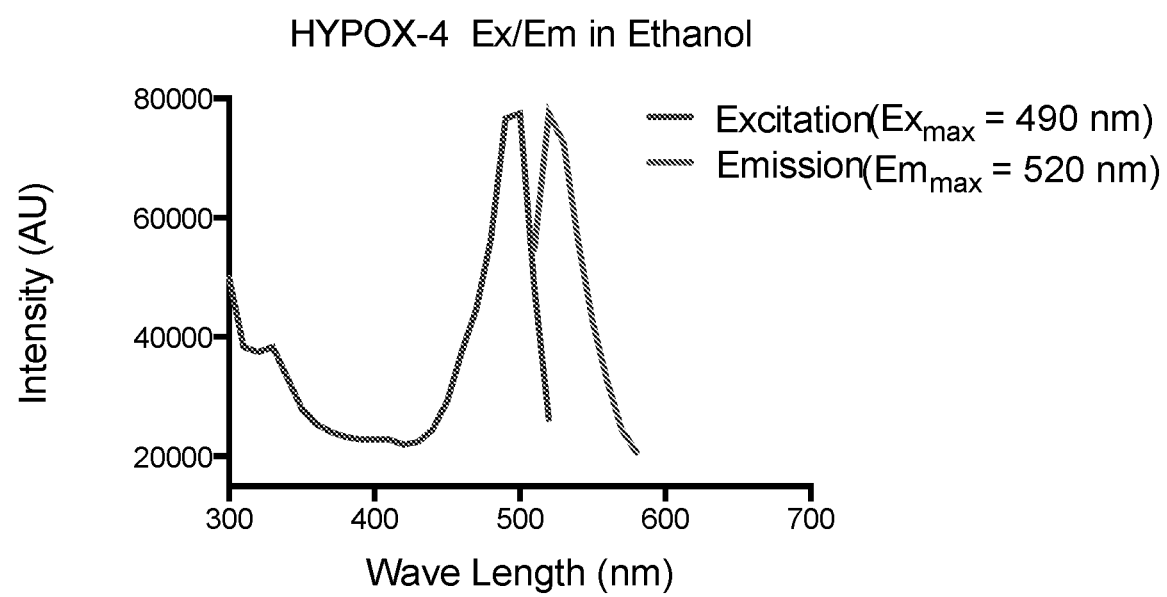
FIG. 36 shows that HYPDX-4 is highly fluorescent with an excitation maximum at 490 nm and emission at 520 nm.
Figure 37:
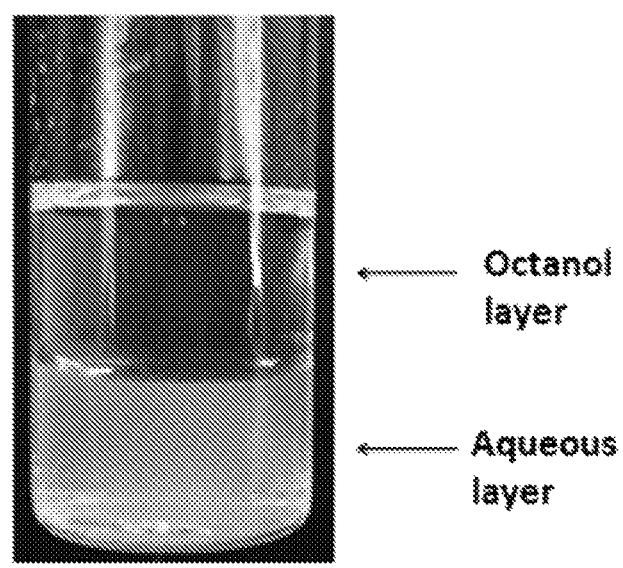
FIG. 37 shows that HYPDX-4 is soluble at a concentration of 100 µM in aqueous solvents (neat water or saline) and almost all aqueous buffers (PBS) including cell-culture mediums (DMEM with 10% FBS)
Figure 38:
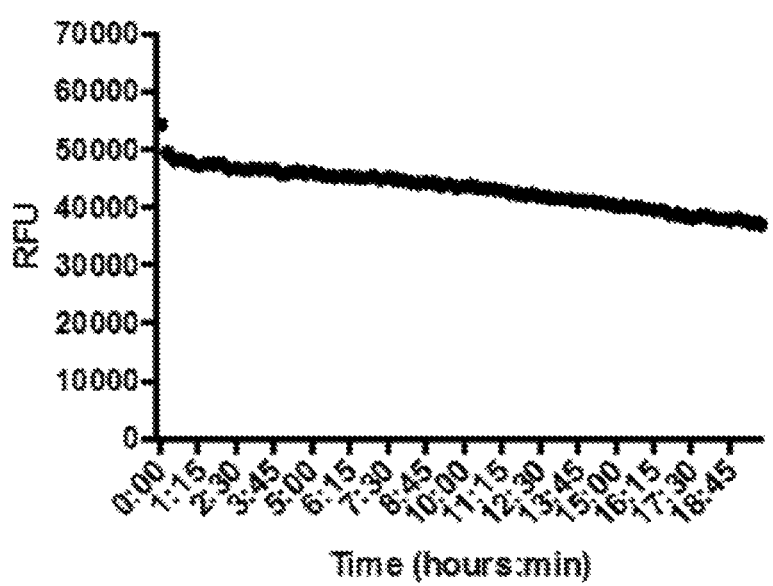
FIG. 38 shows in vitro stability of HYPDX-4 in solution at 37° C. HYPDX-4 was dissolved in phosphate buffer at a concentration of 100 nM and fluorescence was monitored at excitation maximum 490 nm and emission at 520 nm.

The synthetic strategy of HYPDX-4 was predicated on the need for a molecule with hypoxia-sensitive functionality, superior hypoxia-induced fluorescence and pharmacokinetic properties that would allow optimal tissue diffusion and bioavailability, all required for in vivo imaging. Oregon Green dye has several advantages for its application to biological systems. It has: a high extinction coefficient, high fluorescence quantum yield, pH insensitivity in the physiological range, high photostability and good tissue penetration. The 2-nitroimidazole moiety was incorporated into the structure of HYPDX-4 because it is reduced by nitroreductase, an enzyme activity that is increased in tissue hypoxia, allowing 2-nitroimidazole to yield hypoxia-sensitive functionality. The solubility of the HYPDX-4 was compared directly with the clinically relevant pimonidazole hydrochloride, using the octanol-water partition coefficient measurement method. Similar to pimonidazole hydrochloride, HYPDX-4 is highly soluble in aqueous medium in the free base form (FIGS. 36-37, Table 1). HYPDX-4 also possesses high photostability at room temperature in solution for at least 24 hours as determined by kinetic fluorescence studies (FIG. 38).

The hypoxia-dependent fluorescence of HYPDX-4 was tested in ARPE-19, MIO-M1, and R28 cells (FIGS. 22A-23D). Accordingly, it was shown that HYPDX-4 was efficiently internalized by these cells and an enhanced fluorescence reporter activity was observed in hypoxic cells as compared to normoxic controls. The achievement of hypoxia in these retinal cell lines was confirmed by pimonidazole-adduct immunostaining (FIGS. 24A-F).[24] These in vitro studies provided evidence for the feasibility of HYPDX-4 to report the hypoxic condition in a living system, warranting the extension of these studies to the in vivo setting using rodent models of ischemic retinopathy. HYPDX-4 toxicity was tested in cell viability assays. No differences in cell viability between retinal cells treated with HYPDX-4 and those treated with vehicle were observed (FIGS. 35A-B).

In vivo experiments were performed to determine whether hypoxia-dependent HYPDX-4 fluorescence could be observed in living animals predisposed to ischemic retinopathy. First, HYPDX-4 was tested in an established mouse model of oxygen-induced retinopathy (OIR).[27] In this model, OIR mice are exposed to 75% oxygen for five days from P7 to P12, causing vaso-obliteration, resulting in a central avascular retina. On P12, mice are placed in normoxia, causing the central avascular retina to become hypoxic within a few hours.[28,29] HYPDX-4 was systemically administered to OIR mice 2 hours after return to room air (P12) and to age-matched normoxic controls.

After 24 hours post-HYPDX-4 administration, in vivo imaging clearly demonstrated a HYPDX-4-dependent fluorescence within the central avascular retina, absent in adjacent perfused retina. This observation clearly indicates hypoxia in the central avascular retina (FIGS. 25A-27). Ex vivo evaluation of HYPDX-4 fluorescence from the same retinas was in close agreement with the in vivo findings, and IB4 counterstaining confirmed localization of hypoxia to the central capillary-free regions of the retina. HYPDX-4 fluorescence was undetectable in age-matched normoxic controls. These results agree with similar findings obtained using the ex vivo pimonidazole-adduct immunostaining technique.

Ex vivo fluorescence imaging of retinal cross-sections from OIR pups treated with HYPDX-4 confirmed the utility of HYPDX-4 to report hypoxia in cells and tissues. As demonstrated by representative images shown in FIGS. 28A-B, HYPDX-4 fluorescence was observed in hypoxic cells within capilary free areas; however, in adjacent perfused retina, it was undetecable. HYPDX-4 fluorescence activity was detected within the inner nuclear layer and the inner plexiform layer (FIG. 28A),[21] originating from cells extending axons into the inner plexiform layer proximal to the inner nuclear layer. This finding suggests a hypoxia-dependent HYPDX-4 fluorescence activity localized to amacrine cells and presumably Müller cells (FIGS. 29A-D). The presence of hypoxia in the inner retina was also validated using pimonidazole-adduct immunostaining in OIR retinal cross-sections (FIG. 28B). Interestingly, the results were consistent with those obtained using HYPDX-4. Hypoxia sclerad to the edge of the inner nuclear layer was not detected.

Figure 31B:
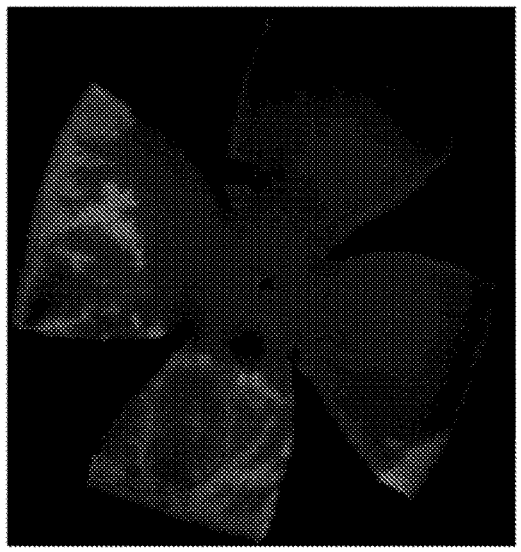
FIGS. 31A-D show HYPDX-4 dependent ex vivo imaging of retinal hypoxia in a mouse model of retinal vein occlusion (RVO). Specifically.
Figure 31D:
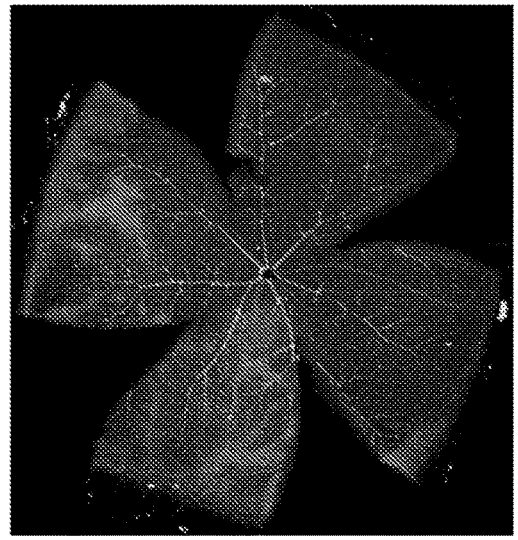
Figure 31A:
Figure 31C:
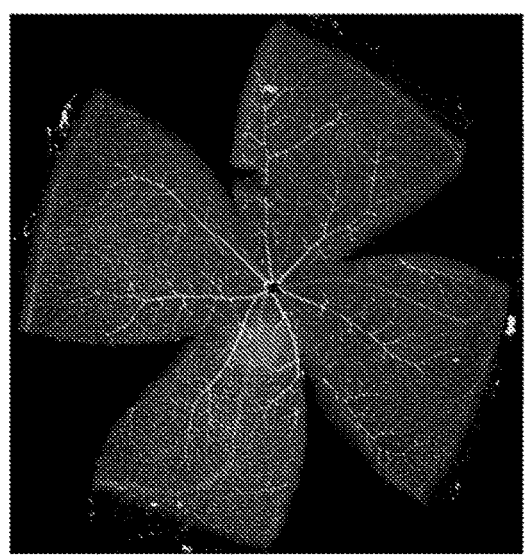
Figure 32:
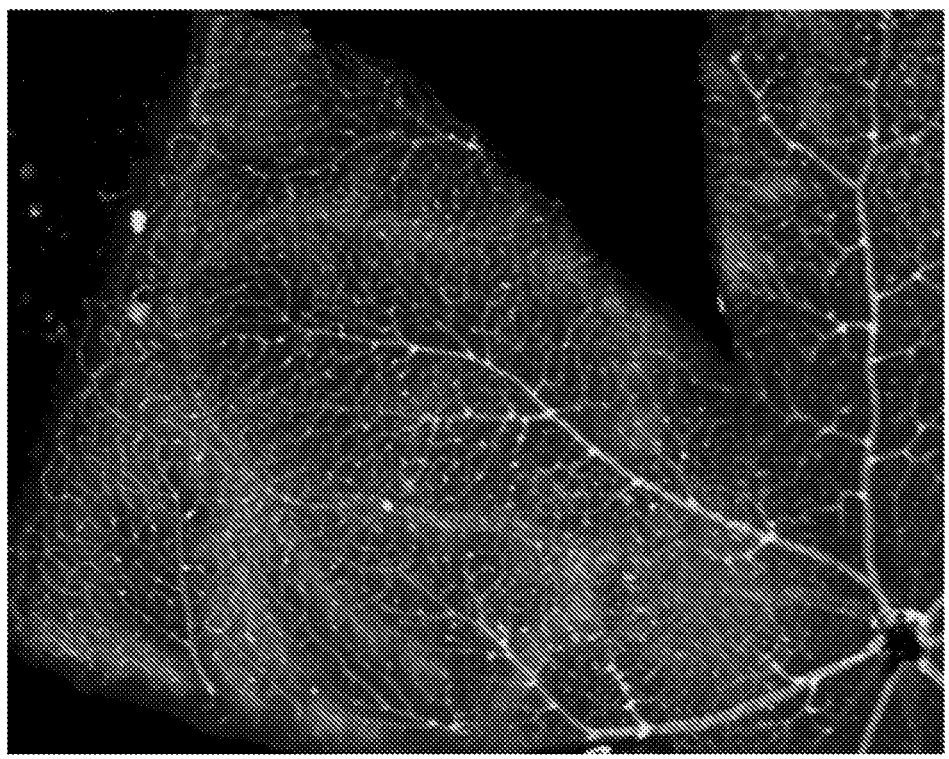
FIG. 32 shows an enlarged view of a portion of FIG. 31D. Abbreviations: A and V corresponds to arteries and veins respectively.

Additionally, HYPDX-4 was tested it in a mouse model of retinal vein occlusion (RVO) to further confirm the suitability for in vivo imaging of retinal hypoxia. In this model, laser-induced occlusion of a retinal vein results in the rapid onset of hypoxia downstream from the occlusion.[26] HYPDX-4 was systemically administered two hours after the vein occlusion; twenty-four hours later, HYPDX-4 fluorescence was observed, indicating hypoxia downstream from the photocoagulation site (FIGS. 30A-D). Fluorescence angiography of the same eye using TRITC-Dextran showed non-perfusion downstream from the laser-induced occlusion with adjacent retinal tissue being fully perfused. Ex vivo analysis of HYPDX-4 fluorescence from the same retinal tissues agreed with the in vivo findings (FIG. 31A). The presence of tissue hypoxia in this RVO model was also confirmed using pimonidazole-adduct immunostaining (FIGS. 31B-32). Without wishing to be bound by theory, it is believed that the irregular pattern of immunostaining observed around the vein may be due to limited pimonidazole bioavailability as described in the result section.

Electroretinography (ERG) measurements in dark-adapted RA mice seven days post systemic administration of HYPDX-4 revealed no significant changes in mean a-wave and b-wave amplitudes compared to vehicle indicating no effect of HYPDX-4 on retinal physiology (FIGS. 33A-B). Ex vivo analysis of the retinal cross sections from RA mice treated with HYPDX-4 were also examined using the TUNEL assay. No significant toxicity-related apoptosis was observed as compared to the positive control tissues (FIGS. 34A-F).

In summary, a facile route for the synthesis of HYPDX-4, a hypoxia-sensitive imaging agent, has been developed, the synthesis including conjugating 2-nitroimidazole to the fluorescent dye, Oregon green. HYPDX-4 is a novel probe that is not acutely toxic to retinal tissues and demonstrates pharmacokinetic properties required for efficient systemic delivery and bioavailability within the retina. HYPDX-4 provides in vivo detection of retinal hypoxia in mouse models of oxygen induced retinopathy (OIR) and retinal vein occlusion (RVO). This is believed to be the first report of real time hypoxia imaging in living animals by a fluorescence-based method. HYPDX-4 hypoxia-induced retinal imaging is non-invasive and provides an excellent tool for diagnosis and monitoring of retinal hypoxia in preclinical disease models and patients.

Throughout this document, various references are mentioned. All such references are incorporated herein by reference.

REFERENCES

1. Gariano R F & Gardner T W (2005) Retinal angiogenesis in development and disease. *Nature* 438(7070):960-966.
2. Anderson C G, Benitz W E, & Madan A (2002) Retinopathy of prematurity (ROP) and pulse oximetry: A national survey of recent practices. *Pediatr Res* 51(4): 367a-367a.
3. Wang X Q, Wang G B, & Wang Y (2009) Intravitreous Vascular Endothelial Growth Factor and Hypoxia-Inducible Factor 1a in Patients With Proliferative Diabetic Retinopathy. *Am J Ophthalmol* 148(6):883-889.
4. Rehak J & Rehak M (2008) Branch retinal vein occlusion: Pathogenesis, visual prognosis, and treatment modalities. *Curr Eye Res* 33(2):111-131.
5. Hartnett M E & Penn J S (2012) Mechanisms and Management of Retinopathy of Prematurity. *New Engl J Med* 367(26):2515-2526.
6. Ashton N & Cook C (1954) Direct observation of the effect of oxygen on developing vessels: preliminary report. *The British journal of ophthalmology* 38(7):433-440.
7. Ashton N (1954) Pathological basis of retrolental fibroplasia. *The British journal of ophthalmology* 38(7):385-396.
8. O'Mahoney P R A, Wong D T, & Ray J G (2008) Retinal vein occlusion and traditional risk factors for atherosclerosis. *Arch Ophthalmol-Chic* 126(5):692-699.
9. Robbins S G, Conaway J R, Ford B L, Roberto K A, & Penn J S (1997) Detection of vascular endothelial growth factor (VEGF) protein in vascular and non-vascular cells of the normal and oxygen-injured rat retina. *Growth Factors* 14(4):229-&.
10. Xin X B, et al. (2013) Hypoxic retinal Müller cells promote vascular permeability by HIF-1-dependent up-regulation of angiopoietin-like 4. *P Natl Acad Sci USA* 110(36):E3425-E3434.
11. Linsenmeier R A, et al. (1998) Retinal hypoxia in long-term diabetic cats. *Invest Ophth Vis Sci* 39(9):1647-1657.
12. Berkowitz B A & Penn J S (1998) Abnormal panretinal response pattern to carbogen inhalation in experimental retinopathy of prematurity. *Invest Ophthalmol Vis Sci* 39(5):840-845.
13. Hardarson S H, et al. (2006) Automatic retinal oximetry. *Investigative ophthalmology & visual science* 47(11): 5011-5016.
14. Shahidi M, Shakoor A, Blair N P, Mori M, & Shonat R D (2006) A method for chorioretinal oxygen tension measurement. *Current eye research* 31(4):357-366.
15. Dai C, Liu X, Zhang H F, Puliafito C A, & Jiao S (2013) Absolute retinal blood flow measurement with a dual-beam Doppler optical coherence tomography. *Investigative ophthalmology & visual science* 54(13):7998-8003.
16. Soetikno B T, et al. (2015) Inner retinal oxygen metabolism in the 50/10 oxygen-induced retinopathy model. *Scientific reports* 5:16752.
17. Scott A & Fruttiger M (2010) Oxygen-induced retinopathy: a model for vascular pathology in the retina. *Eye* 24(3):416-421.
18. Busk M, et al. (2013) PET imaging of tumor hypoxia using 18F-labeled pimonidazole. *Acta oncologica* 52(7): 1300-1307.
19. Kizaka-Kondoh S & Konse-Nagasawa H (2009) Significance of nitroimidazole compounds and hypoxia-inducible factor-1 for imaging tumor hypoxia. *Cancer science* 100(8):1366-1373.

20. Yang Y, et al. (2012) Magnetic resonance imaging retinal oximetry: a quantitative physiological biomarker for early diabetic retinopathy? *Diabetic medicine: a journal of the British Diabetic Association* 29(4):501-505.
21. Mowat F M, et al. (2010) HIF-1alpha and HIF-2alpha are differentially activated in distinct cell populations in retinal ischaemia. *Plos One* 5(6):e11103.
22. Varia M A, et al. (1998) Pimonidazole: A novel hypoxia marker for complementary study of tumor hypoxia and cell proliferation in cervical carcinoma. *Gynecol Oncol* 71(2):270-277.
23. Uddin M I, et al. (2015) Applications of Azo-Based Probes for Imaging Retinal Hypoxia. *Acs Med Chem Lett* 6(4):445-449.
24. Evans S M, et al. (2014) Molecular Probes for Imaging of Hypoxia in the Retina. *Bioconjugate Chem* 25(11): 2030-2037.
25. Ross D, Beall H D, Siegel D, Traver R D, & Gustafson D L (1996) Enzymology of bioreductive drug activation. *The British journal of cancer. Supplement* 27:S1-8.
26. Stefansson E, Novack R L, & Hatchell D L (1990) Vitrectomy prevents retinal hypoxia in branch retinal vein occlusion. *Invest Ophthalmol Vis Sci* 31(2):284-289.
27. Smith L E, et al. (1994) Oxygen-induced retinopathy in the mouse. *Investigative ophthalmology & visual science* 35(1):101-111.
28. Connor K M, et al. (2009) Quantification of oxygen-induced retinopathy in the mouse: a model of vessel loss, vessel regrowth and pathological angiogenesis. *Nature protocols* 4(11):1565-1573.
29. Stahl A, et al. (2010) The mouse retina as an angiogenesis model. *Invest Ophthalmol Vis Sci* 51(6):2813-2826.
30. Limb G A, Salt T E, Munro P M, Moss S E, & Khaw P T (2002) In vitro characterization of a spontaneously immortalized human Müller cell line (MIO-M1). *Invest Ophthalmol Vis Sci* 43(3):864-869.
31. Zhang H, et al. (2007) Development of a new mouse model of branch retinal vein occlusion and retinal neovascularization. *Japanese journal of ophthalmology* 51(4):251-257.
32. Domenici L, Berardi N, Carmignoto G, Vantini G, & Maffei L (1991) Nerve growth factor prevents the amblyopic effects of monocular deprivation. *Proc Natl Acad Sci USA* 88(19):8811-8815.
33. Rex T S, et al. (2004) Systemic but not intraocular Epo gene transfer protects the retina from light and genetic induced degeneration. *Molecular therapy: the journal of the American Society of Gene Therapy* 10(5):855-861.
34. Okuda, K., et al., 2-Nitroimidazole-Tricarbocyanine Conjugate as a Near-Infrared Fluorescent Probe for in Vivo Imaging of Tumor Hypoxia. Bioconjugate Chemistry, 2012. 23(3): p. 324-329.
35. Evans, S. M., et al., *Molecular Probes for Imaging of Hypoxia in the Retina*. Bioconjugate Chemistry, 2014. 25(11): p. 2030-2037.

What is claimed is:

1. A compound for detecting hypoxic cells and tissue, the compound comprising a probe selected from the group consisting of a hypoxia sensitive 2-nitroimidazole containing fluorescence imaging probe, a hypoxia sensitive reversible ON-OFF fluorescence imaging probe, a hypoxia sensitive azo-based fluorescence imaging probe, and combinations thereof;
   (i) wherein the hypoxia sensitive 2-nitroimidazole containing fluorescence imaging probe comprises a structure selected from the group consisting of:

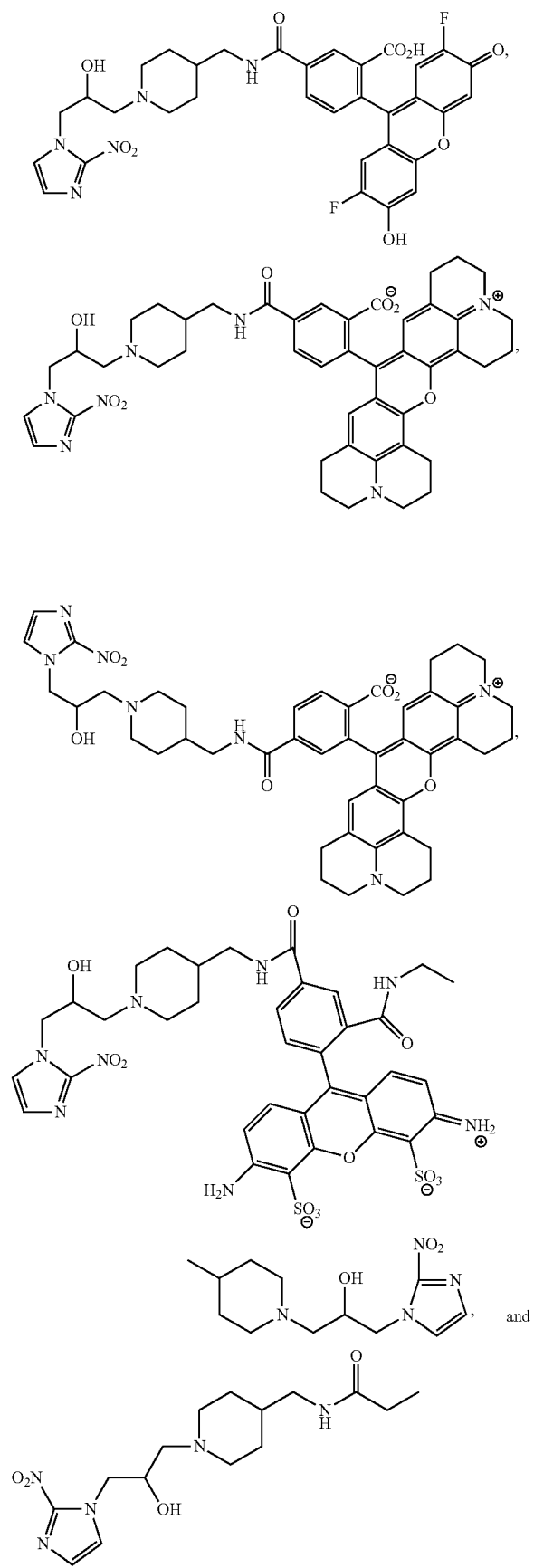

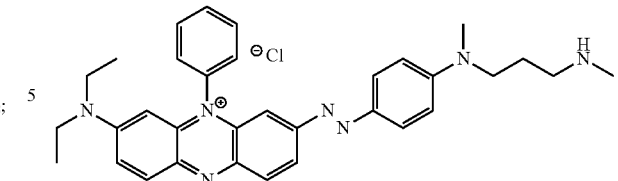

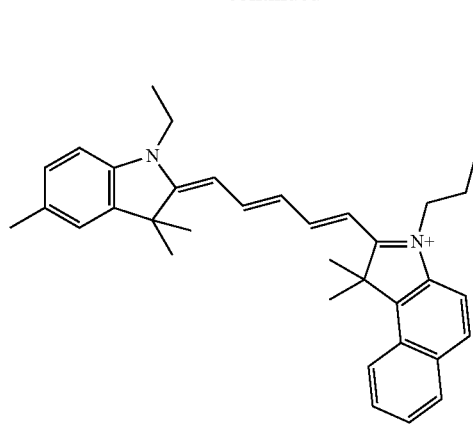

(ii) wherein the hypoxia sensitive reversible ON-OFF fluorescence imaging probe comprise the structure:

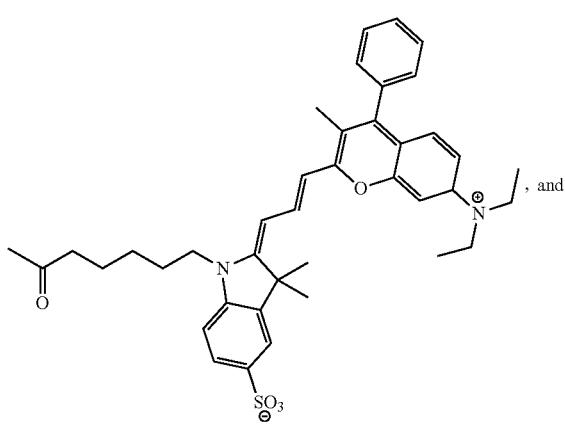

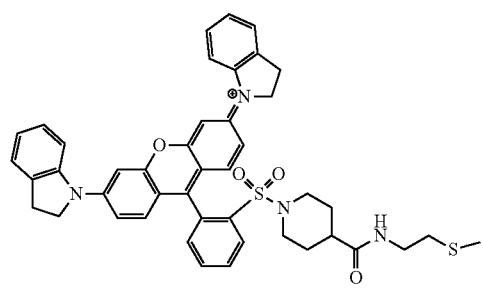

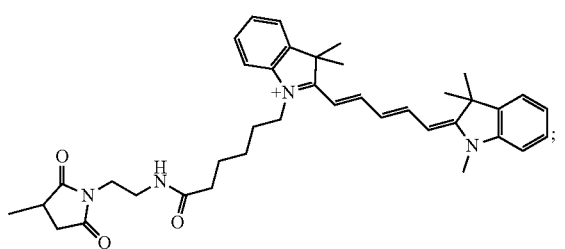

and (iii) wherein the hypoxia sensitive azo-based fluorescence imaging probe comprises a structure selected from the group consisting of:

2. The compound of claim 1, wherein the hypoxia sensitive 2-nitroimidazole containing fluorescence imaging probe comprises the structure selected from the group consisting of:

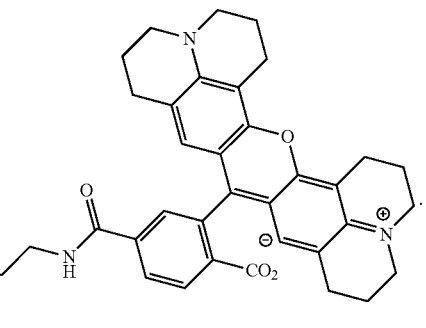

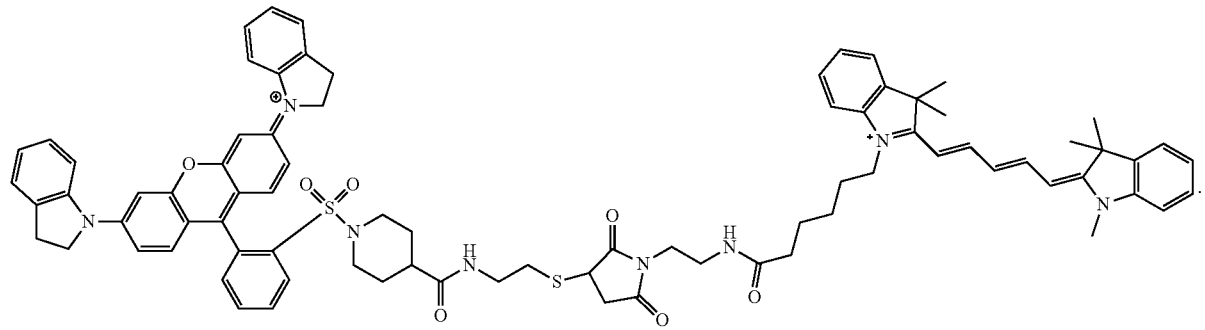 [SMILES: CN1/C(=C/C=C/C=C/C2=[N+](CCCCCC(=O)NCCN3C(=O)CC(SCCNC(=O)C4CCN(S(=O)(=O)c5ccccc5-c5c6cc/c(=[N+]7\CCc8ccccc87)cc-6oc6cc(N7CCc8ccccc87)ccc56)CC4)C3=O)c3ccccc3C2(C)C)C(C)(C)c2ccccc21]

3. The compound of claim 1, wherein the structure of the hypoxia sensitive 2-nitroimidazole containing fluorescence imaging probe comprises:

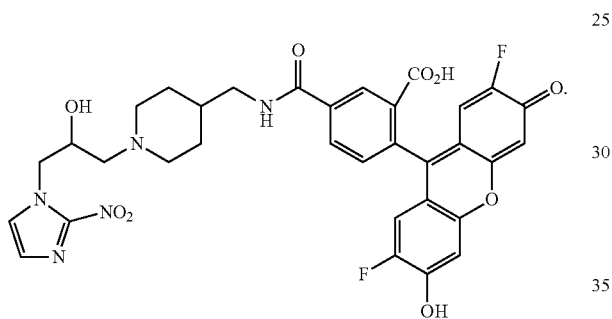

4. The compound of claim 1, wherein the structure of the hypoxia sensitive ON-OFF fluorescence imaging probe comprises:
wherein increased fluorescent intensity indicates that the cells or tissue is hypoxic.

5. The compound of claim 1, wherein the hypoxia sensitive azo-based fluorescence imaging probe comprises the structure selected from the group consisting of:

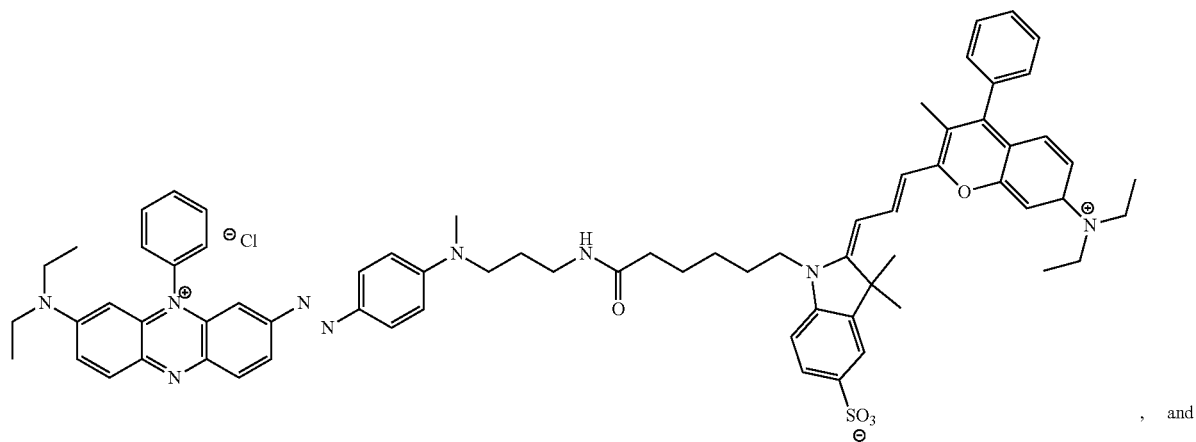

, and

-continued
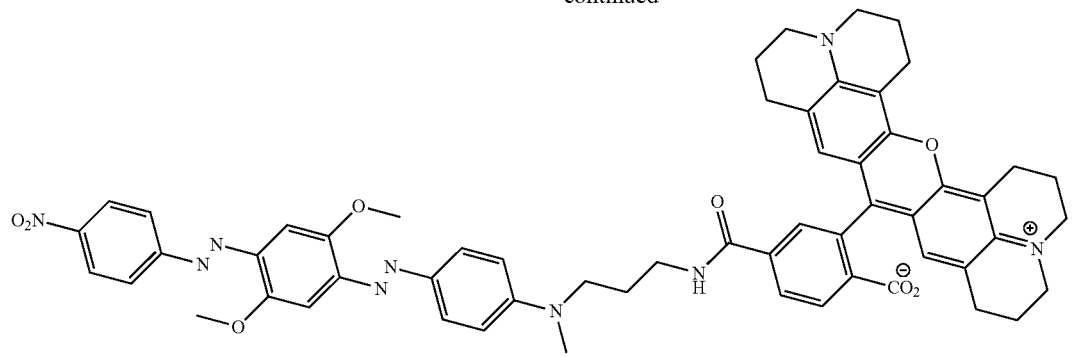
6. The compound of claim 1, wherein the azo-based fluorescence imaging probe includes a hypoxia-sensitive cleavable azo-bond.
7. A method for detecting hypoxic cells and tissue, comprising:
   contacting the cells or tissue with the probe of claim 1; and
   detecting fluorescent intensity of the cell or tissue;
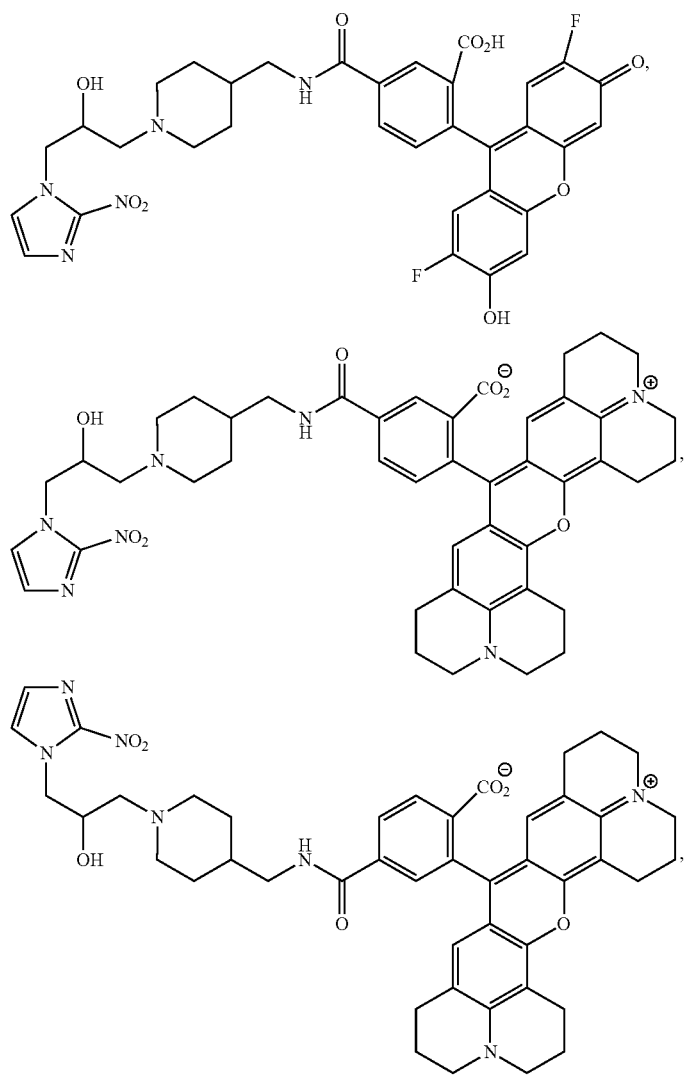

-continued

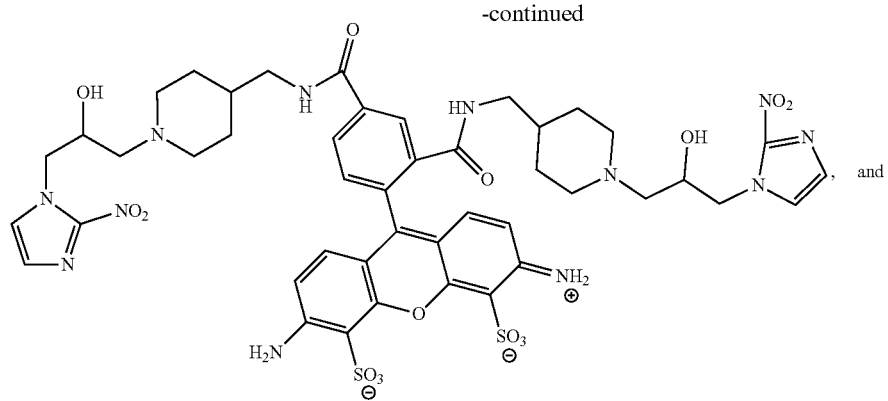

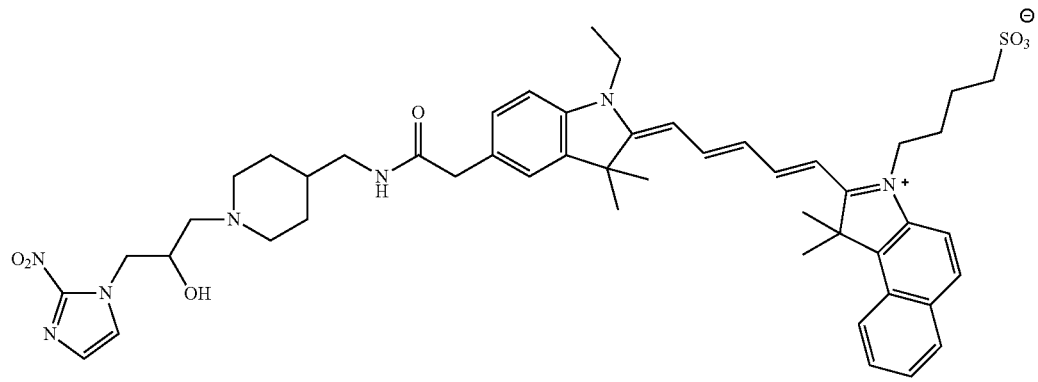

8. The method of claim 7, wherein the nitro groups of the hypoxia sensitive 2-nitroimidazole containing fluorescence imaging probe are bioreduced by nitroreductases in hypoxic cells or tissue, thereby increasing fluorescent intensity.

9. The method of claim 7, wherein the hypoxia sensitive reversible ON-OFF fluorescence imaging probe provides increased fluorescent intensity in the presence of hypoxic cells or tissue.

10. The method of claim 7, wherein the azo-bond of the hypoxia sensitive azo-based fluorescence imaging probe is cleaved in hypoxic cells or tissue, thereby increasing fluorescent intensity.

11. The method of claim 7, wherein the cells or tissue include retinal cells.

12. The method of claim 11, wherein the retinal cells include retinal cells of a subject, the method further comprising identifying the subject as having hypoxic cells or tissue when there is increased fluorescent intensity detected.

13. The method of claim 12, further comprising identifying the subject as having a retinal disease when there is increased fluorescent intensity detected.

14. The method of claim 7, wherein the cells or tissue include tumor cells.

15. The method of claim 14, wherein the tumor cells include tumor cells of a subject, the method further comprising identifying the subject as having hypoxic cells or tissue when there is increased fluorescent intensity detected.

16. The compound of claim 1, further comprising at least one microorganism reducing agent selected from the group consisting of an antibacterial agent, an antifungal agent, and a combination thereof.

17. The compound of claim 16, wherein the microorganism reducing agent is selected from the group consisting of paraben, chlorobutanol, phenol, sorbic acid, and combinations thereof.

* * * * *